(12) United States Patent
Unciti-Broceta et al.

(10) Patent No.: US 10,294,227 B2
(45) Date of Patent: May 21, 2019

(54) COMPOUNDS

(71) Applicant: UNIVERSITY COURT OF THE UNIVERSITY OF EDINBURGH, Edinburgh (GB)

(72) Inventors: Asier Unciti-Broceta, Edinburgh (GB); Craig Fraser, Edinburgh (GB); Neil O. Carragher, Edinburgh (GB)

(73) Assignee: UNIVERSITY COURT OF THE UNIVERSITY OF EDINBURGH, Edinburgh (GB)

( * ) Notice: Subject to any disclaimer, the term of this patent is extended or adjusted under 35 U.S.C. 154(b) by 0 days.

(21) Appl. No.: 15/576,101

(22) PCT Filed: Apr. 15, 2016

(86) PCT No.: PCT/GB2016/051057
§ 371 (c)(1),
(2) Date: Nov. 21, 2017

(87) PCT Pub. No.: WO2016/185160
PCT Pub. Date: Nov. 24, 2016

(65) Prior Publication Data
US 2018/0127422 A1    May 10, 2018

(30) Foreign Application Priority Data
May 21, 2015 (GB) .................................. 1508747.1

(51) Int. Cl.
C07D 487/04 (2006.01)
C07D 519/00 (2006.01)
(Continued)

(52) U.S. Cl.
CPC .......... *C07D 487/04* (2013.01); *A61K 31/519* (2013.01); *A61K 45/06* (2013.01);
(Continued)

(58) Field of Classification Search
CPC .... C07D 487/04; C07D 519/00; C12Q 1/485; Y02A 50/385; A61K 31/519; A61K 45/06; A61K 2300/00; A61P 25/28; A61P 43/00
See application file for complete search history.

(56) References Cited

FOREIGN PATENT DOCUMENTS

WO   WO-84003564 A1   9/1984
WO   WO-02076986 A1   10/2002
(Continued)

OTHER PUBLICATIONS

Fraser et al., Rapid Discovery and Structure-Activity Relationships of Pyrazolopyrimidines That Potently Suppress Breast Cancer Cell Growth via SRC Kinase Inhibition with Exceptional Selectivity over ABL Kinase, Cancer Research U.K. Edinburgh Centre and MRC Human Genetics Unit, Journal of Medicinal Chemistry, 2016.*

(Continued)

*Primary Examiner* — Alexander R Pagano
*Assistant Examiner* — Ebenezer O Sackey
(74) *Attorney, Agent, or Firm* — Winstead PC

(57) ABSTRACT

A first aspect of the invention relates to a compound of formula (I), or a pharmaceutically acceptable salt or ester thereof, (Formula (I)) wherein: $R_1$ is $(CH_2)_m NR_{11}R_{12}$; $R_2$ is selected from H, halo, $OR_{13}$, $NHR_{13}$, alkyl, alkenyl and alkynyl; $R_3$ is selected from alkyl, alkenyl, alkynyl, aryl, halo, aryloxy, $NHCO_2R_4$, $NHCONR_5R_6$, $NHCOR_7$, NH-alkyl, NH-alkenyl, $NH(CH_2)_n$-aryl, $(CH_2)_p$-heteroaryl, $(CH_2)_q CO_2R_8$, $(CH_2)_r COR_9$ and $NHSO_2R_{10}$, wherein each alkyl, alkenyl, aryl or heteroaryl moiety in the aforementioned list is optionally further substituted by one or more groups selected from alkyl, halo OH, $NH_2$, alkoxy, aryloxy, alkylamino, arylamino, carboxyl and carboxamide; $R_4$ to $R_{10}$ and $R_{13}$ are each independently selected from alkyl, alkenyl and aryl; $R_{11}$ and $R_{12}$ are each independently selected from alkyl and alkenyl; or $R_{11}$ and $R:_{12}$ are linked together with the nitrogen to which they are attached to form a heterocycloalkyl or heterocycloalkenyl group; n, m, p, q and r are each independently selected from 0, 1, 2, 3, 4, 5 and 6. Further aspects relate to pharmaceutical compositions, therapeutic uses and process for preparing according to the invention.

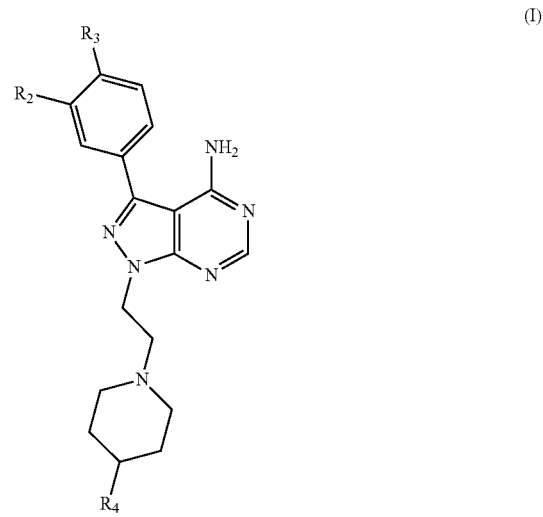

(I)

24 Claims, 9 Drawing Sheets

(51) Int. Cl.
    A61P 43/00    (2006.01)
    A61K 31/519   (2006.01)
    A61K 45/06    (2006.01)
    A61P 25/28    (2006.01)
    C12Q 1/48     (2006.01)

(52) U.S. Cl.
    CPC ............... *A61P 25/28* (2018.01); *A61P 43/00* (2018.01); *C07D 519/00* (2013.01); *C12Q 1/485* (2013.01); *Y02A 50/385* (2018.01)

(56) References Cited

FOREIGN PATENT DOCUMENTS

| WO | WO-2011094628 A1 | 8/2011 |
| WO | 2013177668 | * 12/2013 |
| WO | WO-2013177668 A1 | 12/2013 |
| WO | WO-2015018333 A1 | 2/2015 |

OTHER PUBLICATIONS

Berge, S.M., et al., "Pharmaceutical Salts," Journal of Pharmaceutical Sciences, Jan. 1977, vol. 66, No. 1, pp. 1-19.
Gennaro, A.R., "Diluting Agents," Remington's Pharmaceutical Sciences, 17th Edition, Mack Publishing Company, Easton, Pennsylvania, 1985, pp. 1292-1296.
Goodman, L.S., et al., "General Principles," The Pharmacological Basis of Therapeutics, Fifth Edition, Macmillan Publishing Co., Inc., New York, 1975, pp. 1-2.
March, J., "The Cahn-Ingold-Prelog System," Advanced Organic Chemistry, Reactions, Mechanisms, and Structure, Third Edition, John Wiley & Sons, Inc., New York, 1985, pp. 96-98.
Wade, A., et al., Handbook of Pharmaceutical Excipients, Second Edition, American Pharmaceutical Association, Washington DC, 1994, pp. v-vi.
De Wispelaere, M., et al., "The Small Molecules AZD0530 and Dasatinib Inhibit Dengue Virus RNA Replication via Fyn Kinase," Journal of Virology, vol. 87, No. 13, Jul. 2013, pp. 7367-7381.
Bissmire, Stewart, "International Search Report," prepared for PCT/GB2016/051057, dated May 30, 2016, three pages.
Creedon, H., et al., "Src Kinase Inhibitors: Promising Cancer Therapeutics?" Critical Reviews in Oncogenesis, vol. 17, No. 2, 2012, pp. 145-159.
Carragher, N., et al., "Advancing Cancer Drug Discovery towards More Agile Development of Targeted Combination Therapies," Future Med. Chem., vol. 4, No. 1, 2012, pp. 87-105.
Allington, T. M., et al., "Activated Abl Kinase Inhibits Oncogenic Transforming Growth Factor-beta Signaling and Tumorigenesis in Mammary Tumors," FASEB Journal, 2009, vol. 23, No. 12, pp. 4231-4243.
Antonelli, A., et al., "CLM29, a multi-target pyrazolopyrimidine derivative, has anti-neoplastic activity in medullary thyroid cancer in vitro and in vivo," Molecular and Cellular Endocrinology, vol. 393, 2014, pp. 56-64.
Apsel, B., et al., "Targeted polypharmacology: Discovery of dual inhibitors of tyrosine and phosphoinositide kinases," Nat. Chem. Biol., vol. 4, No. 11, Nov. 2008, pp. 691-699.
Boyce, B.F., et al., "SRC inhibitors in metastatic bone disease," Clin. Cancer Res., vol. 12, Suppl. 20, Oct. 15, 2006, pp. 6291s-6295s.
Brunton, V.G., et al., "Src and focal adhesion kinase as therapeutic targets in cancer," Current Opinion in Pharmacology, vol. 8, 2008, pp. 427-432.
Carragher, N. O., et al., "Combining imaging and pathway profiling: an alternative approach to cancer drug discovery," Drug Discovery Today, vol. 17, No. 5/6, Mar. 2012, pp. 203-214.
Chaturvedi, D., et al., "Rapamycin induces transactivation of the EGFR and increases cell survival," Oncogene, vol. 28, 2009, pp. 1187-1196.
Chin, L., et al., "Translating insights from the cancer genome into clinical practice," Nature, vol. 452, Apr. 3, 2008, pp. 553-563.
Chislock, E. M., et al., "Abl kinases are required for vascular function, Tie2 expression, and angiopoietin-1-mediated survival," PNAS, vol. 110, No. 30, Jul. 23, 2013, pp. 12432-12437.
Cho, H.M., et al., "The Src/PLC/PKC/MEK/ERK signaling pathway is involved in aortic smooth muscle cell proliferation induced by glycated LDL," Molecules and Cells, vol. 19, No. 1, 2005, pp. 60-66.
Clavel, C.M., et al., "Thermoresponsive Chlorambucil Derivatives for Tumour Targeting, " Angew. Chem. Int. Ed., vol. 50, 2011, pp. 7124-7127.
Cohen, P., "Protein kinases—the major drug targets of the twenty-first century?," Nat. Rev. Drug. Discov., vol. 1, Apr. 2002, pp. 309-315.
Dar, A. C., et al., "Small molecule recognition of c-Src via the imatinib-binding conformation," Chemistry and Biology, vol. 15, Oct. 20, 2008, pp. 1015-1022.
Diner, P., et al., "Preparation of 3-substituted-1-isopropyl-1H-pyrazolo[3,4-d]pyrimidin-4-amines as RET kinase inhibitors," Journal of Medical Chemistry, vol. 55, 2012, pp. 4872-4876.
Duxbury, M.S., et al., "Inhibition of SRC tyrosine kinase impairs inherent and acquired gemcitabine resistance in human pancreatic adenocarcinoma cells," Clinical Cancer Research, vol. 10, Apr. 1, 2004, pp. 2307-2318.
Eder, J., et al., "The discovery of first-in-class drugs: origins and evolution," Nat. Rev. Drug Discov., vol. 13, Aug. 2014, pp. 577-587.
Frame, M.C., et al., "V-Src's hold over actin and cell adhesions," Nat. Rev. Mol. Cell Biol., vol. 3, No. 4, Apr. 2002, pp. 233-245.
Fujimoto, H., et al., "Regulation of the antioncogenic Chk2 kinase by the oncogenic Wip1 phosphatase," Cell Death and Differentiation, vol. 13, 2006, pp. 1170-1180.
Gallardo, V. E., et al., "Phenotype-driven chemical screening in zebrafish for compounds that inhibit collective cell migration identifies multiple pathways potentially involved in metastatic invasion," Disease Models and Mechanisms, vol. 8, 2015, pp. 565-576.
Gil-Henn, H. et al., "Arg/Abl2 promotes invasion and attenuates proliferation of breast cancer in vivo," Oncogene, vol. 32, 2013, pp. 2622-2630.
Girotti, M. R. et al., "Paradox-Breaking RAF Inhibitors that Also Target SRC Are Effective in Drug-Resistant BRAF Mutant Melanoma," Cancer Cell, vol. 27, No. 1, Jan. 12, 2015, pp. 85-96.
Greuber, E. K., et al., "Role of ABL family kinases in cancer: from leukaemia to solid tumours," Nat. Rev. Cancer, vol. 13, Aug. 2013, pp. 559-571.
Hanke, J. H., et al., "Discovery of a novel, potent, and Src family-selective tyrosine kinase inhibitor, Study of Lck- and FynT-dependent T cell activation," Journal of Biological Chemistry, vol. 271, No. 2, Jan. 12, 1996, pp. 695-701.
Hann, M. M., et al., "Finding the sweet spot: the role of nature and nurture in medicinal chemistry," Nat. Rev. Drug Discov., vol. 11, May 2012, pp. 355-365.
Hawthorne, V.S., et al., "ErbB2-mediated Src and signal transducer and activator of transcription 3 activation leads to transcriptional up-regulation of p21Cip1 and chemoresistance in breast cancer cells," Mol. Cancer Res., vol. 7, No. 4, Apr. 2009, pp. 592-600.
Holdgate, G., et al., "Biophysical Methods in Drug Discovery from Small Molecule to Pharmaceutical," Protein-Ligand Interactions: Methods and Applications, Methods in Molecular Biology, vol. 1008, Chapter 12, 2013, pp. 327-355.
Hsieh, A. C., et al., "The translational landscape of mTOR signalling steers cancer initiation and metastasis," Nature, vol. 485, May 3, 2012, pp. 55-61.
Hughes, J. P., et al., "Principles of early drug discovery," Br. J. Pharmacol., vol. 162, 2011, pp. 1239-1249.
Jester, B. W., et al., "Testing the promiscuity of commercial kinase inhibitors against the AGC kinase group using a split-luciferase screen," J. Med. Chem., vol. 55, 2012, pp. 1526-1537.
Kamb, A., et al., "Why is cancer drug discovery so difficult?," Nat. Rev. Drug Discov., vol. 6, Feb. 2007, pp. 115-120.

(56) References Cited

OTHER PUBLICATIONS

Kaufman, A.C., et al., "Fyn inhibition rescues established memory and synapse loss in Alzheimer mice," Ann. Neurol., vol. 77. No. 6, Jun. 2015, pp. 953-971.
Kerkela R., et al., "Cardiotoxicity of the cancer therapeutic agent imatinib mesylate," Nature Medicine, vol. 12, No. 8, Aug. 2006, pp. 908-916.
Knight, Z. A., et al., "Targeting the cancer kinome through polypharmacology," Nat. Rev. Cancer, vol. 10, Feb. 2010, pp. 130-137.
Knowles, P. P., et al., "Structure and chemical inhibition of the RET tyrosine kinase domain," Journal of Biological Chemistry, vol. 281, No. 44, Nov. 3, 2006, pp. 33577-33587.
Kola, I., et al., "Can the pharmaceutical industry reduce attrition rates?," Nat. Rev. Drug Discov., vol. 3, Aug. 2004, pp. 711-715.
Kopetz, S., et al., "Synergistic activity of the SRC family kinase inhibitor dasatinib and oxaliplatin in colon carcinoma cells is mediated by oxidative stress," Cancer Res., vol. 69, No. 9, May 1, 2009, pp. 3842-3849.
Lee, J. A., et al., "Modern phenotypic drug discovery is a viable, neoclassic pharma strategy," J. Med. Chem., vol. 55, 2012, pp. 4527-4538.
Liu, Y., et al., "Structural basis for selective inhibition of Src family kinases by PP1," Chemistry and Biology, vol. 6, No. 9,1999, pp. 671-678.
Lu, L., et al., "Hippo signaling is a potent in vivo growth and tumor suppressor pathway in the mammalian liver," Proc. Nat. Acad. Sci., vol. 107, No. 4, Jan. 26, 2010, pp. 1437-1442.
Liu, Y., et al., "Rational design of inhibitors that bind to inactive kinase conformations," Nature Chemical Biology, vol. 2, No. 7, Jul. 2006, pp. 358-364.
Mayer, E.L., et al., "Advances in targeting SRC in the treatment of breast cancer and other solid malignancies," Clinical Cancer Research, vol. 16, No. 14, Jul. 15, 2010, pp. 3526-3532.
Mccarthy, S.D.S., et al., "c-Src and Pyk2 protein tyrosine kinases play protective roles in early HIV-1 infection of CD4+ T-cell lines," J. Acquir. Immune Defic. Syndr., Jun. 1, 2014, vol. 66, No. 2, pp. 118-126.
Mcinnes, C., "Virtual screening strategies in drug discovery," Current Opinion in Chemical Biology, vol. 11, 2007, pp. 494-502.
Murrills, R. J., et al., "Osteogenic effects of a potent SRC-Over-ABL selective kinase inhibitor in the mouse," J. Pharmacol. Exp. Ther., vol. 340, 2012, pp. 676-687.
Myoui, A., et al., "C-SRC tyrosine kinase activity is associated with tumor colonization in bone and lung in an animal model of human breast cancer metastasis," Cancer Research, vol. 63, Aug. 15, 2003, pp. 5028-5033.
Noren, N. K., et al., "The Eph84 receptor suppresses breast cancer cell tumorigenicity through an Abl-Crk pathway," Nature Cell Biology, vol. 8, No. 8, Aug. 2006, pp. 815-825.
Nygaard, H.B., et al., "Fyn kinase inhibition as a novel therapy for Alzheimer's disease," Alzheimer's Research and Therapy, vol. 6, 2014, pp. 1-8.
Nygaard, H.B., et al., "A phase lb multiple ascending dose study of the safety, tolerability, and central nervous system availability of AZD0530 (saracatinib) in Alzheimer's disease," Alzheimer's Research and Therapy, vol. 7, 2015, pp. 1-11.
Park, G.B., et al., "The Epstein-Barr virus causes epithelial-mesenchymal transition in human corneal epithelial cells via Syk/src and Akt/Erk signaling pathways," Investigative Ophthamology and Visual Science, vol. 55, No. 3, Mar. 2014, pp. 1770-1779.
Patton, E. E., et al., "Spotlight on zebrafish: Translational impact," Disease Models and Mechanisms, vol. 7, 2014, pp. 731-733.
Qiu, Z., et al., "Abl family tyrosine kinases are essential for basement membrane integrity and cortical lamination in the cerebellum," Journal of Neuroscience, vol. 30, No. 43, Oct. 27, 2010, pp. 14430-14439.
Qiu, Z., et al., "c-Abl tyrosine kinase regulates cardiac growth and development," Proc. Nat. Acad. Sci., Jan. 19, 2010, vol. 107, No. 3, pp. 1136-1141.
Sassoon, L., et al., "Antibody-drug conjugate (ADC) clinical pipeline: a review," Antibody-Drug Conjugates, Methods in Molecular Biology, vol. 1045, Chapter 1, 2013, pp. 1-27.
Sawyers, C.L., et al., "The nuclear tyrosine kinase c-Abl negatively regulates cell growth," Cell, vol. 77, Apr. 8, 1994, pp. 121-131.
Schindler, T., et al., "Crystal structure of Hck in complex with a Src family-selective tyrosine kinase inhibitor," Molecular Cell, vol. 3, May 1999, pp. 639-648.
Smith, A., "Screening for drug discovery," Nature, vol. 418, Jul. 25, 2002, pp. 453-459.
Stommel, J. M., et al., "Coactivation of receptor tyrosine kinases affects the response of tumor cells to targeted therapies," Science, vol. 318, Sep. 13, 2007, pp. 287-290.
Summy, J.M., et al., "Src family kinases in tumor progression and metastasis," Cancer and Metastasis Reviews, vol. 22, No. 4, 2003, pp. 337-358.
Tatton, L., et al., "The Src-selective kinase inhibitor PP1 also inhibits Kit and Bcr-Abl tyrosine kinases," Journal of Biological Chemistry, vol. 278, No. 7, 2003, pp. 4847-4853.
Tyryshkin, A., et al., "SRC kinase is a novel therapeutic target in lymphangioleiomyomatosis," Cancer Research, vol. 74, No. 7, Apr. 1, 2014, pp. 1996-2005.
Velema, W. A., et al., "Photopharmacology: beyond proof of principle," Journal of American Chemical Society, vol. 136, 2014, pp. 2178-2191.
Versteegen, R. M., et al., "Click to Release: Instantaneous Doxorubicin Elimination upon Tetrazine Ligation," Angew. Chem. Int. Ed., vol. 52, 2013, pp. 14112-14116.
Vistoli, G., et al., "Assessing drug-likeness—what are we missing?," Drug Discovery Today, vol. 13, No. 7/8, Apr. 2008, pp. 285-294.
Walcher, D., et al., "C-Peptide induces vascular smooth muscle cell proliferation: involvement of SRC-kinase, phosphatidylinositol 3-kinase, and extracellular signal-regulated kinase 1/2," Circulation Research, vol. 99, Nov. 24, 2006, pp. 1181-1187.
Weiss, J. T., et al., "Development and Bioorthogonal Activation of Palladium-Labile Prodrugs of Gemcitabine," J. Med. Chem., vol. 57, 2014, pp. 5395-5404.
Weiss, J. T., et al., "Extracellular palladium-catalysed dealkylation of 5-fluoro-1-propargyl-uracil as a bioorthogonally activated prodrug approach," Nature Communications, vol. 5, 2014, pp. 3277-3285.
Wheeler, D.L., et al., "Epidermal growth factor receptor cooperates with Src family kinases in acquired resistance to cetuximab," Cancer Biol. Ther., vol. 8., No. 8, Apr. 2009, pp. 696-703.
Wilhelm, S., et al., "Discovery and development of sorafenib: a multikinase inhibitor for treating cancer," Nat. Rev. Drug Discov., vol. 5, Oct. 2006, pp. 835-844.
Xiao, T., et al., "A GFP-based genetic screen reveals mutations that disrupt the architecture of the zebrafish retinotectal projection," Development, vol. 132, No. 13, 2005, pp. 2955-2967.
Yang, K., et al., "Fyn, a potential target for Alzheimer's disease," Journal of Alzheimer's Disease, vol. 27, 2011, pp. 243-252.
Ma, H., et al., "The challenge of selecting protein kinase assays for lead discovery optimization," Expert Opin. Drug Discov., vol. 3, No. 6, Jun. 2008, pp. 607-621.
Yoo, S.K., et al., "Early redox, Src family kinase, and calcium signaling integrate wound responses and tissue regeneration in zebrafish," J. Cell Biol., vol. 199, No. 2, Oct. 8, 2012, pp. 225-234.
Zhang, S., et al., "Combating trastuzumab resistance by targeting SRC, a common node downstream of multiple resistance pathways," Nat. Med., vol. 17, No. 4, Apr. 2011, pp. 461-469.
Zhang, J., et al., "Targeting cancer with small molecule kinase inhibitors," Nat. Rev. Cancer, vol. 9, Jan. 2009, pp. 28-39.
Zhou, B. S., et al., "Targeting the checkpoint kinases: chemosensitization versus chemoprotection," Nat. Rev. Cancer, vol. 4, Mar. 2004, pp. 216-225.

\* cited by examiner

COMPOUNDS

The present invention relates to pyrazolopyrimidine compounds that are capable of inhibiting, more preferably, selectively inhibiting one or more tyrosine kinases. The compounds find applications in the treatment of a variety of disorders, including proliferative disorders such as cancer, bone, neurological, and viral disorders.

BACKGROUND TO THE INVENTION

Most drug discovery programs begin with a screening campaign (e.g. biochemical, virtual or biophysical) for agonists, antagonists or inhibitors of a nominated target associated to a particular disease [1-4]. After hit identification, subsequent chemical optimization is fundamentally based upon "on-target" potency [1]. Generation of so-called lead compounds (=high-affinity ligands) is followed by medicinal chemistry refinement into derivatives of superior potency and/or selectivity, and desirable pharmacokinetic properties (=druglikeness) [1, 5]. Selected drug candidates are then validated in vivo and, upon verified safety and efficacy, progressed to human trials [5]. This well-defined process, which typically consumes over a decade of research work and tens of millions of pounds on its path to the clinic, is finding a particularly low success rate in the development of anticancer drugs [6]. This is because, on top of the enormous difficulties of translating a drug discovery program from target identification—through preclinical and clinical development—into regulatory approval and marketing, it has become apparent that conventional approaches are not appropriately tailored to pathologies generated by the concurrent or sequential action of multiple etiologic factors such as cancer [6-8]. High attrition during late-stage drug development has underlined that elucidating cancer heterogeneity across patients and adaptive drug resistance mechanisms are the major obstacles to the development of effective targeted anticancer therapies [9-11]. These challenges are stimulating out-of-the-box thinking in pharmacotherapy research (e.g. targeted polypharmacology [10], antibody-drug conjugates [12], innovative prodrug approaches [13-17], etc.) and the reexamination of the core principles of drug discovery in oncology [18-20]. The rise of modern phenotypic drug discovery [18, 19] together with the use of clinically-relevant cancer models to guide early drug development [20], are representative examples of the paradigm shift initiated in the field to trigger a positive inflection point.

Protein kinases are integral components of intracellular signal transduction cascades. They govern a wide range of basic cellular functions and coordinate cell-to-cell and extracellular matrix (ECM)-to-cell communications to influence cell and tissue physiology. Thereby, kinases are directly involved in progressive diseases including cancer and inflammation [21]. Advances in the understanding of cancer cell biology along with the approval of several kinase inhibitors for cancer treatment have demonstrated the validity of a number of kinases as anticancer targets [22], while, on the contrary, other protein kinases have been shown to play an essential role in tumor suppressor pathways (anti-targets) [23-26].

The vast majority of kinase inhibitors target the kinase ATP pocket and because all kinases (>500) necessarily possess this relatively well-conserved catalytic site, there is a great potential for cross-reactivity [10]. In fact, even if most clinically-approved kinase inhibitors have been developed from a single target hypothesis, they typically display a broad selectivity profile which, in some cases, have resulted in unanticipated clinical applications (e.g. sorafenib) [26]. An inhibitor's promiscuity may also be advantageous for anticancer therapy when off-target activities assist to address bioactivity issues related to pathway redundancies, molecular heterogeneity or resistance mechanisms [9, 10, 26]. On the contrary, if these activities result in the inhibition of anti-oncogenic pathways or lead to severe side effects, drug promiscuity becomes a major drawback. Paradoxically, there is strong evidence indicating that some kinases may behave as a target or an antitarget depending of the cancer context. By way of illustration, the expression of the activated fusion oncoprotein Bcr-Abl is a genetic abnormality associated with chronic myeloid leukemia (CML) and Abl inhibitors (imatinib, dasatinib) are clinically used in chronic phase CML treatment [27]. In addition, Abl family kinases are abnormally activated in various solid tumors, supporting their involvement in oncogenesis [27]. However, Abl (Abl1) and Arg (Abl2) have been found to negatively modulate breast cancer progression in vivo [28-30], indicating that Abl inhibition could be counterproductive for its treatment (=breast cancer antitarget). This example serves to delineate the complexity of cancer etiology and highlights the necessity of developing kinase inhibitors with tailor-made pharmacodynamic profiles for the effective targeting of each cancer subtype. Unfortunately, despite the vast amount of small molecule inhibitors and biomedical knowledge built over the years, the limited understanding of cancer biology prevents the appropriate targeting of orchestrated actions that generate, maintain and progress most neoplastic processes.

Acknowledging these limitations, many research groups are frontloading the search of robust empirical data to progress anticancer drug development programs away from classical black-and-white anticancer hypotheses.

The present invention seeks to provide tyrosine kinase inhibitors having potent antiproliferative properties. The invention is founded on three hypotheses: (i) the use of phenotypic screening in designated models of cancer can be used to generate target-agnostic structure-bioactivity relationships and guide ligand optimization tailored to particular cancer types/subtypes; (ii) targeting the kinase ATP pocket with compounds derived from promiscuous kinase inhibitors can enable "rationally-biased" serendipitous discoveries; and (iii) early improvement of druglikeness on promiscuous ligands can be concurrently used to explore pharmacodynamic diversity. By means of this pragmatic approach to kinase inhibitor discovery, target deconvolution of identified hits and leads was largely facilitated, thereby enabling the rapid identification of the molecular targets and antitargets involved in the observed phenotype.

STATEMENT OF INVENTION

A first aspect of the invention relates to a compound of formula (I), or pharmaceutically acceptable salt thereof,

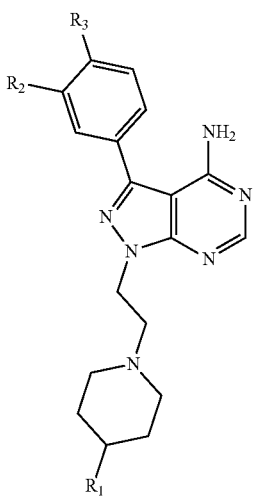

(I)

wherein:

$R_1$ is $(CH_2)_m NR_{11}R_{12}$;

$R_2$ is selected from H, halo, $OR_{13}$, $NHR_{13}$, alkyl, alkenyl and alkynyl;

$R_3$ is selected from alkyl, alkenyl, alkynyl, aryl, halo, aryloxy, $NHCO_2R_4$, $NHCONR_5R_6$, $NHCOR_7$, NH-alkyl, NH-alkenyl, $NH(CH_2)_n$-aryl, $(CH_2)_p$-heteroaryl, $(CH_2)_q CO_2R_8$, $(CH_2)_r COR_9$ and $NHSO_2R_{10}$, wherein each alkyl, alkenyl, aryl or heteroaryl moiety in the aforementioned list is optionally further substituted by one or more groups selected from alkyl, halo, OH, $NH_2$, alkoxy, aryloxy, alkylamino, arylamino, carboxyl and carboxamide;

$R_4$ to $R_{10}$ and $R_{13}$ are each independently selected from alkyl, alkenyl and aryl;

$R_{11}$ and $R_{12}$ are each independently selected from alkyl and alkenyl; or $R_{11}$ and $R_{12}$ are linked together with the nitrogen to which they are attached to form a heterocycloalkyl or heterocycloalkenyl group;

n, m, p, q and r are each independently selected from 0, 1, 2, 3, 4, 5 and 6.

A second aspect of the invention relates to a pharmaceutical composition comprising at least one compound as described above and a pharmaceutically acceptable carrier, diluent or excipient.

A third aspect of the invention relates to a compound as described above for use in medicine.

A fourth aspect of the invention relates to a compound as described above for use in treating a disorder selected from a proliferative disorder and a viral disorder.

A fifth aspect of the invention relates to the use of a compound as described above in the preparation of a medicament for treating or preventing a disorder selected from proliferative disorder, osteoporosis, Alzheimer's and Parkinson's disease and a viral disorder.

A seventh aspect of the invention relates to a method of treating a mammal having a disease state alleviated by inhibition, or preferably the selective inhibition, of a tyrosine kinase, wherein the method comprises administering to a mammal a therapeutically effective amount of a compound as described above.

An eighth aspect of the invention relates to the use of a compound as described above in an assay for identifying further candidate compounds capable of inhibiting, or selectively inhibiting, a tyrosine kinase.

A ninth aspect of the invention relates to a combination comprising a compound as described above and a second therapeutic agent.

A tenth aspect of the invention relates to a process for preparing compounds as described herein.

An eleventh aspect of the invention relates to a compound of formula (II), or a pharmaceutically acceptable salt thereof,

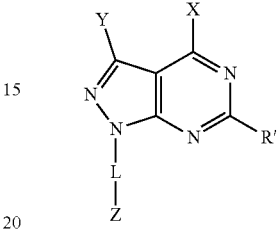

(II)

wherein:

X is selected from amino, alkylamino, arylamino, hydroxyl, alkoxy and aryloxy;

L is an alkylene linker group having from 1 to 6 carbon atoms, wherein said alkylene linker group is optionally substituted by one or more R" groups;

Z is a piperidinyl or piperazinyl group that is optionally substituted by one or more groups selected from R" and $(CH_2)_m NR_{11}R_{12}$;

Y is an aryl or heteroaryl group, wherein said aryl or heteroaryl group is optionally substituted by one or more groups selected from halo, $OR_{13}$, alkyl, aryl, alkenyl, alkynyl, $NHCO_2R_4$, $NHCONR_5R_6$, $NHCOR_7$, NH-alkyl, NH-alkenyl, $NH(CH_2)_n$-aryl, $(CH_2)_p$-heteroaryl, $(CH_2)_q CO_2R_8$, $(CH_2)_r COR_9$ and $NHSO_2R_{10}$, wherein each alkyl, alkenyl, aryl or heteroaryl moiety in the aforementioned list is optionally further substituted by one or more groups selected from alkyl, halo, OH, $NH_2$, alkoxy, aryloxy, alkylamino, arylamino, carboxyl and carboxamide;

R' is selected from H, alkyl, aryl, heteroaryl and halo, wherein said alkyl, aryl and heteroaryl groups may be optionally substituted by one or more R" groups;

$R_4$ to $R_{10}$ and $R_{13}$ are each independently selected from alkyl, alkenyl and aryl; and n, m, p, q and r are each independently selected from 0, 1, 2, 3, 4, 5 and 6; each R" is independently selected from alkyl, OH, alkoxy and halo;

$R_{11}$ and $R_{12}$ are each independently selected from alkyl and alkenyl; or $R_{11}$ and $R_{12}$ are linked together with the nitrogen to which they are attached to form a heterocycloalkyl or heterocycloalkenyl group;

for use in treating a disorder selected from Epstein Barr Virus, Alzheimer's disease and Dengue fever.

DETAILED DESCRIPTION

The present invention relates to pyrazolopyrimidine compounds that are capable of inhibiting, or more preferably selectively inhibiting, one or more kinases, preferably one or more tyrosine kinases, even more preferably Src-kinase. In particular, the invention relates to substituted pyrazolopyrimidine compounds having a specific substitution pattern.

"Alkyl" is defined herein as a straight-chain or branched alkyl radical, for example, methyl, ethyl, propyl, isopropyl, butyl, isobutyl, tert-butyl, pentyl, hexyl. Preferably, the alkyl group is a $C_{1-12}$-alkyl group, more preferably, a $C_{1-6}$-alkyl group, even more preferably a $C_{1-4}$-alkyl group.

"Alkenyl" is defined herein as a straight-chain or branched radical, containing one or more carbon-carbon double bonds. Preferably, the alkenyl group is a $C_{2-12}$-alkyl group, more preferably, a $C_{2-6}$-alkyl group, even more preferably a $C_{2-4}$-alkyl group.

"Alkynyl" is defined herein as a straight-chain or branched radical, containing one or more carbon-carbon triple bonds. Preferably, the alkynyl group is a $C_{2-12}$-alkyl group, more preferably, a $C_{2-6}$alkynyl group, even more preferably a $C_{2-4}$-alkynyl group.

"Cycloalkyl" is defined herein as a monocyclic alkyl ring, such as, cyclopropyl, cyclobutyl, cyclopentyl, cyclohexyl or cycloheptyl, or a fused bicyclic ring system such as bornane. Preferably, the cycloalkyl group is a $C_{3-8}$-cycloalkyl group, more preferably a $C_{3-6}$-cycloalkyl group.

"Cycloalkenyl" is defined herein as a cyclic group as defined above for cycloalkyl, but containing one or more carbon-carbon double bonds. Preferably, the cycloalkenyl group is a $C_{3-8}$-cycloalkenyl group, more preferably a $C_{3-6}$-cycloalkenyl group.

"Halogen" is defined herein as chloro, fluoro, bromo or iodo.

As used herein, the term "aryl" refers to a $C_{6-12}$ aromatic group, which may be benzocondensed, for example, phenyl or naphthyl.

"Heteroaryl" is defined herein as a monocyclic or bicyclic $C_{2-12}$ aromatic ring comprising one or more heteroatoms (that may be the same or different), such as oxygen, nitrogen or sulphur. Examples of suitable heteroaryl groups include thienyl, furanyl, pyrrolyl, pyridinyl, oxazolyl, thiazolyl, imidazolyl, pyrazolyl, isoxazolyl, isothiazolyl, oxadiazolyl, triazolyl, thiadiazolyl etc. and benzo derivatives thereof, such as benzofuranyl, benzothienyl, benzimidazolyl, indolyl, isoindolyl, indazolyl etc.; or pyridyl, pyrazinyl, pyrimidinyl, pyridazinyl, triazinyl etc. and benzo derivatives thereof, such as quinolinyl, isoquinolinyl, cinnolinyl, phthalazinyl, quinazolinyl, quinoxalinyl, naphthyridinyl etc.

In one preferred embodiment n, m, p, q and r are each independently selected from 0, 1, 2 and 3.

In one preferred embodiment, $R_{11}$ and $R_{12}$ are alkyl.

In one preferred embodiment, m is 0.

In another preferred embodiment, m is 1.

In another preferred embodiment, $R_{11}$ and $R_{12}$ are linked together with the nitrogen to which they are attached to form a heterocycloalkyl group. Preferably, for this embodiment, m is 0.

Preferably, $R_{11}$ and $R_{12}$ are linked together with the nitrogen to which they are attached to form a 6-membered heterocycloalkyl group or a 5-membered heterocycloalkyl group.

In a more preferred embodiment, $R_1$ is selected from $NMe_2$, $CH_2NMe_2$, pyrrolidin-1-yl and piperidin-1-yl.

In one preferred embodiment, $R_2$ is selected from H and alkoxy, more preferably, H and OMe.

In one preferred embodiment, $R_3$ is selected from alkyl, $NHCO_2R_4$, $NHCOR_7$, $NH(CH_2)_n$-aryl, $NHCONR_5R_6$, $(CH_2)_p$-heteroaryl and $(CH_2)_qCO_2R_8$.

In one preferred embodiment, $R_4$ to $R_{10}$ are each independently alkyl.

In one preferred embodiment, R is selected from Me, $NHCO_2$-alkyl, NHCO-alkyl, $NH(CH_2)_n$-aryl, NHCONH-alkyl, $(CH_2)_p$-heteroaryl and $(CH_2)_qCO_2$-alkyl.

In one preferred embodiment, each of n, p, q and r is 1.

In one preferred embodiment, $R_3$ is selected from Me, $NHCO_2$-$^tBu$, $NHCOCH_2C(Me)_3$, $NHCH_2$phenyl, NHCONH-$^tBu$, $CH_2$-(4-methyl-oxazol-2-yl) and $CH_2CO_2$-$^tBu$.

In one preferred embodiment, $R_3$ is selected from Me and $NHCO_2$-$^tBu$.

In one preferred embodiment, $R_3$ is Me and $R_2$ is H.

In one preferred embodiment, $R_2$ is alkoxy, and $R_3$ is selected from $NHCO_2R_4$, $NHCOR_7$, $NH(CH_2)_n$-aryl, $NHCONR_5R_6$, $(CH_2)_p$-heteroaryl and $(CH_2)_qCO_2R_8$.

In one preferred embodiment, $R_2$ is OMe and $R_3$ is selected from $NHCO_2$-$^tBu$, $NHCOCH_2C(Me)_3$, $NHCH_2$phenyl, NHCONH-$^tBu$, $CH_2$-(4-methyl-oxazol-2-yl) and $CH_2CO_2$-$^tBu$.

In one highly preferred embodiment of the invention the compound of formula I is selected from the following:

| Compound No: | Structure |
| --- | --- |
| 109 | 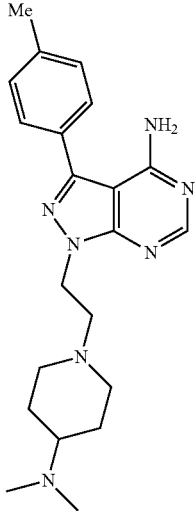 [SMILES: Cc1ccc(-c2nn(CCN3CCC(N(C)C)CC3)c3ncnc(N)c23)cc1] |
| 105 | 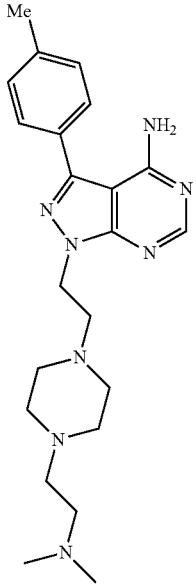 [SMILES: Cc1ccc(-c2nn(CCN3CCN(CCN(C)C)CC3)c3ncnc(N)c23)cc1] |

| Compound No: | Structure |
|---|---|
| 112 | (4-methylphenyl substituted pyrazolo[3,4-d]pyrimidin-4-amine with N-ethyl-[4-((dimethylamino)methyl)piperidin-1-yl] side chain) |
| 503 | (tert-butyl carbamate of 2-methoxy-4-substituted phenyl pyrazolo[3,4-d]pyrimidin-4-amine with N-ethyl-[4-((dimethylamino)methyl)piperidin-1-yl] side chain) |
| 506 | (tert-butyl carbamate of 2-methoxy-4-substituted phenyl pyrazolo[3,4-d]pyrimidin-4-amine with N-ethyl-[4-(dimethylamino)piperidin-1-yl] side chain) |
| 518 | (tert-butyl carbamate of 2-methoxy-4-substituted phenyl pyrazolo[3,4-d]pyrimidin-4-amine with N-ethyl-[4-(pyrrolidin-1-yl)piperidin-1-yl] side chain) |

| Compound No: | Structure |
|---|---|
| 519 | 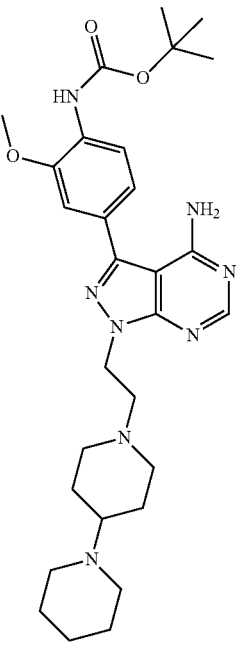 [SMILES: COc1cc(-c2nn(CCN3CCC(N4CCCCC4)CC3)c3ncnc(N)c23)ccc1NC(=O)OC(C)(C)C] |
| 526 | 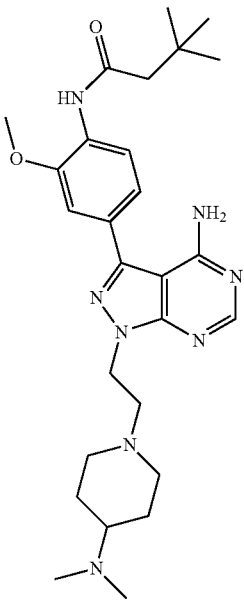 [SMILES: COc1cc(-c2nn(CCN3CCC(N(C)C)CC3)c3ncnc(N)c23)ccc1NC(=O)CC(C)(C)C] |
| Compound No: | Structure |
|---|---|
| 533 | 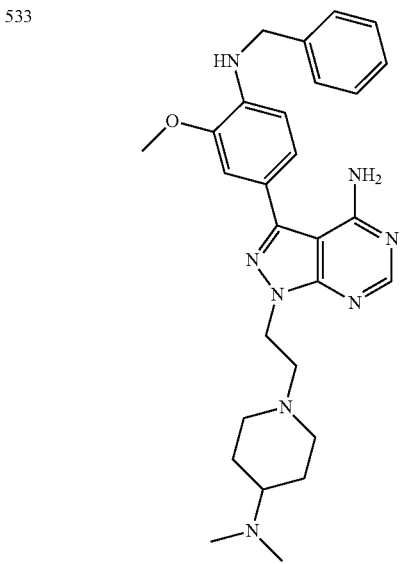 |
| 540 | 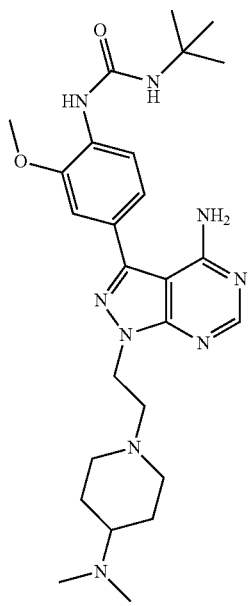 [SMILES: COc1cc(-c2nn(CCN3CCC(N(C)C)CC3)c3ncnc(N)c23)ccc1NC(=O)NC(C)(C)C] |

| Compound No: | Structure |
|---|---|
| 543 | 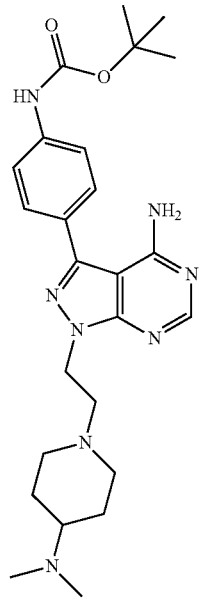 [SMILES: CN(C)C1CCN(CCn2nc(-c3ccc(NC(=O)OC(C)(C)C)cc3)c3c(N)ncnc32)CC1] |
| 553 | 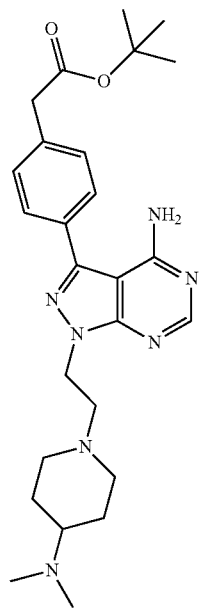 [SMILES: CN(C)C1CCN(CCn2nc(-c3ccc(CC(=O)OC(C)(C)C)cc3)c3c(N)ncnc32)CC1] |

| Compound No: | Structure |
|---|---|
| 565 | 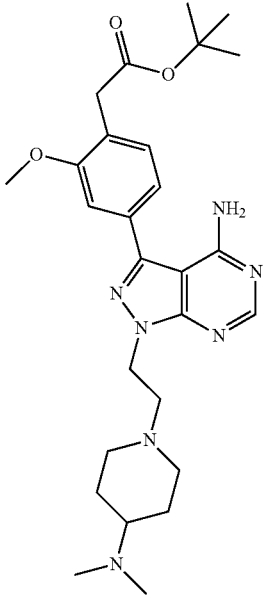 [SMILES: COc1cc(-c2nn(CCN3CCC(N(C)C)CC3)c3ncnc(N)c23)ccc1CC(=O)OC(C)(C)C] |
| 584 | 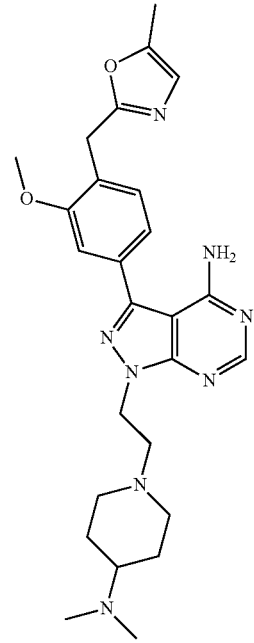 [SMILES: COc1cc(-c2nn(CCN3CCC(N(C)C)CC3)c3ncnc(N)c23)ccc1Cc1ncc(C)o1] | and pharmaceutically acceptable salts thereof.

In one highly preferred embodiment, the compound is selected from compounds 506, 518, 519, 533, 553 and 565.

In another highly preferred embodiment, the compound is selected from compounds 506 and 565.

Compounds of Formula (II)

Another aspect of the invention relates to a compound of formula (II), or a pharmaceutically acceptable salt thereof,

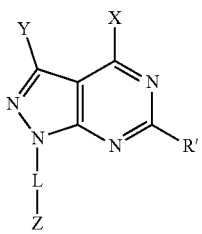

(II)

wherein:

X is selected from amino, alkylamino, arylamino, hydroxyl, alkoxy and aryloxy;

L is an alkylene linker group having from 1 to 6 carbon atoms, wherein said alkylene linker group is optionally substituted by one or more R" groups;

Z is a piperidinyl or piperazinyl group that is optionally substituted by one or more groups selected from R" and $(CH_2)_mNR_{11}R_{12}$;

Y is an aryl or heteroaryl group, wherein said aryl or heteroaryl group is optionally substituted by one or more groups selected from halo, $OR_{13}$, alkyl, aryl, alkenyl, alkynyl, $NHCO_2R_4$, $NHCONR_5R_6$, $NHCOR_7$, NH-alkyl, NH-alkenyl, $NH(CH_2)_n$-aryl, $(CH_2)_p$-heteroaryl, $(CH_2)_qCO_2R_8$, $(CH_2)_rCOR_9$ and $NHSO_2R_{10}$, wherein each alkyl, alkenyl, aryl or heteroaryl moiety in the aforementioned list is optionally further substituted by one or more groups selected from alkyl, halo, OH, $NH_2$, alkoxy, aryloxy, alkylamino, arylamino, carboxyl and carboxamide;

R' is selected from H, alkyl, aryl, heteroaryl and halo, wherein said alkyl, aryl and heteroaryl groups may be optionally substituted by one or more R" groups;

$R_4$ to $R_{10}$ and $R_{13}$ are each independently selected from alkyl, alkenyl and aryl; and n, m, p, q and r are each independently selected from 0, 1, 2, 3, 4, 5 and 6; each R" is independently selected from alkyl, OH, alkoxy and halo;

$R_{11}$ and $R_{12}$ are each independently selected from alkyl and alkenyl; or $R_{11}$ and $R_{12}$ are linked together with the nitrogen to which they are attached to form a heterocycloalkyl or heterocycloalkenyl group;

for use in treating a disorder selected from Epstein Barr Virus, Alzheimer's disease and Dengue fever.

In one preferred embodiment, L is a $C_2$-$C_4$ alkylene linker, which may be substituted or unsubstituted.

In a more preferred embodiment, L is an ethylene linker, which may be substituted or unsubstituted.

In one preferred embodiment, X is selected from amino, alkylamino and arylamino. More preferably, X is amino.

In one preferred embodiment, R' is selected from H and alkyl. More preferably, R' is H.

In one preferred embodiment, Z is a piperidin-1-yl or piperazin-1-yl group that is optionally substituted by one or more groups selected from R" and $(CH_2)_mNR_{11}R_{12}$.

In a more preferred embodiment, Z is a piperidin-1-yl group that is optionally substituted by one or more groups selected from R" and $(CH_2)_mNR_{11}R_{12}$.

In a more preferred embodiment, Z is a piperidin-1-yl group that is substituted by one or more $(CH_2)_mNR_{11}R_{12}$ groups. More preferably, Z is a piperidin-1-yl group that is substituted in the 4-position by a group selected from dialkylamino, cycloalkylamino and dialkylaminoalkyl.

In one preferred embodiment, Y is an optionally substituted aryl group, more preferably, an optionally substituted phenyl group.

In a preferred embodiment, Y is a phenyl group optionally substituted in the 3-position with a group selected from halo, alkoxy, aryloxy, alkylamino and alkyl.

In a preferred embodiment, Y is a phenyl group optionally substituted in the 4-position with a group selected from alkyl, aryl, halo, aryloxy, alkylamino, arylamino, $NHCO_2R_4$, $NHCONR_5R_6$, $NHCOR_7$, NH-alkyl, $NH(CH_2)_n$-aryl, $(CH_2)_p$-heteroaryl, $(CH_2)_qCO_2R_8$, $(CH_2)_rCOR_9$ and $NHSO_2R_{10}$, wherein each instance of alkyl, aryl or heteroaryl in the aforementioned list is optionally further substituted by one or more groups selected from alkyl, halo, OH and $NH_2$.

More preferably still, Y is a phenyl group substituted in the 3-position with a group selected from halo, alkoxy, aryloxy, alkylamino and alkyl, and substituted in the 4-position by a group selected from alkyl, aryl, halo, aryloxy, alkylamino, arylamino, $NHCO_2R_4$, $NHCONR_5R_6$, $NHCOR_7$, NH-alkyl, $NH(CH_2)_n$-aryl, $(CH_2)_p$-heteroaryl, $(CH_2)_qCO_2R_8$, $(CH_2)_rCOR_9$ and $NHSO_2R_{10}$, wherein each instance of alkyl, aryl or heteroaryl in the aforementioned list is optionally further substituted by one or more groups selected from alkyl, halo, OH and $NH_2$.

Highly preferred embodiments are as described above for compounds of formula (I).

Design, Synthesis and Screening of Novel Pyrazolopyrimidines

In the search for inhibitors that could potentially target a wide range of kinases with relevance in cancer, a ligand-based drug development program was conducted using the multikinase inhibitor PP1 as the core structure (FIG. 1). PP1 indiscriminately targets tyrosine protein kinases, many of which are involved in oncogenesis such as Src family kinases (SFK), Ret, Kit and Abl [31-34]. Moreover, related derivatives developed thereafter [35, 36] have shown strong inhibition against other groups of kinases with relevance in cancer including VEGFRs, PDGFRs, PI3Ks and mTOR. According to the co-crystal structure of PP1 with Hck [37] and Ret [38] kinases, this small molecule is an archetypical type I kinase inhibitor [39, 40], with its N5 and 4-$NH_2$ groups forming multiple hydrogen bonds with the hinge region of the kinase catalytic site [39-41]. The C3 p-tolyl group is located in a hydrophobic region well-conserved across most tyrosine kinases, thus being responsible for the partial selectivity of the inhibitor over other families of kinases. Although PP1's potent inhibition of disease-associated kinases (e.g. SFK, Ret, etc.) make it a valuable tool for biological studies, its clinical use is limited by very low solubility in water and poor selectivity, major limiting factors for the clinical translation of many drug candidates [42].

The substitution of PP1's tert-butyl group at the N1 position with flexible water-solubilizing groups can be used to both improve its drug-like properties and explore the accessible sugar/phosphate regions occupied by the natural ligand ATP (FIG. 1) in the search for novel binding affinity profiles. As shown in the lower panel of FIG. 1, compounds were designed to display a cyclic tertiary amine connected to the N1 position of the pyrazolopyrimidine ring through an ethylene linker (see general synthesis in FIG. 2). Following this synthetic procedure, structural diversity was readily implemented by coupling a selection of cyclic secondary amines to the corresponding aldehyde derivative via reductive amination.

Several investigations have reported that substitution of the p-tolyl group at the C3 position of PP1 by substituted aryl moieties (even closely related ones) significantly impact on protein-ligand binding. Medicinal chemistry campaigns on that position has generated inhibitors for a wide range of kinases, including receptor and non-receptor tyrosine kinases (e.g. c-Src, Ret, PDGFRs, VEGFRs, c-Kit and Abl) [31-35] and non-tyrosine kinases (e.g. PI3Ks and mTOR) [36, 43]. To expand the prospective pharmacodynamic scope of the novel compounds, alongside the modifications implemented on the N3 position, a broad selection of aryl boronic acids were employed to functionalize the C3 position of the pyrazolopyrimidine ring by palladium-catalyzed cross-coupling chemistry.

The human breast adenocarcinoma cell line MCF7 was selected as a cell-based model and phenotypic screening used to evaluate the novel compounds and classify hits against different antioncogenic activities. Highly-discriminate cell-based assays do not only allow the identification of compounds that target proteins involved in MCF7 cell growth, migration and survival but also exclude chemicals with low cell penetrability (and therefore deficient drug-likeness). Searching for antiproliferative properties as the primary output, $EC_{50}$ values in MCF7 cells were calculated for the novel compounds using a 10-point half-log dose response study (100 µM to 0.01 µM). Cell viability was determined at day 5 using PrestoBlue® reagent. Spectrofluorometry analyses were carried out in an Envision® plate reader.

Among all the structures synthesized and tested (see Tables of activities 1 and 2), the introduction of a 4-(N-Boc-amino)-3-methoxyphenyl at the C3 position was one of the most successful (FIG. 3a). On the other hand the presence of dimethylamino-containing piperidinyl groups at the position N1 were found optimal for the antiproliferative potency of the compounds, with the dimethylamino-piperidinylethyl group being the best moiety found. Antiproliferative properties of compounds 503 and 506 were tested in cells using dasatinib as positive control. Dasatinib is a potent inhibitor of both Abl and Src, is currently used in the treatment of chronic phase CML and is in several clinical trials for different types of cancer including breast cancer. Together with MCF7 cells, triple negative breast cancer MDA-MB-231 cells were tested alongside to explore the antiproliferative potency of the compounds against different breast cancer subtypes. As shown in FIG. 3b, compound 506 displayed a superior antiproliferative effect to compound 503 over both MCF7 and MDA-MB-231 breast cancer cells. Remarkably, compound 506 also outperformed the gold-standard Src inhibitor dasatinib in both cell lines.

To identify the target/s that could be responsible of the phenotype induced by lead compound 506 in MCF7 cells, $IC_{50}$ values were determined against a selection of human protein kinases involved in cancer. The recombinant proteins of the assay were chosen in accordance with the kinase profile of related pyrazolopyrimidines found on the literature [31-36]. As shown in Table 3 (note that values are expressed in nM), both compounds 503 and 506 possessed sub-nano molar potency against Src and Yes (proto-oncogenes that play a critical role in signal transduction pathways involved in tumor growth, angiogenesis, invasion, and dissemination) [30] with compound 506 having an improved selectivity over Abl (>950 fold difference in potency). Pharmacologically speaking this is very noteworthy since evidence in the literature strongly suggests that Abl inhibition could be counterproductive for the treatment of some types of breast cancer [28-30] and Abl inhibition has also been associated with cardiotoxicity [44]. Importantly, this unique selectivity profile differentiates the compounds of the invention from compound PP20 (FIG. 3a) [35], which is a known unspecific Abl/Src kinase inhibitor displaying subnanomolar potency for both Abl and Src. Without wishing to be bound by theory, introduction of the polyamine moiety at N1 position of the pyrazolopyrimidines is believed to play a part in the unprecedented selectivity profile of these derivatives.

To further assess the selectivity profile shown by compounds 506 and 503 on a non-cancerous cell model, dose response studies were carried out in murine SYF fibroblasts (which cells deficient for Src, Yes, and Fyn) with compound 506, 503 and dasatinib. Cell viability determined at day 5 using PrestoBlue® reagent and analyzed by spectrofluorometry (FIG. 3c). Remarkably, compounds 506 and 503 showed much lower antiproliferative activity than dasatinib in SYF cells, indicating that the novel compounds are more selective than dasatinib and might lead to reduced side effect caused by off-target activities.

Modifications of compound 506 led to a number of derivatives with similar properties (Table 1) and many compounds with low selectivity and/or antiproliferative activity (Table 2).

Highly Selective Src Kinase Inhibitors

Src is a non-receptor tyrosine kinase and the most widely studied member of the Src family kinases (SFKs), which include Lyn, Fyn, Lck, Hock, Fgr, Blk, Frk and Yes. Upregulated Src expression and/or activity has been reported in many tumour types, but is best described in colon and breast cancer where Src activity correlates with malignancy potential and poor clinical prognosis [47, 49].

Acquired drug resistance to numerous anticancer agents including cetuximab, oxaliplatin, gemcitabine, rapamycin, taxanes and B-RAF inhibitors has been associated with dysregulated Src signaling [65, 57, 54, 48, 56, 50]. These studies indicate that Src activity represents a common drug resistance mechanism and targeted inhibition of Src may sensitize resistant tumours to a number of therapeutic interventions or provide an alternate treatment option in late stage relapsed disease. For example, Src activity has also been identified as a common signalling mechanism in trastuzumab resistance, indicating that Src inhibitors may provide an alternative treatment for trastuzumab-resistant breast tumours [66].

The strong disease linkage and correlation between Src activity with poor cancer prognosis, morbidity and acquired resistance to existing therapy all support the premise that Src represents an important anti-cancer therapeutic target. Several Src inhibitors (Dasatanib, Bosutinib, Saracatinib, AZD0424) have entered the clinic and a number of Phase I/II trials are underway across distinct cancer indications [58, 49]. However, clinical outcome data published to date has not been compelling and the unresolved challenge is identifying which patients are most likely to benefit from targeted Src inhibition and which are the most appropriate clinical settings to demonstrate efficacy, e.g advanced disease endpoints or combination with existing agents or rationally designed novel combination therapies.

All current Src kinase inhibitors (Dasatanib, Bosutinib, Saracatinib, AZD0424) represent non-selective tyrosine kinase inhibitors with significant off-target activities contributing to adverse events and dose-limiting toxicities. All existing Src inhibitors also demonstrate potent activity against Abl1 (Abelson murine leukemia viral oncogene homolog 1) a cytoplasmic and nuclear protein tyrosine kinase. The t(9;22) translocation results in the head-to-tail fusion of the BCR and ABL1 genes, leading to a constitutively-active fusion gene present in many cases of chronic myelogenous leukemia, which are successfully treated with BCR-Abl1 inhibitors.

The off-target activities of known Src inhibitors were neither selected or optimized by rational design and may limit their use in advanced cancer disease setting as combination therapy, where unnecessary off-target activity contributes to dose-limiting and combination-limiting toxicity. Evidence exists indicating that therapeutic targeting of Abl may have detrimental effects on cardiotoxicity [51, 56] and non-tumourigenic tissue through its dual function as a tumour suppressor, thus potentially contributing to neoplasia [64, 62, 45, 55]. Furthermore, evidence suggests that targeting Abl contributes to osteopenia [60]. Thus, current non-selective dual Src/Abl inhibitors are not appropriate for long-term application in both cancer and non-cancer (e.g. osteoporosis or virus infection) indications.

A phenotypic screening strategy was employed in order to identify and optimise novel and highly potent c-Src kinase inhibitors with improved target selectivity profiles compared with existing Src inhibitors on the market. Phenotypic screening strategy favours the discovery of small molecules with optimal biophysical properties. Using this method, pyrazolopyrimidines with potent antiproliferative activities were found. Unexpectedly, after target identification, it was demonstrated that the presently claimed compounds (including, e.g. compounds 506, 518, 519, 533, 553 and 565) are the only highly potent c-Src kinase inhibitors reported to date that do not target Abl but exert anti-proliferative, anti-migratory and cytotoxic properties upon cancer cells in vitro with comparable potency to existing non-selective Src inhibitors (Tables 4 and 5).

In summary, all of the Src kinase inhibitors under current clinical development are not appropriately tailored to the optimal use of a Src inhibitor as drug combination therapy in advanced disease settings or in the chronic treatment of non-cancerous disease indications as a result of significant off-target activity, including adverse inhibition of Abl1. The presently claimed compounds are the first selective Src kinase inhibitors reported that do not inhibit Abl1. For example, compounds 506 and 565, which are highly preferred, are superior to existing Src inhibitors for use in the advanced cancer disease setting as a combination therapy.

As shown in Table 5 and FIG. 4, the novel Src inhibitors are specific for the "Src family" kinases over other members of the broader kinome family. The Src family is composed of several closely related homologues (e.g. Lyn, Fyn, Lck, Hck, Fgr, Blk, Frk and Yes). The homologues are highly conserved and it would be extremely difficult to selectively target distinct family members by small-molecules. In contrast to all of the Src inhibitors published to date, and in the clinic, the presently claimed compounds are the only molecules that specifically target Src family members at low/sub-nanomolar potency and not other kinases including Abl. Full kinome panel screening data for the compound 506 supports this claim (see FIG. 4).

Analysis of the solubility properties found that the presently claimed compounds possess good solubility in PBS (>100 mg/mL). In addition, they show good stability in the presence of liver microsomes and plasma binding at the level of 81-91% (see Table 6).

hERG channel inhibition was studied for selected compounds of the invention. A Life Technologies fluorescence-based kit (Predictor) hERG Fluorescence Polarization Assay Kit) was used. All of the compounds showed $IC_{50}$>10 µM. The most potent of the series was compound 533 with $IC_{50}$ (10-15 µM). A second hERG Safety Assay utilizing the Ionworks™ high-throughput electrophysiology screen for selected compounds of the invention was also performed, along with plasma stability analysis (mouse, rat and human).

The results are shown in Table 7. These experiments corroborated the safety of the compounds. Plasma stability studies demonstrate the high stability of the compounds in human plasma.

In vivo PK (iv and po) were subsequently studied in female mice for compounds 506 and 565. Blood and plasma levels were studied for 8 hours and the compounds showed no toxic effects. Oral administration demonstrated that the compounds are orally available. While 506 displayed moderate oral bioavailability, 565 showed excellent oral bioavailability (52%). The half-life of compound 506 was superior than for compound 565.

As observed in Table 8, CYP P450 inhibition was shown to be residual. Given the potency of the compounds, anything less than 50% inhibition at concentrations above 10 µM is not considered to be significant.

PD studies were done in vitro with MDA-MB-231 cells, which showed strong inhibition of phospho-Src at low nanoM concentration (see FIG. 5 below).

To test whether inhibition of Abl could influence the phenotypic effect mediated by the compounds, combination studies were performed with compound 506 and the specific Abl allosteric inhibitor GNF-2. As shown in FIG. 6, titration of the Abl inhibitor antagonizes activity of the compound on cancer cell viability in vitro. A lack of clinical efficacy is observed with existing Src inhibitors when used as monotherapy in cancer, thus for some time it has been argued that Src inhibitors must be used in combination therapy. It is believed that the absence of detrimental off-target activity including Abl activity (unique to the presently claimed compounds) will enhance both efficacy and minimize adverse events resulting from off-target activity.

Src family kinases are well known to have active roles in cell migration and invasion and are involved metastasis in cancer patients [67, 68]. To test whether compound 506 could inhibit cell migration in vitro, a scratch wound assay was set up using the Incucyte Zoom system. Cells were imaged across 30 minute intervals over 24 hours.

The migration of MDA-MB-231 cells was inhibited as early as 6 hours into the study and potency retained until the end of the assay, 24 hours (see FIG. 7). Compound 506 showed comparable results to Dasatinib.

As a toxicity study and phenotypic in vivo study, a zebrafish tail regeneration assay was performed [69]. As demonstrated by Yoo and coworkers [69], the action of Src family kinases (in particular Fynb, similar to human Fyn) is required for regeneration of amputated fins. This was used to assess and compare the in vivo activity of compound 506 and Dasatinib. As shown in FIG. 8, compound 506 and dasatinib inhibited regeneration of the tail fin. However, compound 506 did not show any other phenotypic or toxic effect on the embryo, while Dasatinib clearly induced cardiotoxicity (a well-established dose-limiting side effect of Abl inhibitors including Dasatinib).

Phenotypic Screening of SRC Inhibitor 506 in Zebrafish

Developing zebrafish provides a rapid phenotypic assay to simultaneously test safety and efficacy of novel compounds in a living vertebrate [78]. Small molecule phenotypic based screens in zebrafish have recently implicated SRC kinase in the migration of the posterior lateral line primordium [79], a cohesive cluster of cells that migrates horizontally under the skin along the myoseptum to the end of the tail, periodically depositing neuromasts. To determine the effects of 506 on cell migration in vivo, we treated Tg(bm3c: mGFP) transgenic zebrafish [80] that express green fluorescent protein (GFP) in the mechanosensory hair cells of the lateral line (which form part of the neuromasts) with 506 and dasatinib for 2 d and measured the distance of the last neuromast to the tip of the tail (marked by the end of the notochord and the presence of black melanocytes, FIG. 9a, vertical dashed line). 506 significantly reduced neuroblast migration (>100 microns in average) with minimal effect on the development of the embryos (FIG. 9a-c). In contrast, dasatinib treatment at >10 µM resulted in severe cardiotoxicity and death of most embryos. At concentrations that were compatible with embryo survival (1-10 µM), dasatinib did not inhibit the migration of neuroblasts whereas it did still induce a patent cardiotoxic phenotype (note heart enlargement in FIG. 9c). Further safety studies showed that dual ABL/SRC inhibitor PP20 also induces severe cardiotoxicity in zebrafish even after short treatment. These results, which correlates with the essential role of ABL in heart development and healing [81], [82], suggests that the selectivity of 506 over ABL might be advantageous for therapy when ABL inhibition is not required.

In Vivo SRC Inhibition Study in a Tumor Xenograft Model

The presence of active (phosphorylated) SRC in human colorectal cancer HCT116 cells and its inhibition under 506 treatment was verified by western blot. Subsequently, an in vivo PD study was performed in a xenograft model of HCT116 cells in mice [83]. HCT116 cells were injected subcutaneously and tumors allowed to grow up to 3-4 mm in diameter. Subsequently, mice were dosed daily for 3 d with 506 (50 mg/kg, in nanopure water) or vehicle (nanopure water) by oral gavage and culled 3 h after the last dose (n=4). Tumors were excised, fixed and sections labelled for phospho-SRC$^{Y416}$ and stained with hematoxylin. As shown in FIG. 10, microscopy analysis demonstrated significant reduction of phospho-SRC$^{Y416}$ in the xenograft sections from mice treated with 506 relative to the untreated animal controls.

Therapeutic Applications

A further aspect of the invention relates to a compound as described above for use in medicine.

Another aspect of the invention relates to a compound as described above for use in treating a disorder selected from a proliferative disorder, a viral disorder, neurological disorders and osteoporosis.

In one preferred embodiment, the proliferative disorder is cancer. Preferably, the cancer is selected from solid cancers at any stage. Preferably, the cancer is in a late-stage, with metastatic lesions.

Preferably, the primary cancer is selected from breast cancer, colon cancer, prostate melanoma, bladder, pancreatic, head and neck and ovarian cancer, with or without metastasis, and haematological cancers such as acute myeloid leukemia (AML), chronic lymphocytic leukemia (CLL), acute lymphocytic leukemia (ALL), multiple myeloma (MM) and non-Hodgkins lymphoma.

Particularly preferred primary cancer disease indications include, but are not limited to: triple negative breast cancer, Trastuzumab and/or Lapatinib resistant Her2 positive breast cancer, advanced melanoma including Vemurafenib resistant disease and multiple myeloma.

In one preferred embodiment, the proliferative disorder is Lymphangioleiomyomatosis (LAM), a progressive lung disease in which atypical cells, originating somewhere in the body, spread throughout the lungs, gradually blocking small airways and producing cysts. Typically, the disease progresses slowly, but eventually it can restrict breathing to cause death. Currently there is no proven cure for LAM. Src kinase is active in LAM cells and is important for cell growth and cells' ability to move around and invade the lung tissue [70]. Clinical trials to investigate the tolerability of saracatinib in Lam patients is currently in progress.

In one preferred embodiment, the proliferative disorder is atherosclerosis and restenosis characterized by migration and hyperproliferation of vascular smooth muscle cells. Src Kinase signalling has previously been implicated in aortic smooth muscle cell proliferation induced by clinical risk factors detected in the circulation; C-peptide and glycated LDL [71, 72].

The compounds described here are also suitable for chronic administration in several non cancer disease indications such as osteoporosis, Parkinson's disease, Alzheimer's disease and dengue virus infection.

In one preferred embodiment, the disorder is osteoporosis or bone metastasis. Src activity is implicated in metastatic bone disease, which represents the primary metastatic site for patients with breast cancer. The structural integrity and normal functions of the bone are governed by the carefully controlled balance of bone resorption mediated by osteoclast cells and bone production mediated by osteoblasts. Src activity plays a key role in both osteoclast function and tumour colonization of the bone [61]. Thus, targeted inhibition of Src activity can induce net bone formation [46] and alleviate the significant morbidity associated with metastatic bone disease and potentially osteoporosis.

In one particularly preferred embodiment, the viral disorder is Epstein Barr Virus. The Epstein-Barr virus (EBV), also called human herpesvirus 4 (HHV-4), is one of eight viruses in the herpes family, and is one of the most common viruses in humans. It is best known as the cause of infectious mononucleosis (glandular fever). It is also associated with particular forms of cancer, such as Hodgkin's lymphoma, Burkitt's lymphoma, nasopharyngeal carcinoma, and conditions associated with human immunodeficiency virus (HIV), such as hairy leukoplakia and central nervous system lymphomas. There is evidence that infection with EBV is associated with a higher risk of certain autoimmune diseases, especially dermatomyositis, systemic lupus erythematosus, rheumatoid arthritis, Sjögren's syndrome and multiple sclerosis. Some 200,000 cancer cases per year are thought to be attributable to EBV. EBV infects B cells of the immune system and epithelial cells. Once EBV's initial lytic infection is brought under control, EBV latently persists in the individual's B cells for the rest of the individuals life.

In one particularly preferred embodiment, the viral disorder is Dengue Virus infection. Dengue fever cases have increased dramatically over the last 4 decades with between 50 and 528 million people infected yearly. Symptoms include, sudden high fever, severe headaches, pain behind the eyes, severe joint and muscle pain, nausea, vomiting, skin rash, mild bleeding (such as nose bleed, bleeding gums, or easy bruising). Approximately, 5% of people suffer more severe and life threatening symptoms (e.g. dengue shock syndrome and dengue hemorrhagic fever). Dengue fever is directly related to infection by the dengue virus, a mosquito-borne single positive-stranded RNA virus. Developing a vaccine against the disease is compounded by five distinct serotypes of the dengue virus that can cause the disease, thus, any vaccine must immunize against all five types to be effective. To date no vaccines or curative treatments have been developed. A recent study published in the Journal of Virology identified the Src family member, Fyn Kinase as an important host-cell target required for RNA replication of the Dengue Virus in cells [53]. Treatment of cells infected with dengue virus with small molecule Src inhibitors, AZD0530 and Dasatanib inhibited viral replication, however, serial passaging of dengue virus in the presence of Dasatinib led to the identification of a mutation in the transmembrane domain 3 of the NS4B protein that overcomes the inhibition of RNA replication by AZD0530 and Dasatinib. Thus, similar to cancer cells, viruses can rapidly acquire resistance to targeted therapy and, thus, combination therapies represent the standard of care. In contrast to other Src inhibitors, compound 518 selectivity is tightly restricted to Src family members of the kinome including Fyn (Table 5) and, thus, may represent an ideal component of combination therapy for dengue fever or other virus infections where Src family members are implicated e.g. Epstein Barr Virus and HIV1 [63, 59].

In one particularly preferred embodiment, the viral disorder is HIV1.

In one preferred embodiment, the neurological disorder is Alzheimers disease. Recent studies have demonstrated the involvement of Fyn, a member of the Src family, in signaling pathways that lead to severe brain pathologies, such as Alzheimer's and Parkinson's diseases [73, 74]. Fyn plays a role in the regulation of amyloid-β (Aβ) plaques production and mediates Aβ-induced synaptic deficits and neurotoxicity. Fyn also induces tyrosine phosphorylation of tau [75]. A phase Ib study of saracatinib (AZD0530), a small molecule inhibitor with high potency for Src and Fyn, has been recently completed for the treatment of AD, with encouraging results that supports a larger ongoing Phase IIa clinical trial. Notably, at the highest dose used one of the subjects treated with Saracatinib developed congestive heart failure, which was linked to the treatment [76]. This dose-limiting adverse effect underscores the importance of highly specific Src family inhibitors in the treatment of different disease.

Another aspect relates to the use of a compound as described above in the preparation of a medicament for treating or preventing a disorder selected from osteoporosis, a neurological disorder, a proliferative disorder and a viral disorder.

Another aspect relates to the use of a compound as described above in the preparation of a medicament for treating or preventing a proliferative disorder, for example, cancer.

Preferably, the compound is administered in an amount sufficient to inhibit one or more tyrosine kinases. More preferably, the tyrosine kinase is a Src family kinase. As used herein the term "Src kinase" refers to a member of the Src family of non receptor tyrosine kinases.

Another aspect relates to a compound of the invention for use in the prevention or treatment of a disorder caused by, associated with or accompanied by any abnormal activity against a biological target, wherein the target is a tyrosine kinase, more preferably a Src family kinase.

Yet another aspect relates to the use of a compound of the invention in the preparation of a medicament for the prevention or treatment of a disorder caused by, associated with or accompanied by any abnormal activity against a biological target, wherein the target is a tyrosine kinase, more preferably a Src family kinase.

Another aspect of the invention relates to a method of treating a tyrosine kinase related disease or disorder, more preferably, a Src kinase related disease or disorder. The method according to this aspect of the present invention is effected by administering to a subject in need thereof a therapeutically effective amount of a compound of the present invention, as described hereinabove, either per se, or, more preferably, as a part of a pharmaceutical composition, mixed with, for example, a pharmaceutically acceptable carrier, as is detailed hereinafter.

Yet another aspect of the invention relates to a method of treating a mammal having a disease state alleviated by inhibition of a tyrosine kinase, more preferably a Src kinase, wherein the method comprises administering to a mammal a therapeutically effective amount of a compound according to the invention.

Another aspect of the invention relates to a method of treating a mammal having a disease state alleviated by the selective inhibition of c-Src kinase, wherein the method comprises administering to a mammal a therapeutically effective amount of a compound according to the invention. Preferably, the disease state is alleviated by the selective inhibition of c-Src kinase over Abl-kinase.

Preferably, the mammal is a human.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "administering" as used herein refers to a method for bringing a compound of the present invention and a protein kinase together in such a manner that the compound can affect the enzyme activity of the protein kinase either directly; i.e., by interacting with the protein kinase itself or indirectly; i.e., by interacting with another molecule on which the catalytic activity of the protein kinase is dependent. As used herein, administration can be accomplished either in vitro, i.e. in a test tube, or in vivo, i.e., in cells or tissues of a living organism.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

Herein, the term "preventing" refers to a method for barring an organism from acquiring a disorder or disease in the first place.

The term "therapeutically effective amount" refers to that amount of the compound being administered which will relieve to some extent one or more of the symptoms of the disease or disorder being treated.

For any compound used in this invention, a therapeutically effective amount, also referred to herein as a therapeutically effective dose, can be estimated initially from cell culture assays. For example, a dose can be formulated in animal models to achieve a circulating concentration range that includes the $IC_{50}$ or the $IC_{100}$ as determined in cell culture. Such information can be used to more accurately determine useful doses in humans. Initial dosages can also be estimated from in vivo data. Using these initial guidelines one of ordinary skill in the art could determine an effective dosage in humans.

Moreover, toxicity and therapeutic efficacy of the compounds described herein can be determined by standard pharmaceutical procedures in cell cultures or experimental animals, e.g., by determining the $LD_{50}$ and the $ED_{50}$. The dose ratio between toxic and therapeutic effect is the therapeutic index and can be expressed as the ratio between $LD_{50}$ and $ED_{50}$. Compounds which exhibit high therapeutic indices are preferred. The data obtained from these cell cultures assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (see, e.g., Fingl et al, 1975, In: The Pharmacological Basis of Therapeutics, chapter 1, page 1).

Dosage amount and interval may be adjusted individually to provide plasma levels of the active compound which are sufficient to maintain therapeutic effect. Usual patient dosages for oral administration range from about 50-2000 mg/kg/day, commonly from about 100-1000 mg/kg/day, preferably from about 150-700 mg/kg/day and most preferably from about 250-500 mg/kg/day. Preferably, therapeutically effective serum levels will be achieved by administering multiple doses each day. In cases of local administration or selective uptake, the effective local concentration of the drug may not be related to plasma concentration. One skilled in the art will be able to optimize therapeutically effective local dosages without undue experimentation.

As used herein, "tyrosine kinase related disease or disorder" refers to a disease or disorder characterized by inappropriate kinase activity or over-activity. Inappropriate activity refers to either; (i) kinase expression in cells which normally do not express said kinase; (ii) increased kinase expression leading to unwanted cell proliferation, differentiation and/or growth; or, (iii) decreased kinase expression leading to unwanted reductions in cell proliferation, differentiation and/or growth. Over-activity of kinase refers to either amplification of the gene encoding a particular kinase or production of a level of kinase activity, which can correlate with a cell proliferation, differentiation and/or growth disorder (that is, as the level of the kinase increases, the severity of one or more of the symptoms of the cellular disorder increases). Over activity can also be the result of ligand independent or constitutive activation as a result of mutations such as deletions of a fragment of a kinase responsible for ligand binding.

Preferred diseases or disorders that the compounds described herein may be useful in preventing, include cancer, osteoporosis, neurological disorders such as Parkinson's and Alzheimer's disease and viral disorders such as Epstein Barr Virus, Dengue Virus infection and HIV.

Thus, the present invention further provides use of compounds as defined herein for the manufacture of medicaments for the treatment of diseases where it is desirable to inhibit a tyrosine kinase, more preferably a Src kinase. Such diseases include proliferative disorders, osteoporosis and viral disorders.

Selectivity

Advantageously, selected compounds according to the invention exhibit selectivity for one or more protein kinases, more preferably, one or more tyrosine kinases.

In a preferred embodiment, the compounds of the invention exhibit selectivity for Src-kinase over one or more other protein kinases as measured by an appropriate kinase screening assay. The skilled person would be familiar with such assays, further details of which are provided in the accompanying examples section [77].

More preferably, the compounds of the invention exhibit at least a 2-fold selectivity for Src-kinase over one or more other protein kinases, preferably, at least a 5-fold selectivity, more preferably at least a 10-fold, at least a 25-fold, at least a 50-fold, at least a 100-fold, at least a 250-fold, at least a 500-fold, or at least a 1000-fold selectivity for Src-kinase over one or more other protein kinases.

In a preferred embodiment, the compounds of the invention exhibit at least a 2-fold selectivity for Src-kinase over Abl kinase, preferably, at least a 5-fold selectivity, more preferably at least a 10-fold, at least a 25-fold, at least a 50-fold, at least a 100-fold, at least a 250-fold, at least a 500-fold, or at least a 1000-fold selectivity for Src-kinase over Abl kinase, for example, as measured by the ratio of $IC_{50}^{Abl}/IC_{50}^{Src}$.

Pharmaceutical Compositions

For use according to the present invention, the compounds or physiologically acceptable salt, ester or other physiologically functional derivative thereof, described herein, may be presented as a pharmaceutical formulation, comprising the compounds or physiologically acceptable salt, ester or other physiologically functional derivative thereof, together with one or more pharmaceutically acceptable carriers therefore and optionally other therapeutic and/or prophylactic ingredients. The carrier(s) must be acceptable in the sense of being compatible with the other ingredients of the formulation and not deleterious to the recipient thereof. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s), buffer(s), flavouring agent(s), surface active agent(s), thickener(s), preservative(s) (including anti-oxidants) and the like, and substances included for the purpose of rendering the formulation isotonic with the blood of the intended recipient.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release—controlling matrix, or is coated with a suitable release—controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds. Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microliters, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

According to a further aspect of the invention, there is provided a process for the preparation of a pharmaceutical or veterinary composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formulae (I) or (II) in conjunction or association with a pharmaceutically or veterinarily acceptable carrier or vehicle.

Salts/Esters

The compounds of the invention can be present as salts or esters, in particular pharmaceutically and veterinarily acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. hydrohalic acids such as hydrochloride, hydrobromide and hydroiodide, sulphuric acid, phosphoric acid sulphate, bisulphate, hemisulphate, thiocyanate, persulphate and sulphonic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Salts which are not pharmaceutically or veterinarily acceptable may still be valuable as intermediates.

Preferred salts include, for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers, diastereoisomers and tautomers of the compounds of the invention. The person skilled in the art will recognise compounds that possess optical properties (one or more chiral carbon atoms) or tautomeric characteristics. The corresponding enantiomers and/or tautomers may be isolated/prepared by methods known in the art.

Enantiomers are characterised by the absolute configuration of their chiral centres and described by the R- and S-sequencing rules of Cahn, Ingold and Prelog. Such conventions are well known in the art (e.g. see 'Advanced Organic Chemistry', $3^{rd}$ edition, ed. March, J., John Wiley and Sons, New York, 1985).

Compounds of the invention containing a chiral centre may be used as a racemic mixture, an enantiomerically enriched mixture, or the racemic mixture may be separated using well-known techniques and an individual enantiomer may be used alone.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. For example, the invention includes compounds of general formulae (I) or (II) where any hydrogen atom has been replaced by a deuterium atom. Isotopic variations of the agent of the present invention and pharmaceutically acceptable salts thereof of this invention can generally be prepared by conventional procedures using appropriate isotopic variations of suitable reagents.

Prodrugs

The invention further includes the compounds of the present invention in prodrug form, i.e. covalently bonded compounds which release the active parent drug according to general formula (I) or (II) in vivo. Such prodrugs are generally compounds of the invention wherein one or more appropriate groups have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Solvates

The present invention also includes solvate forms of the compounds of the present invention. The terms used in the claims encompass these forms.

Polymorphs

The invention further relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Administration

The pharmaceutical compositions of the present invention may be adapted for rectal, nasal, intrabronchial, topical (including buccal and sublingual), vaginal or parenteral (including subcutaneous, intramuscular, intravenous, intraarterial and intradermal), intraperitoneal or intrathecal administration. Preferably the formulation is an orally administered formulation. The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg and more preferably from 10-100 mg, of active ingredient per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropyl-methylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Other forms of administration comprise solutions or emulsions which may be injected intravenously, intraarterially, intrathecally, subcutaneously, intradermally, intraperitoneally or intramuscularly, and which are prepared from sterile or sterilisable solutions. Injectable forms typically contain between 10-1000 mg, preferably between 10-250 mg, of active ingredient per dose.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

In accordance with this invention, an effective amount of a compound of general formulae (I) or (II) may be administered to inhibit the kinase implicated with a particular condition or disease. Of course, this dosage amount will further be modified according to the type of administration of the compound. For example, to achieve an "effective amount" for acute therapy, parenteral administration of a compound of general formula (I) or (II) is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit a kinase. The compounds may be administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect.

The compounds of this invention may also be administered orally to the patient, in a manner such that the concentration of drug is sufficient to achieve one or more of the therapeutic indications disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

Combinations

In a particularly preferred embodiment, the one or more compounds of the invention are administered in combination with one or more other active agents, for example, existing drugs available on the market. In such cases, the compounds of the invention may be administered consecutively, simultaneously or sequentially with the one or more other active agents.

Drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease or delay the emergence of resistance.

Beneficial combinations may be suggested by studying the inhibitory activity of the test compounds with agents known or suspected of being valuable in the treatment of a particular disorder. For example, the invention relates to the use of a compound as described above in an assay for identifying compounds that promote additive and synergistic activity upon anti-cancer activities when combined with the compound.

Preferably the assay is a high-throughput cell based phenotypic screen. This procedure can also be used to determine the order of administration of the agents, i.e. before, simultaneously, or after delivery. Such scheduling may be a feature of all the active agents identified herein.

Assay

A further aspect of the invention relates to the use of a compound as described above in an assay for identifying further candidate compounds capable of inhibiting or selectively inhibiting one or more tyrosine kinases, more preferably a Src family kinase. Preferably, the candidate compound is capable of selectively inhibiting c-Src kinase over Abl-kinase.

Preferably, the assay is a competitive binding assay.

More preferably, the competitive binding assay comprises contacting a compound of the invention with the kinase, and a candidate compound and detecting any change in the interaction between the compound according to the invention and the kinase.

Preferably, the candidate compound is generated by conventional SAR modification of a compound of the invention.

As used herein, the term "conventional SAR modification" refers to standard methods known in the art for varying a given compound by way of chemical derivatisation.

Thus, in one aspect, the identified compound may act as a model (for example, a template) for the development of other compounds. The compounds employed in such a test may be free in solution, affixed to a solid support, borne on a cell surface, or located intracellularly. The abolition of activity or the formation of binding complexes between the compound and the agent being tested may be measured.

The assay of the present invention may be a screen, whereby a number of agents are tested. In one aspect, the assay method of the present invention is a high throughput screen.

This invention also contemplates the use of competitive drug screening assays in which neutralising antibodies capable of binding a compound specifically compete with a test compound for binding to a compound.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Preferably, the competitive binding assay comprises contacting a compound of the invention with a kinase in the presence of a known substrate of said kinase and detecting any change in the interaction between said kinase and said known substrate.

A further aspect of the invention provides a method of detecting the binding of a ligand to a kinase, said method comprising the steps of (i) contacting a ligand with a kinase in the presence of a known substrate of said kinase;

(ii) detecting any change in the interaction between said kinase and said known substrate;

and wherein said ligand is a compound of the invention.

One aspect of the invention relates to a process comprising the steps of:

(a) performing an assay method described hereinabove;

(b) identifying one or more ligands capable of binding to a ligand binding domain; and (c) preparing a quantity of said one or more ligands.

Another aspect of the invention provides a process comprising the steps of:

(a) performing an assay method described hereinabove;

(b) identifying one or more ligands capable of binding to a ligand binding domain; and (c) preparing a pharmaceutical composition comprising said one or more ligands.

Another aspect of the invention provides a process comprising the steps of:
(a) performing an assay method described hereinabove;
(b) identifying one or more ligands capable of binding to a ligand binding domain;
(c) modifying said one or more ligands capable of binding to a ligand binding domain;
(d) performing the assay method described hereinabove;

establishing whether a known or newly discovered kinase contributes a critical or at least significant biochemical function during the establishment or progression of a disease state, a process commonly referred to as 'target validation'.

Synthesis

Another aspect of the invention relates to a process for preparing a compound of formula I as defined above, said process comprising the steps of:

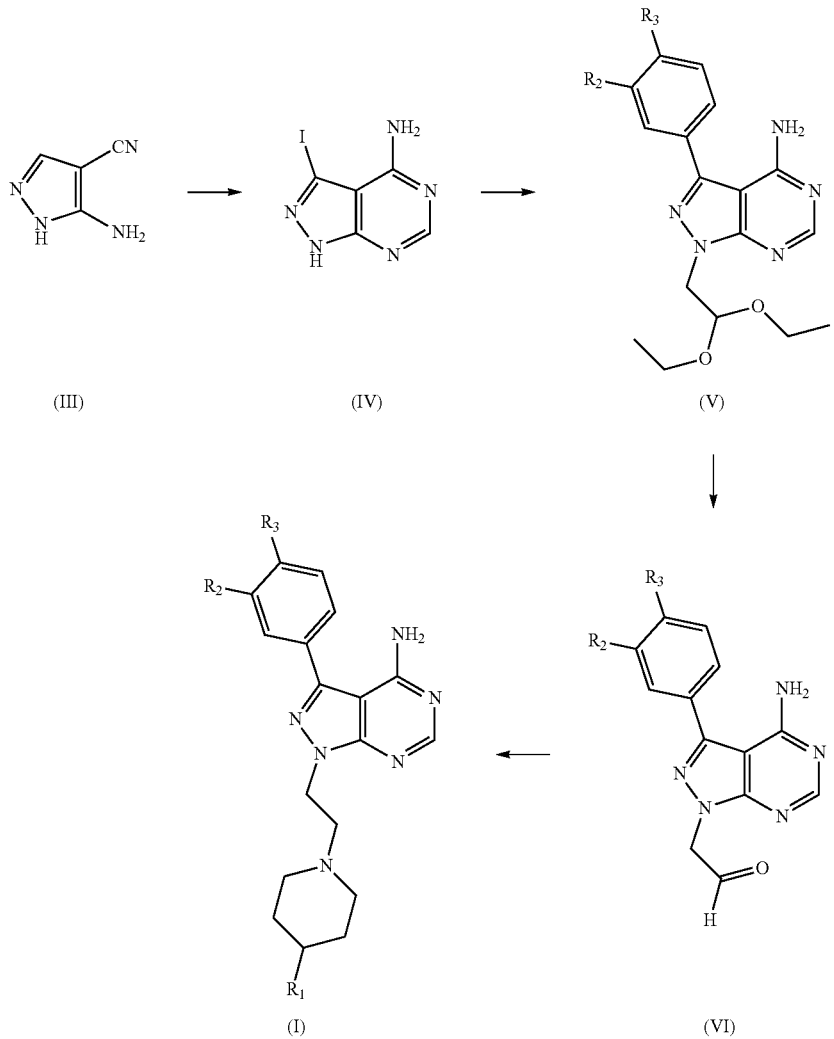

(e) optionally preparing a pharmaceutical composition comprising said one or more ligands.

The invention also relates to a ligand identified by the method described hereinabove.

Yet another aspect of the invention relates to a pharmaceutical composition comprising a ligand identified by the method described hereinabove.

Another aspect of the invention relates to the use of a ligand identified by the method described hereinabove in the preparation of a pharmaceutical composition for use in the treatment of one or more disorders as described hereinabove.

The above methods may be used to screen for a ligand useful as an inhibitor of one or more kinases.

Compounds of general formulae (I) or (II) are useful both as laboratory tools and as therapeutic agents. In the laboratory certain compounds of the invention are useful in (i) converting a compound of formula (III) to a compound of formula (IV);
(ii) converting said compound of formula (IV) to a compound of formula (V);
(ii) converting said compound of formula (V) to a compound of formula (VI); and
(iv) converting said compound of formula (VI) to a compound of formula (I).

A preferred synthetic scheme for preparing compounds according to the invention is set out in FIG. 2. Preferred reagents for steps (i) to (iv) are as shown in FIG. 2.

By way of illustration 4-aminopyrazolopyrimidine was synthesized by microwave-assisted reaction of pyrazole in an excess of formamide. N-Iodosuccinimide (NIS) mediated iodination, N-alkylation with bromoacetaldehyde diethyl acetal, followed by Suzuki cross-coupling with the corresponding arylboronic acid produced acetal-protected derivative in good overall yield (25-50%, 3 steps). Quantitative acetal deprotection in TFA:water (1:1) gave rise the corresponding aldehyde derivative, which was used to generate the final compounds by reductive amination with cyclic secondary amines (piperidines, morpholine and piperazines).

The invention is further described by way of the following non-limiting examples, and with reference to the following figures, wherein.

Figure 1:
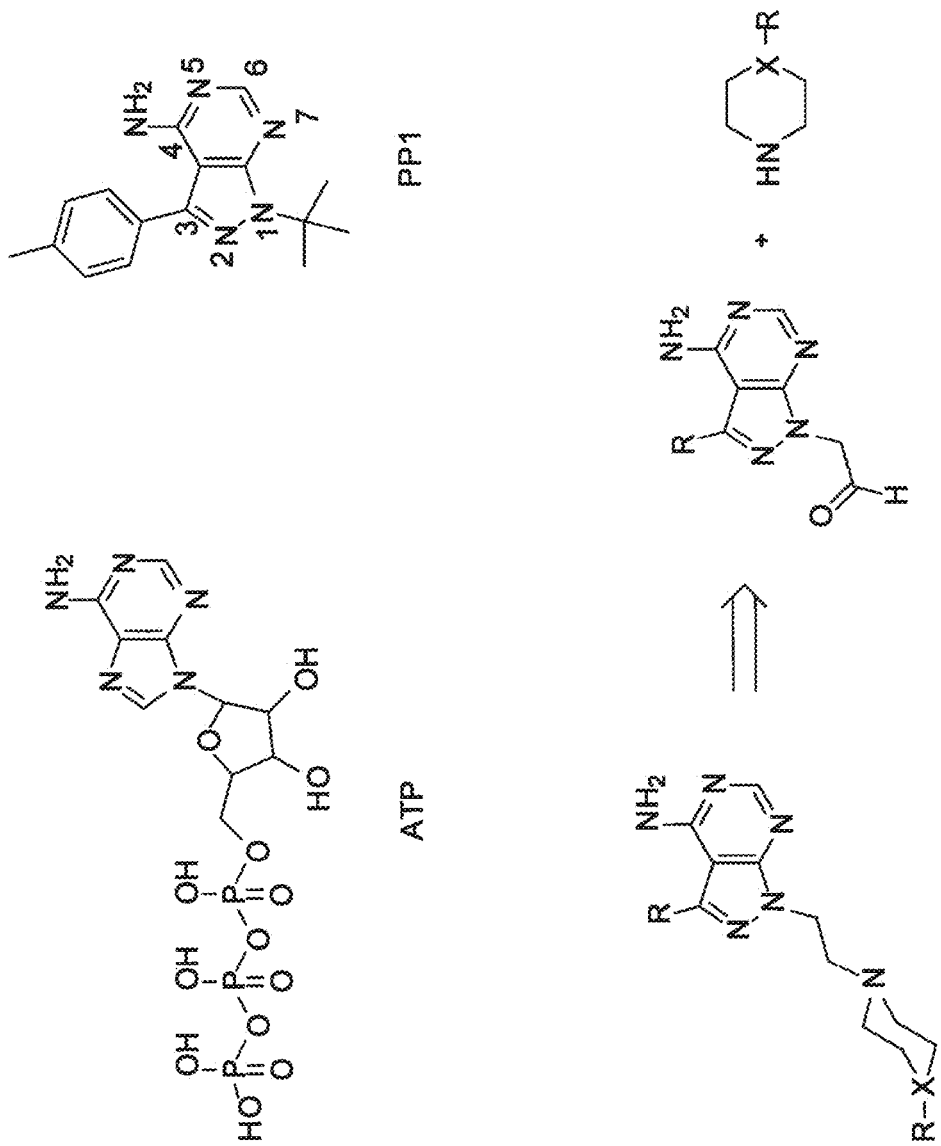
FIG. 1 shows: Upper panel: ATP and PP1 (neutral forms); Lower panel: general structure of the novel compounds and their retrosynthetic analysis.
Figure 2:
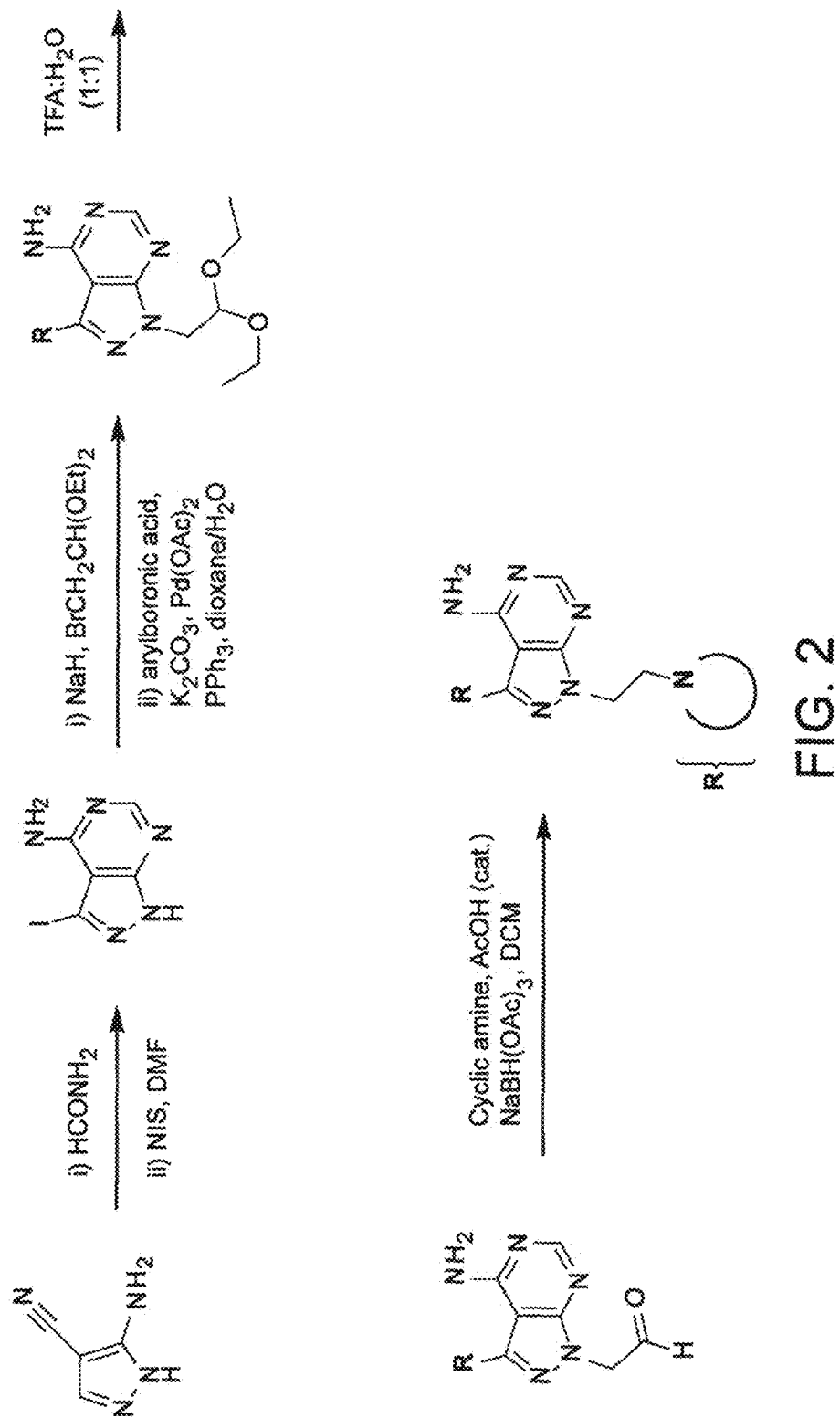
FIG. 2 shows a preferred synthetic scheme for preparing compounds according to the invention.
Figure 3:
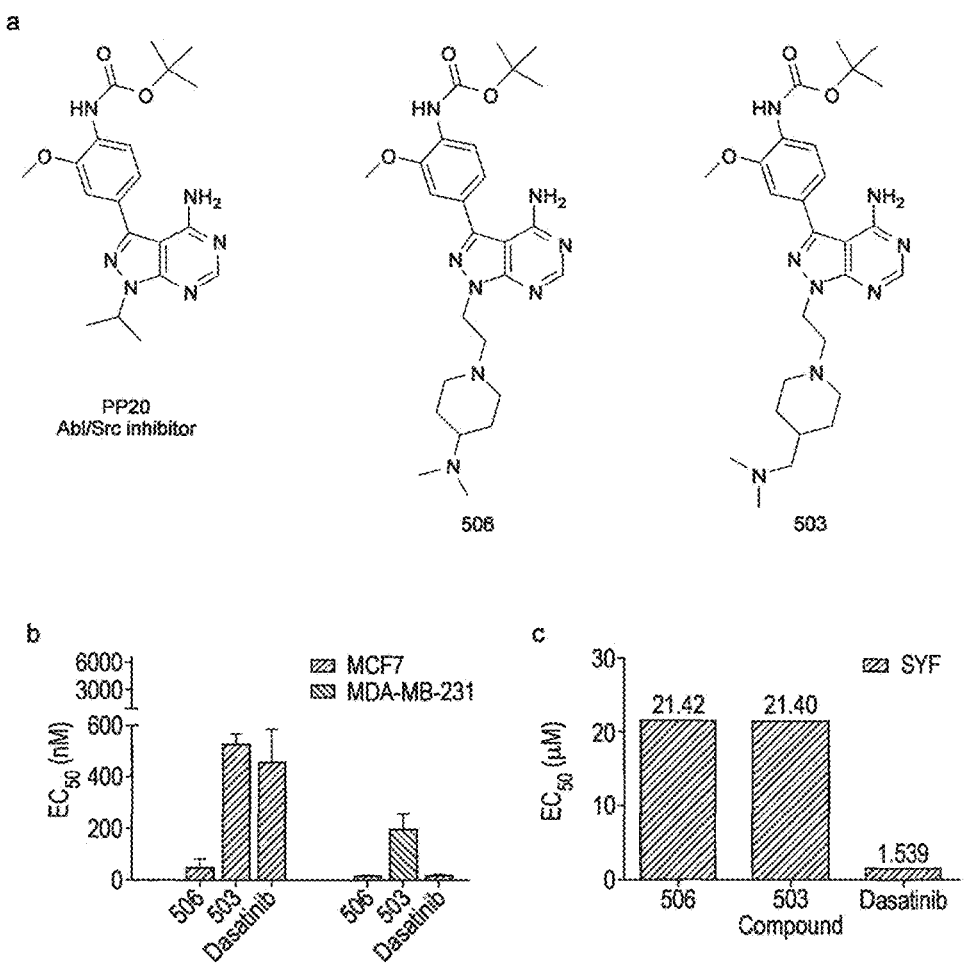

FIG. 3 shows: a) Compounds PP20 [35], 506 and 503; b) $EC_{50}$ values calculated after incubation of MCF7 and MDA-MB-231 cells with compounds 506 and 503. Dasatinib was used as positive control; c) $EC_{50}$ values calculated after incubation of SYF cells with compounds 506, 503 and Dasatinib.

Figure 4:
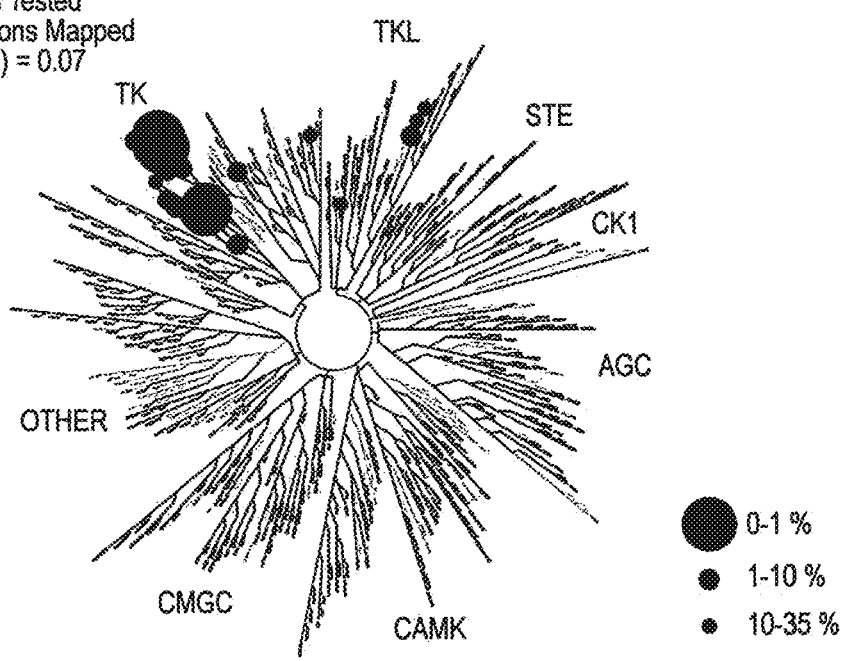

FIG. 4 shows a full kinome screen dot plot of compound 506 at 1 µM. Enzymatic activity of most kinases tested (321) was not, or only weakly, affected by compound 506 (activity>35%). Although 21 kinases were identified as potential hits (<35%), compound 506 was most active against 3 kinases (0-0.5% of activity) at the concentration tested: c-Src, Yes and PTK6. Calculation of $IC_{50}$ values for a panel of kinases showed that c-Src and Yes were in fact inhibited at sub-nanoM range. However, PTK6 (also known as Brk, breast cancer kinase) showed $IC_{50}$=20 nM. Other Src family kinases were also identified to have $IC_{50}$ in the low nanoM range.

Figure 5:
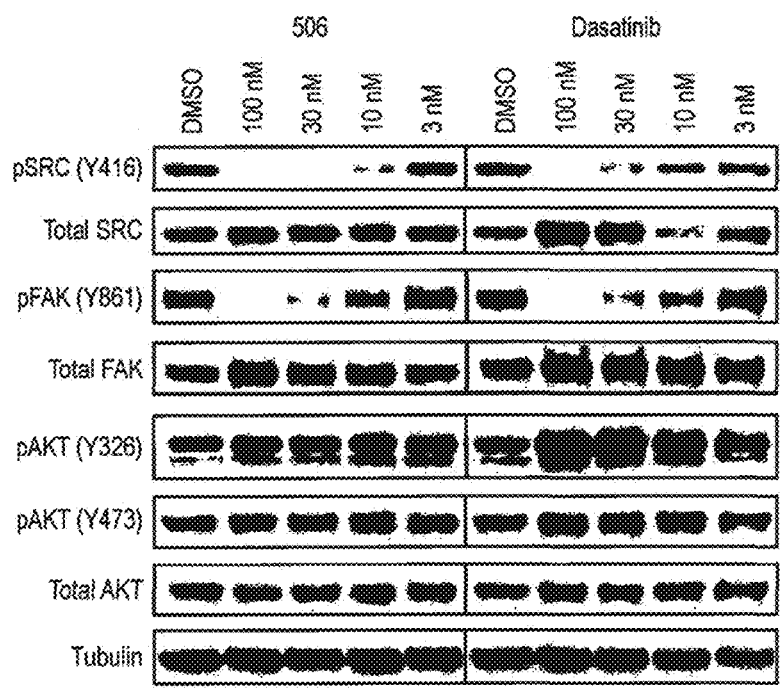

FIG. 5 shows a Western Blot on MDA-MB-231 cells comparing compound 506 with Dasatinib. Compound 506 induced strong inhibition of SRC auto-phosphorylation ($^{Y416}$phospho-SRC) and downstream SRC-mediated phosphorylation of FAK ($^{Y416}$phospho-FAK). While Dasatinib inhibited pSRC and pFAK at the same concentrations, it also displayed additional effects in other pathways (strong upregulation of pAKT) and seemed to stabilize total SRC.

Figure 6:
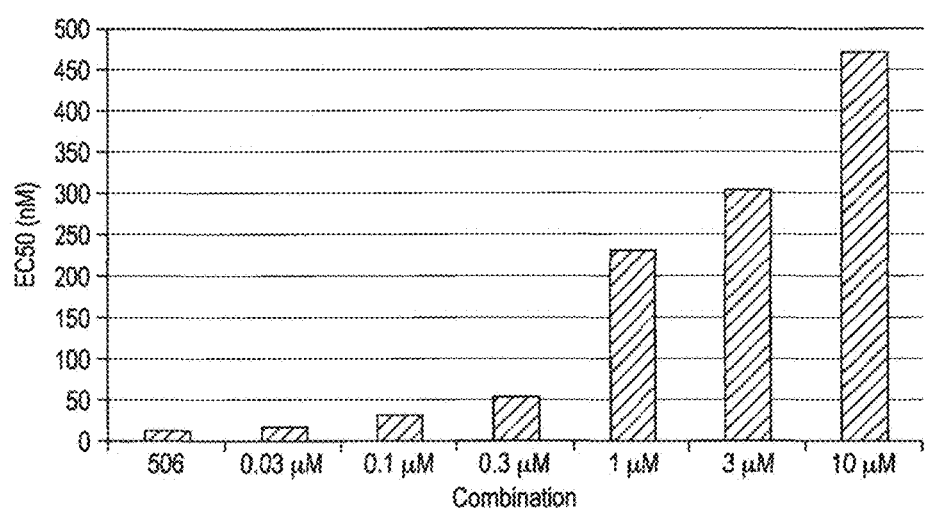

FIG. 6 shows the antagonistic effect of GNF-2 (selective Abl inhibitor) over the $EC_{50}$ values of compound 506. As shown in the Figure, $EC_{50}$ values are incremented up to 50-fold at 10 µM of GNF-2.

Figure 7:
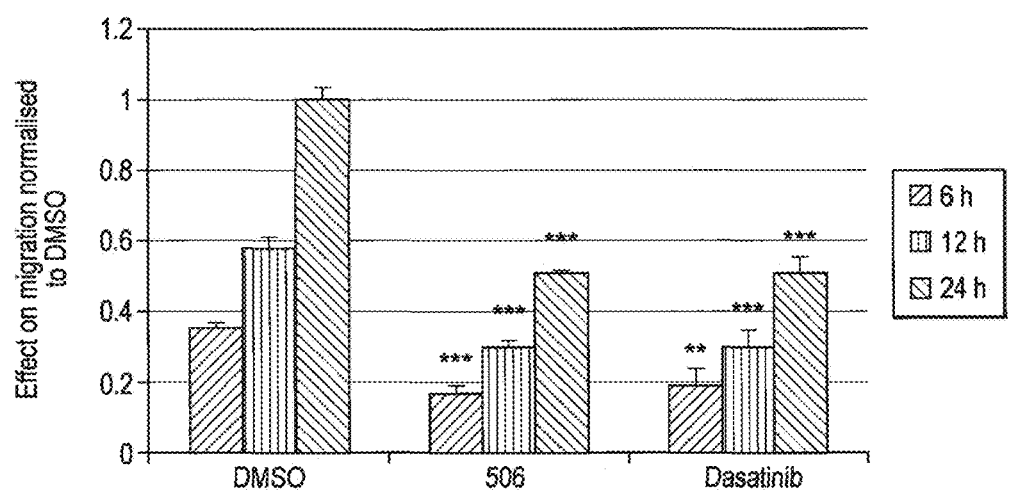

FIG. 7 shows the migration of MDA-MB-231 treated cells across a scratch wound at 6 h, 12 h and 24 h time points normalized to DMSO. Drugs, compound 506 and Dasatinib, were used at 10 nM and compared against DMSO.

Figure 8:
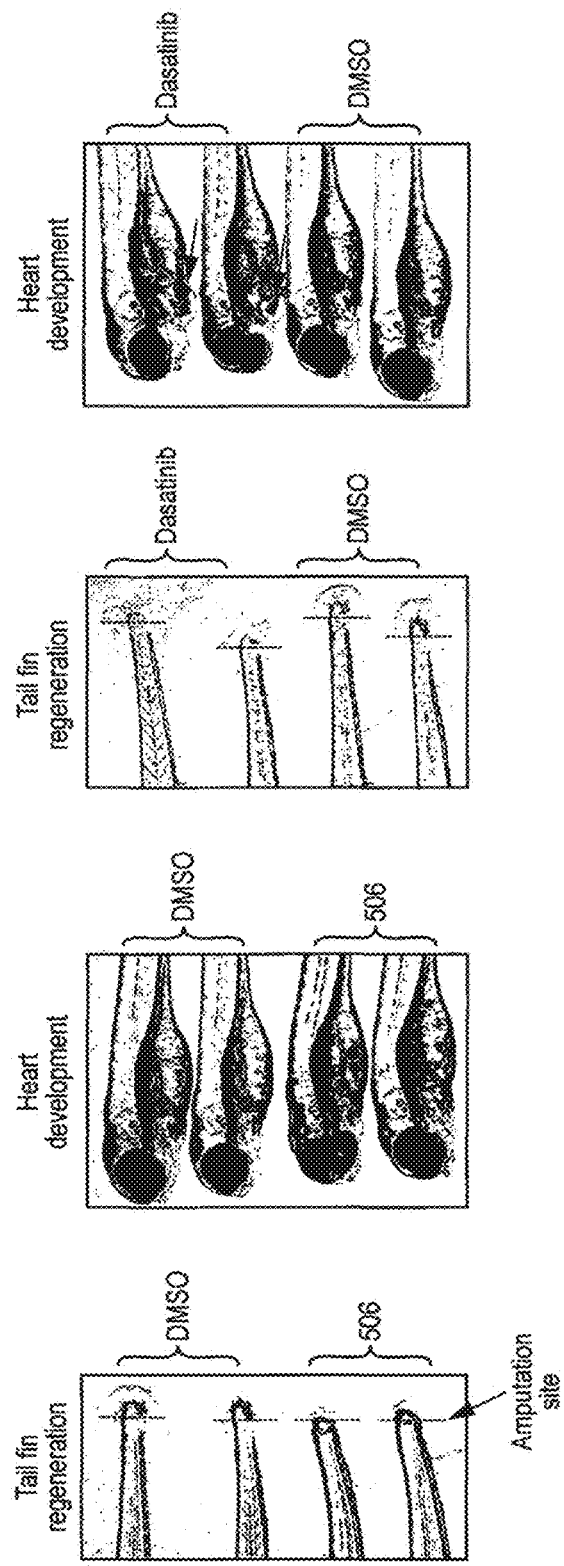

FIG. 8 shows a zebrafish tail regeneration assay. Procedure: 2 hour pre-treatment with dasatinib or compound 506 at 100 µM→tail cut→treatment for 2 more hours→wash out, image 2 days later. Note heart enlargement induced by dasatinib treatment.

Figure 9:
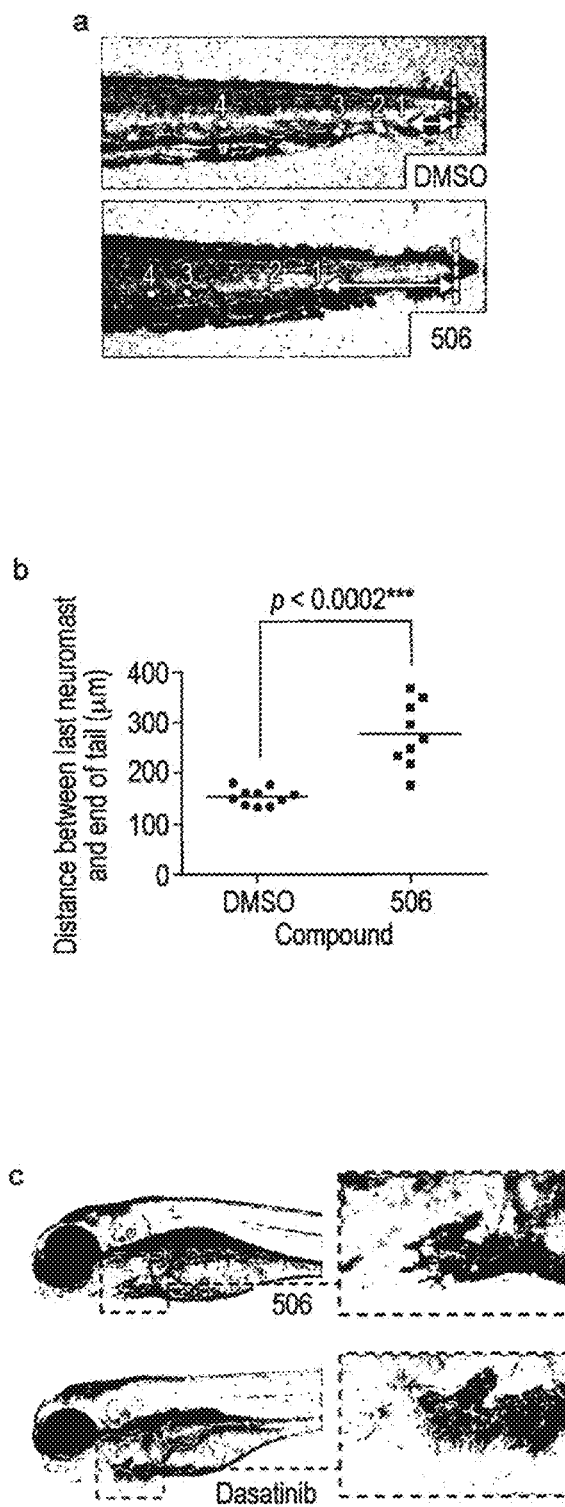

FIG. 9 shows phenotypic screening of SRC inhibitor 506 in zebrafish. (a,b) Neuromast migration assay. Fresh E3 media with DMSO or 506 (500 µM) was added to zebrafish embryos at 20 hpf, 36 hpf and 48 hpf, and imaged at 72 hpf. (a) Representative images of the tail of a 3 dpf zebrafish without (top) and with 506 treatment (bottom). Neuromasts are identified by GFP expression (green) and the tip of the tail as a red line. Yellow arrow indicates shortest distance from tail tip to a neuromast. (b) Imaging analysis of the distance between the last neuromast and the tip of the tail (n=10) under treatment with DMSO (negative control) or 506 (500 µM). P value calculated from t-test. (c) Study of zebrafish heart development under short treatment with 506 (500 µM) and dasatinib (10 µM). Compounds were added to 2 dpf zebrafish embryos and incubated for 4 h (n=5). Subsequently, fresh media was added and fish imaged after 48 h incubation.

Figure 10:
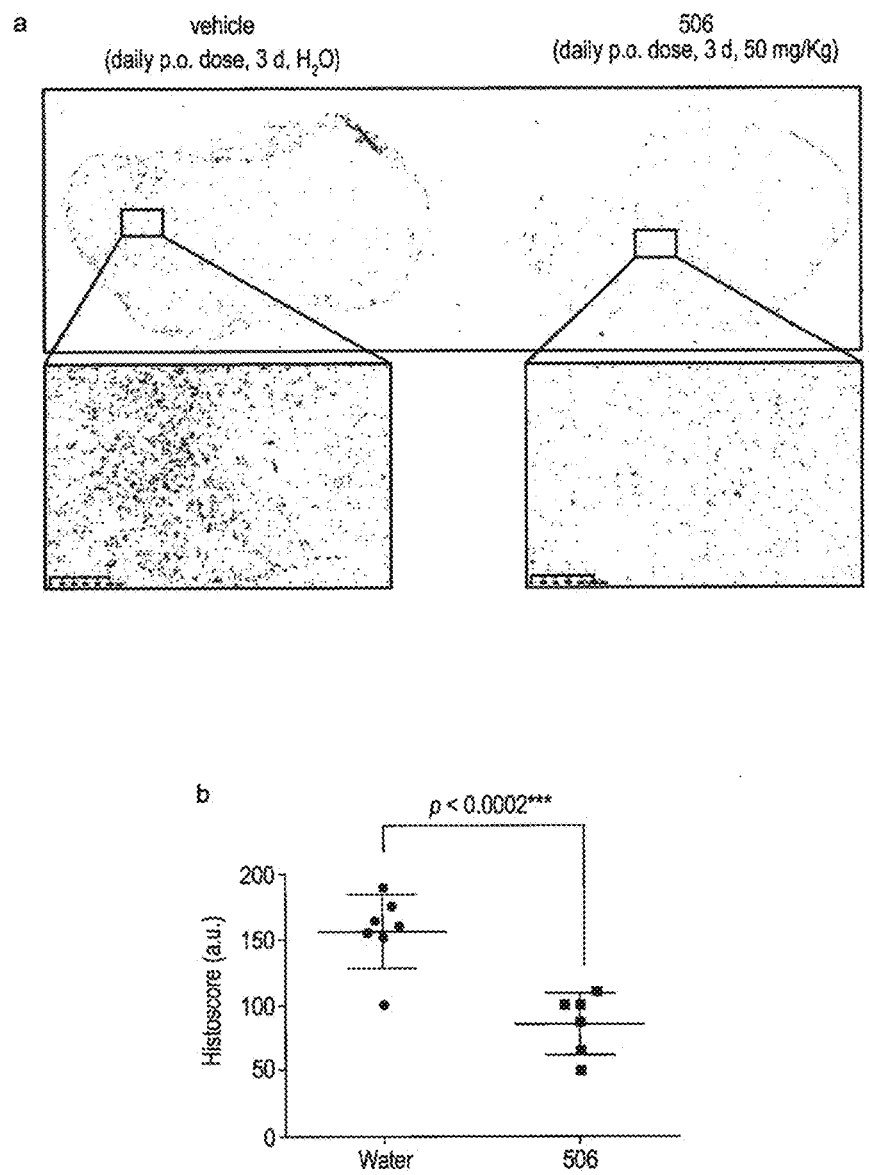

FIG. 10 shows immunohistochemical analysis of phospho-SRC$^{Y416}$ in human tumor xenografts. (a) Images of representative sections (low and high resolution) of HCT116 xenografts from: (left) untreated mice and (right) mice treated with 506 (n=4). (b) Histoscore analysis (6-7 sections analysed per experiment). Quantification of immunohistochemistry across tumor tissue sections from untreated animals (water) and 506 treated groups performed in blinded fashion. P value calculated from t-test.

EXAMPLES

Materials and Methods
General Procedures for Synthesis of Compounds
Chromatography
Column chromatography refers to silica gel chromatography and was carried out manually using conventional glass columns and silica gel (pore size 60 Å, particle size 230-400 mesh, 40-63 µm) from Sigma-Aldrich.

Analytical Methods
$^1$H Nuclear magnetic resonance (NMR) spectroscopy was carried out using a 500 MHz Bruker Avance III spectrometer in the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; br, broad. Low Resolution Mass Spectra (LRMS) were obtained using a Microsaic Systems 4000 MiD system under electron spray ionisation (ESI) conditions. High Resolution Mass Spectra (HRMS) were obtained using a Bruker 3.0 T Apex II Spectrometer. Thin layer chromatography was run on Merck TLC Silica gel 60 F254 plates; typically 5 cm×10 cm. Detection was achieved using a 254 nm UV source or permanganate stain.

Compound Preparation
Where the preparation of starting materials is not described, these are commercially available, known in the literature, or readily obtainable by those skilled in the art using standard procedures. All commercially available chemicals used herein were obtained from either Fisher Scientific, Matrix Scientific, Sigma-Aldrich or VWR International Ltd. Where it is stated that compounds were prepared analogously to earlier examples or intermediates, it will be appreciated by the skilled person that the reaction time, number of equivalents of reagents and temperature can be modified for each specific reaction and that it may be necessary or desirable to employ different work-up or purification techniques. Where reactions were carried out using microwave irradiation, the microwave used was an Initiator 60 supplied by Biotage. Non-microwave reactions were performed under an inert atmosphere of nitrogen using anhydrous solvents. The actual power supplied varies during the course of the reaction in order to maintain a constant temperature.

Abbreviations
CDCl$_3$=Deuterated Chloroform
DCM=Dichloromethane
Et$_2$O=Diethyl ether
MgSO$_4$=Magnesium sulfate
DMF=N,N-Dimethylformamide
eq.=Equivalents mg=Milligram
ml=Milliliter
mmol=Millimoles
m/z=Mass to charge ratio
MeOD=Deuterated Methanol
MHz=Mega Hertz
mw=Microwave
TLC=Thin Layer Chromatography
NEts=Triethylamine
THF=Tetrahydrofuran
MeOH=Methanol
TFA=Trifluoroacetic acid
r.t.=Room temperature
AcOH=Acetic acid
EtOH=Ethanol
EtOAc=Ethyl Acetate
UV=Ultraviolet
DMSO=Dimethylsulphoxide The synthesis of selected compounds of the invention is described below.

1H-pyrazolo[3,4-d]pyrimidin-4-amine

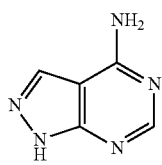

5-amino-1H-pyrazole-4-carbonitrile (3 g, 27.77 mmol) and formamide (15 ml) were added to a 20 ml microwave vial and the mixture heated at 180° C. for 2 hours using microwave radiation. The precipitate formed on cooling was filtered off and washed with water (50 ml) and allowed to dry giving the product as a cream solid (3.5 g, 25.92 mmol, 93%). $^1$H NMR (500 MHz, DMSO) δ 13.34 (s, 1H), 8.13 (s, 1H), 8.07 (s, 1H), 7.69 (br. m, 2H); $^{13}$C NMR (126 MHz, DMSO) δ 158.19 (CH), 156.03 (C), 154.98 (C), 132.79 (CH), 99.83 (C); MS (ES +ve) [M+H]$^+$: 136.0, 157.9 (+Na), (ES −ve) [M−H]$^-$: 133.9.

3-iodo-1H-pyrazolo[3,4-d]pyrimidin-4-amine

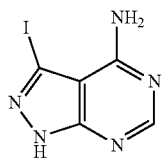

1H-pyrazolo[3,4-d]pyrimidin-4-amine (1.5 g, 11.11 mmol) was suspended in 15 ml of DMF and N-iodosuccinimide (1.2 eq., 3.0 g, 13.34 mmol) added. The mixture was heated at 180° C. in the microwave for an hour. EtOH (80 ml) was added to the reaction and a precipitate began to form, which was aided by sonication. The precipitate was filtered and washed with EtOH (×3, 20 ml) and allowed to dry in an oven at 40° C. overnight to give a sand coloured solid (2.115 g, 8.105 mmol, 73.0%). $^1$H NMR (500 MHz, DMSO) δ 13.80 (s, 1H), 8.16 (s, 1H), 7.79-6.44 (m, 2H); $^{13}$C NMR (126 MHz, DMSO) δ 157.60 (C), 156.08 (CH), 155.04 (C), 102.50 (C), 89.82 (C); MS (ES +ve) [M+H]$^+$: 283.9 (+Na), (ES −ve) [M−H]$^-$: 259.9, 287.8 (+Na).

1-(2,2-diethoxyethyl)-3-iodo-pyrazolo[3,4-d]pyrimidin-4-amine

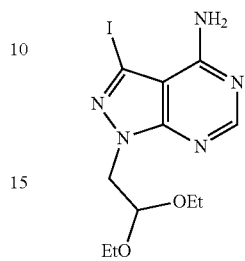

To a solution of 3-iodo-1H-pyrazolo[3,4-d]pyrimidin-4-amine (500 mg, 1.92 mmol) in DMF (15 ml) was added sodium hydride (1.5 eq., 2.88 mmol, 60% dispersion in mineral oil, 115.2 mg) and the solution allowed to stir for 30 mins until the gas evolution had subsided. Bromoacetaldehyde diethyl acetal (1.5 eq. 2.88 mmol, 0.435 ml) was then added dropwise and the mixture heated at 150° C. in the microwave for 40 mins. EtOAc and water (50 ml) were added to the mixture and the organics separated. The aqueous layer was washed with EtOAc (50 ml, ×3) and the organics combined and washed with water (×3, 30 ml), dried over MgSO$_4$ and concentrated in vacuo. The crude product was purified by column chromatography MeOH/DCM (0-5%) to give a light orange solid (461 mg, 1.22 mmol, 63.7%). $^1$H NMR (500 MHz, DMSO) δ 8.21 (s, 1H), 7.90-6.30 (m, 2H), 4.93 (t, J=5.7, 1H), 4.33 (d, J=5.8, 2H), 3.62 (dq, J=9.4, 6.9, 2H), 3.40 (dq, J=9.6, 7.0, 2H), 0.98 (t, J=7.0, 6H); $^{13}$C NMR (126 MHz, DMSO) δ 157.86 (C), 156.30 (CH), 154.03 (C), 103.18 (CH), 99.50 (C), 89.51 (C), 61.39 (CH$_2$), 48.76 (CH$_2$), 15.39 (CH$_3$); MS (ES +ve) [M+H]$^+$: 377.8, 400.0 (+Na), (ES −ve) [M−H]$^-$: 376.0.

1-(2,2-diethoxyethyl)-3-(p-tolyl)pyrazolo[3,4-d]pyrimidin-4-amine

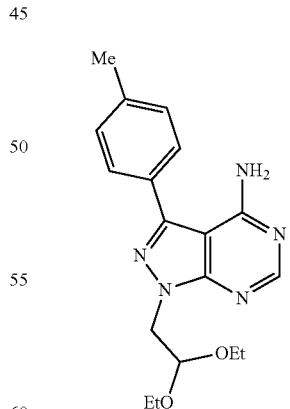

To a solution of 1-(2,2-diethoxyethyl)-3-iodo-pyrazolo[3,4-d]pyrimidin-4-amine (1.135 g, 3.01 mmol) in dioxane/water (10 ml/1 ml) was added p-tolylboronic acid (1.5 eq., 614 mg, 4.52 mmol), potassium carbonate (1.5 eq., 624.7 mg, 4.52 mmol) followed by palladium acetate (5 mol %, 33.8 mg) and the mixture heated in the microwave at 120°

C. for an hour. EtOAc and water (50 ml) were added to the mixture and the organic layer separated, dried over MgSO₄ and concentrated in vacuo. The crude product was purified by column chromatography, MeOH/DCM (0-5%) to give a light brown solid (902 mg, 2.64 mmol, 87.8%). ¹H NMR (500 MHz, CDCl₃) δ 8.42 (s, 1H), 7.58 (d, J=8.0, 2H), 7.34 (d, J=7.8, 2H), 5.12 (t, J=5.8, 1H), 4.58 (d, J=5.8, 2H), 3.78 (dq, J=9.4, 7.0, 2H), 3.52 (dq, J=9.4, 7.0, 2H), 2.44 (s, 3H), 1.12 (t, J=7.0, 6H); ¹³C NMR (126 MHz, CDCl₃) δ 158.28 (C), 156.43 (C), 155.55 (CH), 145.25 (C), 139.76 (C), 131.90 (CH), 128.93 (CH), 100.49 (CH), 62.46 (CH₂), 49.53 (CH₂), 21.09 (CH₃), 15.78 (CH₃); MS (ES +ve) [M+1]⁺: 341.19, (ES −ve) [M−1]⁻: 340.0.

2-[4-amino-3-(p-tolyl)pyrazolo[3,4-d]pyrimidin-1-yl]acetaldehyde

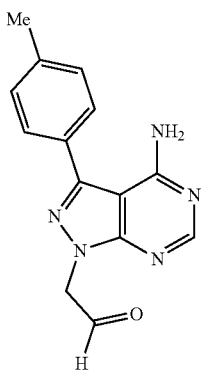 [SMILES: Cc1ccc(-c2nn(CC=O)c3ncnc(N)c23)cc1]

To a suspension of 1-(2,2-diethoxyethyl)-3-(p-tolyl)pyrazolo[3,4-d]pyrimidin-4-amine (400 mg, 1.17 mmol) in 5 ml of water was added 5 ml of TFA and the mixture heated to 100° C. for 30 mins in the microwave. The mixture was transferred to a RBF, washed with DCM and concentrated in vacuo. The product was washed with DCM and Et₂O and dried in vacuo to give a light brown solid (assuming quantitative yield). NMR spectra were not obtained for this compound as different salts of the product led to messy spectra.

Compounds 105 & 109.

To a suspension of 2-[4-amino-3-(p-tolyl)pyrazolo[3,4-d]pyrimidin-1-yl]acetaldehyde (40 mg, 0.105 mmol) in DCM (1 ml) was added either, N-dimethyl-2-piperazin-1-yl-ethanamine or N,N-dimethylpiperidin-4-amine (1 eq., 0.105 mmol), respectively, and a drop of AcOH and the mixture allowed to stir for 10 mins. Sodium triacetoxyborohydride (22.2 mg, 0.105 mmol) was then added and the mixture stirred until complete (~1 hr). The reaction mixture was concentrated in vacuo and purified without any further work up due to the high solubility of the product in the aqueous layer.

1-[2-(4-methylpiperazin-1-yl)ethyl]-3-(p-tolyl)pyrazolo[3,4-d]pyrimidin-4-amine

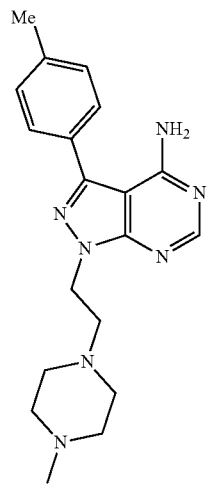 [SMILES: Cc1ccc(-c2nn(CCN3CCN(C)CC3)c3ncnc(N)c23)cc1]

Purified by column chromatography (MeOH/DCM 0-10%-10% MeOH with 3 drops of NH₃ aq. per 20 ml) to give a pale orange solid (20 mg, 0.057 mmol, 54.2%) ¹H NMR (500 MHz, MeOD) δ 8.27 (s, 1H), 7.60 (d, J=8.1, 2H), 7.41 (d, J=7.8, 2H), 4.57 (t, J=6.5, 2H), 2.97 (t, J=6.5, 2H), 2.53 (m, 8H), 2.47 (s, 3H), 2.37 (s, 3H); ¹³C NMR (126 MHz, CDCl₃) δ 158.02 (C), 155.87 (CH), 154.77 (C), 144.58 (C), 139.25 (C), 130.45 (C), 130.14 (CH), 128.50 (CH), 98.59 (C), 56.89 (CH₂), 54.91 (CH₂), 52.50 (CH₂), 45.59 (CH₃), 44.60 (CH₂), 21.47 (CH₃); MS (ES +ve) [M+1]⁺: 352.0, 374.2 (+Na), (ES −ve) [M−1]⁻: 350.2; HRMS (ES +ve), C₁₉H₂₆N₇ [M+H]⁺: calculated 352.22442, found 352.224816.

1-[2-[4-(2-dimethylaminoethyl)piperazin-1-yl]ethyl]-3-(p-tolyl)pyrazolo[3,4-d]pyrimidin-4-amine (105)

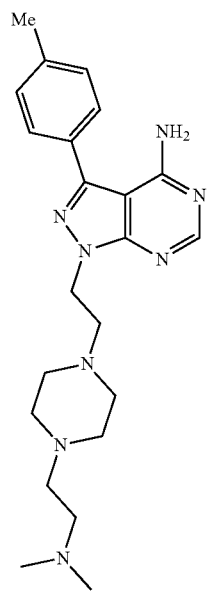 [SMILES: Cc1ccc(-c2nn(CCN3CCN(CCN(C)C)CC3)c3ncnc(N)c23)cc1]

Purified by column chromatography (MeOH/DCM 5-10%-10% MeOH with 25 drops of NH$_3$ aq. per 100 ml) to give a pale orange solid (5 mg, 0.0312 mmol, 11.7). $^1$H NMR (500 MHz, MeOD) δ 8.27 (s, 1H), 7.59 (d, J=8.0, 2H), 7.41 (d, J=8.0, 2H), 4.56 (t, J=6.6, 2H), 2.96 (t, J=6.6, 2H), 2.89 (t, J=6.6, 2H), 2.76-2.60 (m, 6H), 2.60 (s, 6H), 2.51 (m, 4H), 2.46 (s, 3H); $^{13}$C NMR (126 MHz, MeOD) δ 158.50 (C), 155.39 (CH), 154.14 (C), 145.16 (C), 139.21 (C), 129.83 (C), 129.60 (CH), 128.10 (CH), 97.76 (C), 56.40 (CH$_2$), 54.64 (CH$_2$), 53.51 (CH$_2$), 52.56 (CH$_2$), 52.24 (CH$_2$), 43.79 (CH$_2$), 43.36 (CH$_3$), 19.97 (CH); MS (ES +ve) [M+1]$^+$: 409.3, 431.2 (+Na); HRMS (ES +ve), C$_{22}$H$_{33}$N$_8$ [M+H]$^+$: calculated 409.28227, found 409.282102.

1-[2-[4-(dimethylamino)-1-piperidyl]ethyl]-3-(p-tolyl)pyrazolo[3,4-d]pyramidin-4-amine (109)

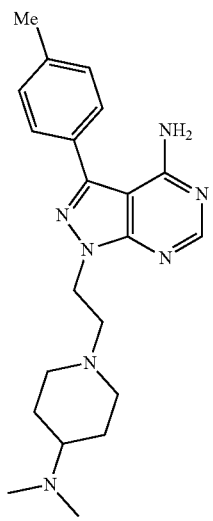 [SMILES: Cc1ccc(-c2nn(CCN3CCC(N(C)C)CC3)c3ncnc(N)c23)cc1]

Purified by column chromatography (MeOH/DCM 10%-10% MeOH with 20 drops of NH$_3$ aq. per 50 ml) to give a light brown solid (13 mg, 0.034 mmol, 32.7%). $^1$H NMR (500 MHz, CDCl$_3$) δ 8.35 (s, 1H), 7.56 (d, J=8.0, 2H), 7.33 (d, J=7.8, 2H), 5.68 (s, 2H), 4.54 (t, J=7.0, 2H), 3.08 (d, J=11.8, 2H), 2.93 (t, J=7.0, 2H), 2.43 (s, 3H), 2.41 (m, 1H), 2.40 (s, 6H), 2.10 (dd, J=11.8, 9.9, 2H), 1.84 (d, J=12.3, 2H), 1.52 (qd, J=12.1, 3.7, 2H); $^{13}$C NMR (126 MHz, CDCl$_3$) δ 158.16 (C), 156.04 (CH), 154.87 (C), 144.69 (C), 139.38 (C), 130.60 (C), 130.32 (CH), 128.57 (CH), 98.70 (C), 62.72 (CH), 56.96 (CH$_2$), 52.86 (2×CH$_2$), 45.13 (CH$_2$), 41.01 (2×CH$_3$), 27.71 (CH$_2$), 21.61 (CH$_3$); MS (ES +ve) [M+1]$^+$: 380.2, 402.1 (+Na); HRMS (ES +ve), C$_{21}$H$_{30}$N$_7$ [M+H]$^+$: calculated 380.25572, found 380.255345.

1-[2-[4-(dimethylaminomethyl)-1-piperidyl]ethyl]-3-(p-tolyl)pyrazolo[3,4-d]pyrimidin-4-amine (112)

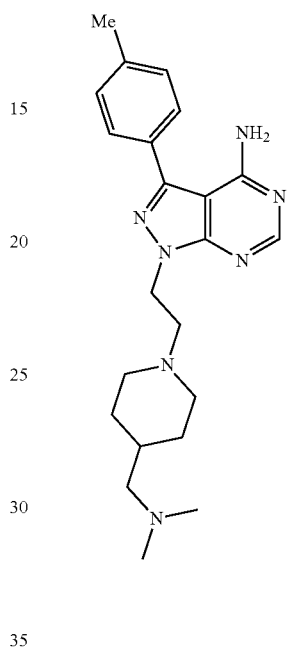

To a suspension of 2-[4-amino-3-(p-tolyl)pyrazolo[3,4-d]pyrimidin-1-yl]acetaldehyde (100 mg, 0.374 mmol) in DCM (2 ml) was added N,N-Dimethyl-1-piperidin-4-ylmethanamine (1 eq. 53.2 mg, 0.374 mmol) and a drop of AcOH and the mixture allowed to stir for 10 mins. Sodium triacetoxyborohydride (79.3 mg, 0.374 mmol) was then added and the mixture allowed to stir for 18 hours. The mixture was reduced in vacuo and purified, without a work up, by column chromatography MeOH/DCM (0-10%-10% with 10 drops NH3 aq. per 100 ml) to give a light orange solid (48 mg, 0.122 mmol, 32.6%). 1H NMR (500 MHz, CDCl3) δ 8.30 (s, 1H), 7.55 (d, J=8.1, 2H), 7.32 (d, J=7.8, 2H), 4.54 (t, J=6.8, 2H), 3.04 (d, J=11.6, 2H), 2.95 (t, J=6.8, 2H), 2.57 (s, 8H), 2.41 (s, 3H), 2.11 (t, J=10.9, 2H), 1.74 (d, J=12.6, 2H), 1.63 (s, 2H), 1.26 (m, 3H); 13C NMR (126 MHz, CDCl3) δ 158.06 (C), 155.40 (CH), 154.56 (C), 144.79 (C), 139.23 (C), 130.36 (C), 130.16 (CH), 128.40 (CH), 98.53 (C), 64.32 (CH2), 56.97 (CH2), 53.15 (CH2), 44.52 (CH2), 44.42 (CH3), 32.62 (CH), 30.14 (CH2), 21.44 (CH3); MS (ES +ve) [M+1]+: 394.3, 416.2 (+Na); HRMS (ES +ve), C$_{22}$H$_{32}$N$_7$ [M+H]+: calculated 394.27137, found 394.271595.

1-[2-[4-(2-dimethylaminoethyl)-1-piperidyl]ethyl]-3-(p-tolyl)pyrazolo[3,4-d]pyrimidin-4-amine (113)

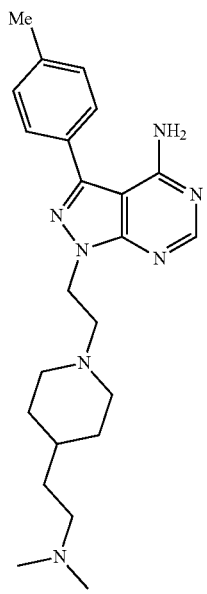 [SMILES: Cc1ccc(-c2nn(CCN3CCC(CCN(C)C)CC3)c3ncnc(N)c23)cc1]

To a suspension of 2-[4-amino-3-(p-tolyl)pyrazolo[3,4-d]pyrimidin-1-yl]acetaldehyde (100 mg, 0.374 mmol) in DCM (2 ml) was added dimethyl-(2-piperidin-4-yl-ethyl)-amine (1 eq. 58.4 mg, 0.374 mmol) and a drop of AcOH and the mixture allowed to stir for 10 mins. Sodium triacetoxyborohydride (79.3 mg, 0.374 mmol) was then added and the mixture allowed to stir for 18 hours. The mixture was reduced in vacuo and purified, without a work up, by column chromatography MeOH/DCM (0-10%-10% with 0-10 drops $NH_3$ aq per 100 ml) to give a light yellow solid (69.8 mg, 0.171 mmol, 45.8). $^1$H NMR (500 MHz, MeOD) δ 8.25 (s, 1H), 7.59-7.55 (m, 2H), 7.38 (d, J=7.8, 2H), 4.58 (t, J=6.6, 2H), 3.14 (d, J=11.8, 2H), 3.09-2.99 (m, 4H), 2.79 (s, 6H), 2.43 (s, 3H), 2.23 (t, J=11.0, 2H), 1.74 (d, J=12.9, 2H), 1.65-1.57 (m, 2H), 1.44-1.36 (m, 1H), 1.27 (dd, J=21.1, 11.8, 2H); $^{13}$C NMR (126 MHz, MeOD) δ 158.50 (C). 155.45 (CH), 154.14 (C), 145.30 (C), 139.23 (C), 129.79 (C), 129.60 (CH), 128.09 (CH), 97.83 (C), 56.50 ($CH_2$), 55.70 ($CH_2$), 52.99 (2×$CH_2$), 43.45 ($CH_2$), 42.14 (2×$CH_3$), 32.84 (CH), 30.88 (2×$CH_2$), 30.64 ($CH_2$), 19.97 ($CH_3$); MS (ES +ve) [M+1]$^+$: 408.1; HRMS (ES +ve), $C_{23}H_{34}N_7$ [M+H]$^+$: calculated 408.28702, found 408.286812.

Compound Intermediates for 021-030:

To a solution of 1-(2,2-diethoxyethyl)-3-iodo-pyrazolo[3,4-d]pyrimidin-4-amine (100 mg, 0.265 mmol) in dioxane/water (4.5 ml/0.5 ml) was added either 1H-pyrrolo[2,3-b]pyridine-5-boronic acid pinicol ester, 5-isoquinolineboronicacid, 3,4-dimethoxyphenylboronicacid, 3-hydroxyphenylboronicacid or furan-3-boronicacid (1.5 eq., 0.397 mmol), potassium carbonate (1.5 eq., 54.8 mg, 0.397 mmol), triphenylphosphine (20 mol %, 20.8 mg) and palladium acetate (5 mol %, 4.5 mg) and the mixture heated in the microwave at 120° C. for an hour. EtOAc (50 ml) and water (50 ml) were added to the mixture and the organic layer separated, washed with brine (50 ml), dried over $MgSO_4$ and concentrated in vacuo.

1-(2,2-diethoxyethyl)-3-(1H-pyrrolo[2,3-b]pyridin-5-yl)pyrazolo[3,4-d]pyrimidin-4-amine

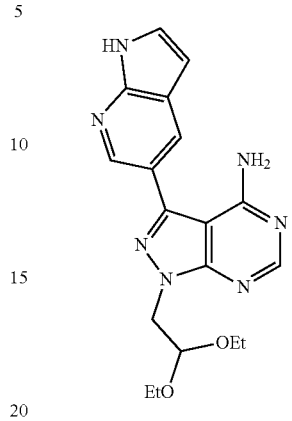

Purified by column chromatography, MeOH/DCM (0-6%) to give a white solid (93 mg, 0.253 mmol, 95.6%). $^1$H NMR (500 MHz, CDCl3) δ 9.53 (s, 1H), 8.62 (d, J=1.9, 1H), 8.41 (s, 1H), 8.24 (d, J=2.0, 1H), 7.45 (d, J=3.4, 1H), 6.62 (d, J=3.5, 1H), 6.29-5.86 (br. s, 2H), 5.14 (t, J=5.7, 1H), 4.62 (d, J=5.7, 2H), 3.79 (dq, J=9.4, 7.0, 2H), 3.55 (dq, J=9.4, 7.0, 2H), 1.14 (t, J=7.0, 6H); $^{13}$C NMR (126 MHz, CDCl3) δ 156.75 (C), 154.58 (C), 153.42 (CH), 148.87 (C), 143.78 (C), 142.83 (CH), 128.83 (CH), 126.85 (CH), 121.30 (C), 120.46 (C), 101.80 (CH), 99.93 (CH), 98.47 (C), 62.17 (2×$CH_2$), 49.33 ($CH_2$), 15.34 (2×$CH_3$); MS (ES +ve) [M+H]$^+$: 368.2, 390.2 (+Na), (ES -ve) [M-H]$^-$: 366.2; HRMS (ES +ve), $C_{18}H_{22}N_7O_2$ (M+H)$^+$: calculated 368.18295, found 368.18090.

1-(2,2-diethoxyethyl)-3-(6-quinolyl)pyrazolo[3,4-d]pyrimidin-4-amine

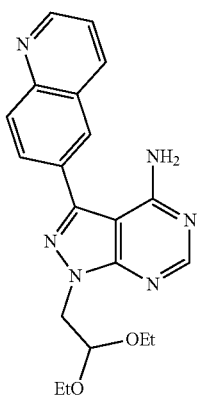 [SMILES: CCOC(Cn1nc(-c2ccc3ncccc3c2)c2c(N)ncnc21)OCC]

Purified by column chromatography, MeOH/DCM (0-5%) to give a pale orange solid (86 mg, 0.227 mmol, 85.8%). $^1$H NMR (400 MHz, CDCl3) δ 9.39 (s, 1H), 8.59 (d, J=6.0, 1H), 8.47 (s, 1H), 8.16 (d, J=8.2, 1H), 7.93 (dd, J=7.1, 1.2, 1H), 7.84 (d, J=6.0, 1H), 7.79 (dd, J=8.2, 7.2, 1H), 5.18 (t, J=5.7, 1H), 4.68 (d, J=5.8, 2H), 3.83 (dq, J=9.4, 7.0, 2H), 3.58 (dq, J=9.4, 7.0, 2H), 1.21-1.13 (m, 6H); $^{13}$C NMR (126 MHz, CDCl3) δ 157.36 (C), 155.87 (CH), 154.77 (C), 152.99 (CH), 144.34 (CH), 141.21 (C), 134.32 (C), 132.29 (CH), 129.43 (CH), 129.32 (C), 128.98 (C), 127.01 (CH), 118.25 (CH), 99.92 (C), 99.80 (CH), 61.94 (2×CH$_2$), 49.18 (CH$_2$), 15.23 (2×CH$_3$); MS (ES +ve) [M+H]$^+$: 379.2, 401.2 (+Na), (ES −ve) [M−H]$^-$: 377.2; HRMS (ES +ve), C$_{20}$H$_{23}$N$_6$O$_2$ (M+H)$^+$: calculated 379.18770, found 379.18660.

1-(2,2-diethoxyethyl)-3-(3,4-dimethoxyphenyl)pyrazolo[3,4-d]pyrimidin-4-amine

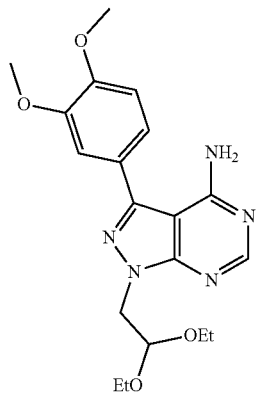 [SMILES: CCOC(Cn1nc(-c2ccc(OC)c(OC)c2)c2c(N)ncnc21)OCC]

Purified by column chromatography, MeOH/DCM (0-2%) to give a pale yellow solid (97 mg, 0.251 mmol, 94.5%). $^1$H NMR (500 MHz, CDCl3) δ 8.38 (s, 1H), 7.23-7.19 (m, 2H), 7.02 (d, J=8.7, 1H), 5.94 (s, 2H), 5.12 (t, J=5.7, 1H), 4.57 (d, J=5.8, 2H), 3.97 (d, J=9.8, 6H), 3.78 (dq, J=9.4, 7.0, 2H), 3.53 (dq, J=9.4, 7.0, 2H), 1.13 (t, J=7.0, 6H); $^{13}$C NMR (126 MHz, CDCl3) δ 157.59 (C), 155.28 (CH), 154.78 (C), 149.94 (C), 149.69 (C), 144.70 (C), 125.68 (C), 120.81 (CH), 111.61 (CH), 111.56 (CH), 99.82 (CH), 98.32 (C), 61.81 (2×CH$_2$), 56.06 (2×CH$_3$), 48.88 (CH$_2$), 15.19 (2×CH); MS (ES +ve) [M+H]$^+$: 388.2, (ES −ve) [M−H]$^-$: 368.2; HRMS (ES +ve), C$_{19}$H$_{26}$N$_5$O$_4$ (M+H)$^+$: calculated 388.19793, found 388.19620.

3-[4-amino-1-(2,2-diethoxyethyl)pyrazolo[3,4-d]pyrimidin-3-yl]phenol

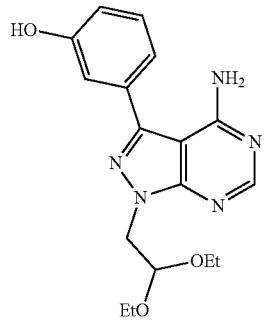 [SMILES: CCOC(Cn1nc(-c2cccc(O)c2)c2c(N)ncnc21)OCC]

Purified by column chromatography, MeOH/DCM (0-3%) to give a cream solid (80 mg, 0.233 mmol, 88.0%). $^1$H NMR (500 MHz, CDCl3) δ 8.45 (s, 1H), 7.38 (t, J=7.9, 1H), 7.20 (d, J=7.5, 1H), 7.12 (s, 1H), 6.95 (d, J=8.1, 1H), 5.89 (s, 2H), 5.10 (t, J=5.7, 1H), 4.57 (d, J=5.7, 2H), 3.76 (tt, J=14.1, 7.0, 2H), 3.52 (tt, J=14.1, 7.0, 2H), 1.11 (t, J=7.0, 6H); $^{13}$C NMR (126 MHz, CDCl3) δ 157.10 (C), 155.85 (CH), 153.86 (C), 152.23 (C), 145.53 (C), 133.41 (C), 131.04 (CH), 120.31 (CH), 117.10 (CH), 115.15 (CH), 99.75 (CH), 97.78 (C), 62.16 (2×CH$_2$), 49.22 (CH$_2$), 15.17 (2×CH$_3$); MS (ES +ve) [M+H]$^+$: 344.2, 366.2 (+Na), (ES −ve) [M−H]$^-$: 342.2; HRMS (ES +ve), C$_{17}$H$_{22}$N$_5$O$_3$ (M+H)$^+$: calculated 344.17172, found 344.17000.

1-(2,2-diethoxyethyl)-3-(3-furyl)pyrazolo[3,4-d]pyrimidin-4-amine

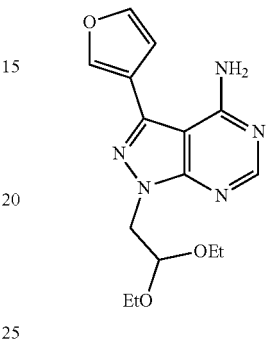

Purified by column chromatography, MeOH/DCM (0-2%) to give a cream coloured solid, (66.8 mg, 0.211 mmol, 79.5%). $^1$H NMR (500 MHz, CDCl3) δ 8.38 (s, 1H), 7.83 (dd, J=1.4, 0.9, 1H), 7.61 (t, J=1.7, 1H), 6.77 (dd, J=1.8, 0.8, 1H), 5.82 (s, 2H), 5.09 (t, J=5.8, 1H), 4.55 (d, J=5.8, 2H), 3.76 (dq, J=9.4, 7.0, 2H), 3.52 (dq, J=9.4, 7.0, 2H), 1.11 (t, J=7.0, 6H); $^{13}$C NMR (126 MHz, CDCl3) δ 156.93 (C), 154.38 (C), 154.12 (CH), 144.66 (CH), 141.11 (CH), 136.98 (C), 118.52 (C), 110.29 (CH), 99.73 (CH), 98.61 (C), 61.92 (2×CH2), 49.04 (CH2), 15.17 (2×CH3); MS (ES +ve) [M+H]$^+$: 318.2, 340.2 (+Na), 657.2 (2M+Na), (ES −ve) [M−H]$^-$: 317.2; HRMS (ES +ve), C$_{15}$H$_{20}$N$_5$O$_3$ (M+H)$^+$: calculated 318.15607, found 318.15400.

1-(2,2-diethoxyethyl)-3-(2-phenylethynyl)pyrazolo[3,4-d]pyrimidin-4-amine

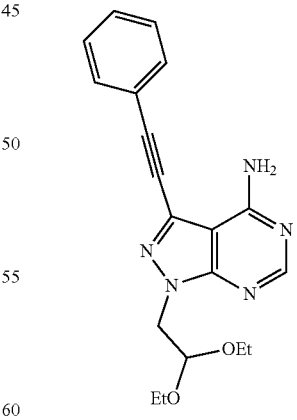

To a solution of 1-(2,2-diethoxyethyl)-3-iodo-pyrazolo[3,4-d]pyrimidin-4-amine (100 mg, 0.265 mmol) in THF (5 ml) was added phenylacetylene (1.5 eq., 0.397 mmol, 40.5 mg, 37.7 μl), triethylamine (1.5 eq., 0.397 mmol, 29.1 μl), palladium acetate (5 mol %, 4.5 mg), triphenylphosphine (20 mol %, 20.8 mg) and copper iodide (5 mol %, 2.5 mg).

The mixture was heated conventionally at 70° C. for 2 hours. EtOAc and water were added to the mixture and the organic layer separated, dried over MgSO$_4$ and concentrated in vacuo. The crude product was purified by column chromatography, MeOH/DCM (0-2%) to give a light yellow solid (52 mg, 0.148 mmol, 55.9%). $^1$H NMR (500 MHz, CDCl3) δ 8.90-8.35 (m, 1H), 7.59 (dd, J=7.7, 1.7, 2H), 7.45-7.36 (m, 3H), 6.20 (s, 2H), 5.09 (t, J=5.6, 1H), 4.53 (d, J=5.7, 2H), 3.74 (dq, J=9.3, 7.0, 2H), 3.50 (dq, J=14.4, 7.2, 2H), 1.10 (t, J=7.0, 6H); $^{13}$C NMR (126 MHz, CDCl3) δ 153.88 (CH), 131.82 (2×CH), 129.58 (CH), 128.67 (2×CH), 121.45 (C), 99.81 (CH), 94.33 (C), 80.63 (C), 62.07 (2×CH$_2$), 49.41 (CH$_2$), 15.16 (2×CH$_3$); MS (ES +ve) [M+H]$^+$: 352.2, 725.2 (2M+Na), (ES −ve) [M−H]$^−$: 350.2; HRMS (ES +ve), C$_{19}$H$_{22}$N$_5$O$_2$ (M+H)$^+$: calculated 352.17680, found 352.17680.

1-[2-[4-(dimethylaminomethyl)-1-piperidyl]ethyl]-3-(1H-pyrrolo[2,3-b]pyridin-5-yl)pyrazolo[3,4-d]pyrimidin-4-amine (221)

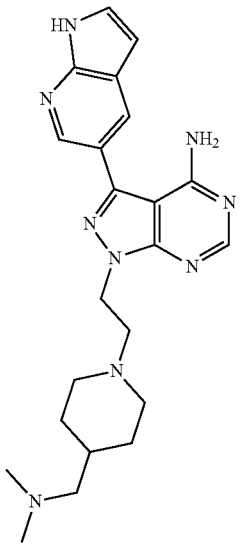 [SMILES: CN(C)CC1CCN(CCn2nc(-c3cnc4[nH]ccc4c3)c3c(N)ncnc32)CC1]

60 mg, 0.163 mmol, of 1-(2,2-diethoxyethyl)-3-(1H-pyrrolo[2,3-b]pyridin-5-yl)pyrazolo[3,4-d]pyrimidin-4-amine was added to a 20 ml microwave vial. 5 ml of water was added followed by 5 ml of TFA and the mixture heated conventially at 100° C. for an hour. The mixture was concentrated in vacuo to leave a light brown oil which was used without further purification 0.163 mmol of 2-[4-amino-3-(1H-pyrrolo[2,3-b]pyridin-5-yl)pyrazolo[3,4-d]pyrimidin-1-yl]acetaldehyde was dissolved in 2 ml of DCM, N,N-dimethyl-1-(4-piperidyl)methanamine (1.5 eq., 0.245 mmol, 34.8 mg) was added followed by a drop of acetic acid. The mixture was allowed to stir for 10 mins then sodium triacetoxyborohydride (1.5 eq., 0.245 mmol, 51.9 mg) added and the mixture allowed to stir for 2 hours. The mixture was concentrated in vacuo and the product purified by column chromatography, MeOH/DCM (5-10% then 10% with 5-20 drops of NH$_3$ aq. Per 100 ml) to give a light orange solid, (15.3 mg, 0.0365 mmol, 14.9%). $^1$H NMR (500 MHz, MeOD) δ 8.52 (s, 1H), 8.29 (d, J=2.0, 1H), 8.28 (s, 1H), 7.52 (d, J=3.5, 1H), 6.62 (d, J=3.5, 1H), 4.64 (t, J=6.4, 2H), 3.25 (d, J=11.7, 2H), 3.13 (t, J=6.3, 2H), 2.96 (t, J=7.2, 2H), 2.84 (s, 6H), 2.37 (t, J=11.4, 2H), 1.88 (m, 1H), 1.80 (d, J=13.1, 2H), 1.36-1.31 (m, 2H); $^{13}$C NMR (126 MHz, MeOD) δ 161.79 (C), 158.65 (C), 155.54 (CH), 154.33 (C), 148.16 (C), 143.72 (C), 141.84 (CH), 128.67 (CH), 127.12 (CH), 120.73 (C), 100.63 (CH), 98.19 (C), 62.67 (CH$_2$), 56.31 (CH$_2$), 52.22 (2×CH$_2$), 43.41 (CH$_2$), 42.72 (2×CH$_3$), 30.93 (CH), 28.39 (2×CH$_2$); MS (ES +ve) [M+H]$^+$: 420.2; HRMS (ES +ve), C$_{22}$H$_{29}$N$_9$ [M+H]$^+$: calculated 420.25404, found 420.254249.

1-[2-[4-(dimethylaminomethyl)-1-piperidyl]ethyl]-3-(6-quinolyl)pyrazolo[3,4-d]pyrimidin-4-amine (223)

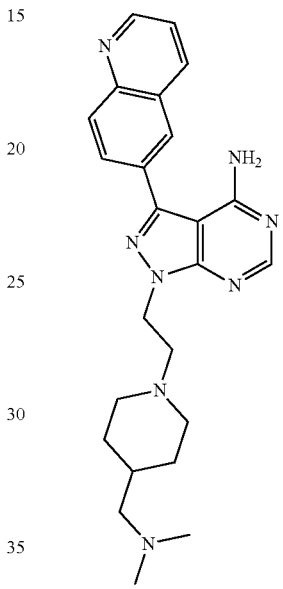

60 mg, 0.159 mmol of 1-(2,2-diethoxyethyl)-3-(6-quinolyl)pyrazolo[3,4-d]pyrimidin-4-amine was added to a 20 ml microwave vial. 5 ml of water was added followed by 5 ml of TFA and the mixture heated conventially at 100° C. for an hour. The mixture was concentrated in vacuo to give a brown oil which was used without further purification. 0.159 mmol of 2-[4-amino-3-(6-quinolyl)pyrazolo[3,4-d]pyrimidin-1-yl]acetaldehyde was dissolved in 2 ml of DCM. N,N-dimethyl-1-(4-piperidyl)methanamine (1.5 eq., 0.238 mmol, 33.9 mg) was added followed by a drop of acetic acid and the mixture allowed to stir for 10 mins. Sodium triacetoxyborohydride (1.5 eq., 0.238 mmol, 50.4 mg) was added and the mixture allowed to stir for 17 hours. The mixture was concentrated in vacuo and purified by column chromatography, MeOH/DCM (5-10% then 20 drops NH$_3$ aq per 100 ml) to give a fluorescent yellow coloured solid, 48.9 mg, 0.122 mmol, 70.6%. $^1$H NMR (500 MHz, MeOD) δ 9.37 (s, 1H), 8.47 (d, J=6.0, 1H), 8.31 (m, 2H), 7.99 (dd, J=7.1, 1.2, 1H), 7.90-7.84 (m, 2H), 4.65 (t, J=6.7, 2H), 3.09 (d, J=11.7, 2H), 2.99 (t, J=6.7, 2H), 2.28 (s, 6H), 2.27 (m, 2H), 2.18-2.11 (m, 2H), 1.75 (d, J=12.4, 2H), 1.57 (ddd, J=11.3, 7.4, 3.9, 1H), 1.24-1.12 (m, 2H); $^{13}$C NMR (126 MHz, MeOD) δ 158.26 (C), 155.67 (CH), 154.06 (C), 152.47 (CH), 142.47 (CH), 141.58 (C), 134.67 (C), 132.89 (CH), 129.35 (CH), 129.21 (c), 129.11 (C), 127.33 (CH), 118.82 (CH), 99.55 (C), 65.35 (CH$_2$), 56.79 (CH$_2$), 53.22 (2×CH$_2$), 44.34 (2×CH$_3$), 44.05 (CH$_2$), 33.06 (CH), 30.04 (2×CH$_2$); MS (ES +ve) [M+H]$^+$: 431.2; HRMS (ES +ve), C$_{24}$H$_{30}$N$_9$ [M+H]$^+$: calculated 431.25879, found 431.258695.

3-(3,4-dimethoxyphenyl)-1-[2-[4-(dimethylaminomethyl)-1-piperidyl]ethyl]pyrazolo[3,4-d]pyrimidin-4-amine (224)

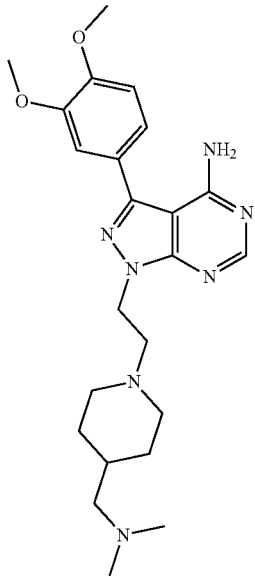 [SMILES: COc1ccc(-c2nn(CCN3CCC(CN(C)C)CC3)c3ncnc(N)c23)cc1OC]

70 mg, 0.181 mmol of 1-(2,2-diethoxyethyl)-3-(3,4-dimethoxyphenyl)pyrazolo[3,4-d]pyrimidin-4-amine was added to a 20 ml microwave vial. 5 ml of water was added followed by 5 ml of TFA and the mixture heated conventially at 100° C. for an hour. The mixture was concentrated in vacuo to leave a light brown oil which was used without further purification. 0.181 mmol of 2-[4-amino-3-(3,4-dimethoxyphenyl)pyrazolo[3,4-d]pyrimidin-1-yl]acetaldehyde was dissolved in 4 ml of DCM. N,N-dimethyl-1-(4-piperidyl)methanamine (1.5 eq., 0.271 mmol, 38.5 mg) was added followed by a drop of acetic acid and the mixture allowed to stir for 10 mins. Sodium triacetoxyborohydride (1.5 eq., 0.271 mmol, 57.4 mg) was added and the mixture allowed to stir for 17 hours. The mixture was concentrated in vacuo and the product purified by column chromatography, MeOH/DCM (5-10% then 10 drops of NH$_3$ aq per 100 ml) to give a light yellow solid (14.5 mg, 0.033 mmol, 20.8%). $^1$H NMR (500 MHz, MeOD) δ 8.26 (s, 1H), 7.27 (s, 1H), 7.25 (d, J=8.2, 1H), 7.14 (d, J=8.2, 1H), 4.63 (t, J=6.3, 2H), 3.91 (s, 6H), 3.18 (s, 2H), 2.98 (d, J=7.2, 2H), 2.85 (s, 6H), 2.45 (m, 2H), 1.92 (m, 1H), 1.83 (d, J=13.2, 2H), 1.35 (dd, J=22.2, 11.5, 2H); $^{13}$C NMR (126 MHz, MeOD) δ 158.58 (C), 155.51 (CH), 154.22 (C), 150.22 (C), 149.67 (C), 145.44 (C), 125.19 (C), 120.91 (CH), 111.94 (CH), 111.73 (CH), 97.82 (C), 62.49 (CH$_2$), 56.18 (CH$_2$), 55.13 (2×CH$_3$), 52.16 (2×CH$_2$), 43.08 (CH$_2$), 42.69 (2×CH$_3$), 30.70 (CH), 28.13 (2×CH$_2$); MS (ES +ve) [M+H]$^+$: 440.2; HRMS (ES +ve), C$_{23}$H$_{33}$N$_7$O$_2$ [M+H]$^+$: calculated 440.26902, found 440.268379.

3-[4-amino-1-[2-[4-(dimethylaminomethyl)-1-piperidyl]ethyl]pyrazolo[3,4-d]pyrimidin-3-yl]phenol (225)

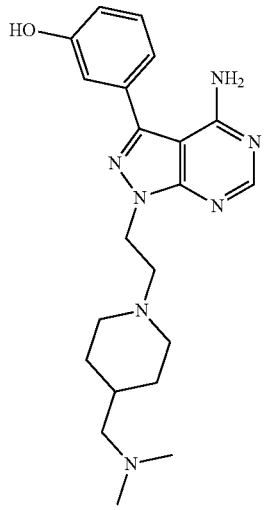 [SMILES: CN(C)CC1CCN(CCn2nc(-c3cccc(O)c3)c3c(N)ncnc32)CC1]

60 mg, 0.175 mmol of 3-[4-amino-1-(2,2-diethoxyethyl)pyrazolo[3,4-d]pyrimidin-3-yl]phenol was added to a 20 ml microwave vial. 5 ml of water was added followed by 5 ml of TFA and the mixture heated conventially at 100° C. for an hour. The mixture was concentrated in vacuo to leave a light brown oil which was used without further purification. 0.175 mmol of 2-[4-amino-3-(3-hydroxyphenyl)pyrazolo[3,4-d]pyrimidin-1-yl]acetaldehyde was dissolved in 4 ml of DCM. N,N-dimethyl-1-(4-piperidyl)methanamine (1.5 eq., 0.262 mmol, 37.2 mg) was added followed by a drop of acetic acid and the mixture allowed to stir for 10 mins. Sodium triacetoxyborohydride (1.5 eq., 0.262 mmol, 55.5 mg) was added and the mixture allowed to stir for 20 hours. The mixture was concentrated in vacuo and the product purified by column chromatography, MeOH/DCM (10% then 0-20 drops of NH$_3$ aq per 100 ml) to give a dark orange solid (5.5 mg, 0.0139 mmol, 8.0%). $^1$H NMR (500 MHz, MeOD) δ 8.26 (s, 1H), 7.39 (t, J=7.9, 1H), 7.17-7.09 (m, 2H), 6.95 (dd, J=7.8, 2.1, 1H), 4.57 (t, J=6.7, 2H), 3.08 (d, J=11.7, 2H), 2.96 (t, J=6.7, 2H), 2.47 (m, 8H), 2.16 (t, J=11.0, 2H), 1.74 (d, J=12.9, 2H), 1.64 (m, 1H), 1.21 (dd, J=21.1, 12.0, 2H); $^{13}$C NMR (126 MHz, MeOD) δ 158.44 (C), 158.06 (C), 155.42 (CH), 154.06 (C), 145.17 (C), 133.97 (C), 130.16 (CH), 119.09 (CH), 115.96 (CH), 114.92 (CH), 97.73 (C), 64.57 (CH$_2$), 56.66 (CH$_2$), 52.78 (2×CH$_2$), 43.83 (2×CH$_3$), 43.77 (CH$_2$), 32.46 (CH), 29.58 (2×CH$_2$). MS (ES +ve) [M+H]$^+$: 396.4; HRMS (ES +ve), C$_{21}$H$_{29}$N$_7$O [M+H]$^+$: calculated 396.24281, found 396.242971.

51

1-[2-[4-(dimethylaminomethyl)-1-piperidyl]ethyl]-3-(3-furyl)pyrazolo[3,4-d]pyrimidin-4-amine (226)

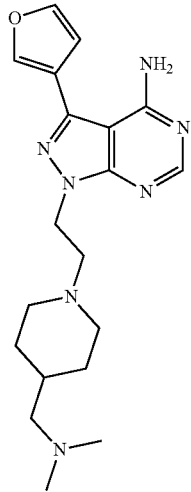 [SMILES: CN(C)CC1CCN(CCn2nc(-c3ccoc3)c3c(N)ncnc32)CC1]

52 mg, 0.164 mmol of 1-(2,2-diethoxyethyl)-3-(3-furyl)pyrazolo[3,4-d]pyrimidin-4-amine was added to a 20 ml microwave vial. 5 ml of water was added followed by 5 ml of TFA and the mixture heated conventially at 100° C. for an hour. The mixture was concentrated in vacuo to leave a light brown oil which was used without further purification. 0.164 mmol of 2-[4-amino-3-(3-furyl)pyrazolo[3,4-d]pyrimidin-1-yl]acetaldehyde was dissolved in 4 ml of DCM. N,N-dimethyl-1-(4-piperidyl)methanamine (1.5 eq., 0.246 mmol, 35.0 mg) was added followed by a drop of acetic acid and the mixture allowed to stir for 10 mins. Sodium triacetoxyborohydride (1.5 eq., 0.246 mmol, 52.1 mg) was added and the mixture allowed to stir over the weekend. The mixture was concentrated in vacuo and the product purified by column chromatography, MeOH/DCM (5-10% then 10-20 drops of $NH_3$ aq per 100 ml) to give a dark golden brown solid (45.7 mg, 0.124 mmol, 75.5%). $^1$H NMR (500 MHz, MeOD) δ 8.23 (s, 1H), 7.96 (dd, J=1.4, 0.9, 1H), 7.71 (t, J=1.7, 1H), 6.82 (dd, J=1.8, 0.8, 1H), 4.53 (t, J=6.7, 2H), 3.08 (d, J=11.7, 2H), 2.94 (t, J=6.7, 2H), 2.62 (d, J=6.6, 2H), 2.57 (s, 6H), 2.16 (dd, J=11.8, 10.0, 2H), 1.72 (d, J=12.9, 2H), 1.68 (m, 1H), 1.26-1.18 (m, 2H); $^{13}$C NMR (126 MHz, MeOD) δ 158.57 (C), 155.45 (CH), 153.98 (C), 144.34 (CH), 141.47 (CH), 137.22 (C), 118.30 (C), 109.73 (CH), 98.17 (C), 63.97 ($CH_2$), 56.59 ($CH_2$), 52.62 (2×$CH_2$), 43.73 ($CH_2$), 43.43 (2×$CH_3$), 32.02 (CH), 29.27 (2×$CH_2$); MS (ES +ve) [M+H]$^+$: 370.2; HRMS (ES +ve), $C_{19}H_{27}N_7O$ [M+H]$^+$: calculated 370.22716, found 370.227049.

52

1-[2-[4-(dimethylaminomethyl)-1-piperidyl]ethyl]-3-(2-phenylethynyl)pyrazolo[3,4-d]pyrimidin-4-amine (230)

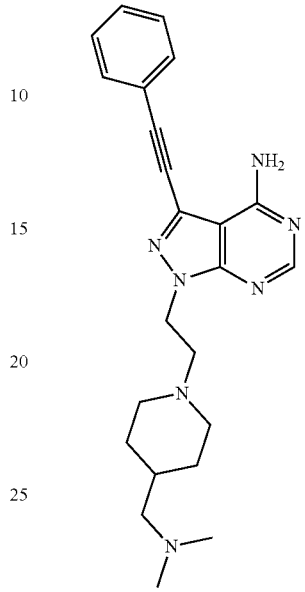

50 mg, 0.142 mmol of 1-(2,2-diethoxyethyl)-3-(2-phenylethynyl)pyrazolo[3,4-d]pyrimidin-4-amine was added to a 20 ml microwave vial. 5 ml of water was added followed by 5 ml of TFA and the mixture heated conventially at 100° C. for an hour. The mixture was concentrated in vacuo to leave a dark brown oil which was used without further purification. 0.142 mmol of 2-[4-amino-3-(2-phenylethynyl)pyrazolo[3,4-d]pyrimidin-1-yl]acetaldehyde was suspended in 4 ml of DCM. N,N-dimethyl-1-(4-piperidyl)methanamine (1.5 eq., 0.213 mmol, 30.3 mg) was added followed by a drop of acetic acid and the mixture allowed to stir for 10 mins. Sodium triacetoxyborohydride (1.5 eq., 0.213 mmol, 45.1 mg) was added and the mixture allowed to stir for an hour. The mixture was concentrated in vacuo and the product purified by column chromatography, MeOH/DCM (5-10% then 5-10 drops of $NH_3$ aq per 100 ml) to give a dark orange solid, (23.4 mg, 0.058 mmol, 40.7%). $^1$H NMR (500 MHz, MeOD) δ 8.23 (s, 1H), 7.69-7.61 (m, 2H), 7.46-7.40 (m, 3H), 4.51 (t, J=6.7, 2H), 3.02 (d, J=11.7, 2H), 2.90 (t, J=6.7, 2H), 2.29 (s, 6H), 2.28-2.25 (m, 2H), 2.10 (td, J=11.8, 2.3, 2H), 1.71 (d, J=12.8, 2H), 1.54 (dtd, J=14.6, 7.5, 3.7, 1H), 1.15 (qd, J=12.5, 3.7, 2H); $^{13}$C NMR (126 MHz, MeOD) δ 158.22 (C), 156.07 (CH), 153.13 (C), 131.48 (CH×2), 129.25 (CH), 128.38 (CH×2), 126.72 (C), 121.47 (C), 100.98 (C), 93.76 (C), 79.88 (C), 65.21 ($CH_2$), 56.68 ($CH_2$), 52.96 ($CH_2$×2), 44.27 ($CH_3$×2), 44.22 ($CH_2$), 32.94 (CH), 29.92 ($CH_2$×2); MS (ES +ve) [M+H]$^+$: 404.3; HRMS (ES +ve), $C_{23}H_{29}N_7$ [M+H]$^+$: calculated 404.24790, found 404.247888.

53

1-[2-[4 (dimethylaminomethyl)-1-piperidyl]ethyl]-3-iodo-pyrazolo[3,4-d]pyrimidin-4-amine (232)

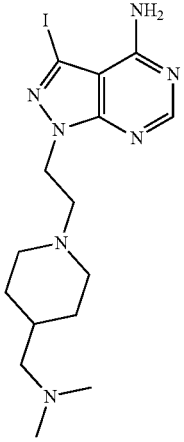 [SMILES: CN(C)CC1CCN(CCn2nc(I)c3c(N)ncnc32)CC1]

75 mg, 0.199 mmol of 1-(2,2-diethoxyethyl)-3-iodo-pyrazolo[3,4-d]pyrimidin-4-amine was added to a 10 ml microwave tube. 2.5 ml of water and 2.5 ml of TFA were added and the mixture heated to 100° C. for an hour. The mixture was concentrated in vacuo to give a white solid which was used without further purification. 0.199 mmol of 2-(4-amino-3-iodo-pyrazolo[3,4-d]pyrimidin-1-yl)acetaldehyde was suspended in 3 ml of DCM. N,N-dimethyl-1-(4-piperidyl)methanamine (1.5 eq., 0.299 mmol, 42.2 mg) was added followed by a drop of acetic acid and the mixture allowed to stir for 10 mins. Sodium triacetoxyborohydride (1.5 eq., 0.299 mmol, 63.4 mg) was added and the mixture allowed to stir for 17 hours. The mixture was concentrated in vacuo and purified by column chromatography, MeOH/DCM (0-10% then 5-15 drops of $NH_3$ aq. per 100 ml) to give a light yellow coloured solid (63.6 mg, 0.148 mmol, 74.5%). $^1$H NMR (500 MHz, MeOD) δ 8.20 (s, 1H), 4.49 (t, J=6.7, 2H), 3.01 (d, J=11.7, 2H), 2.87 (t, J=6.7, 2H), 2.28 (s, 6H), 2.27 (d, 2H), 2.10 (td, J=11.8, 2.3, 2H), 1.72 (d, J=13.0, 2H), 1.55 (ddt, J=15.0, 7.6, 3.8, 1H), 1.15 (qd, J=12.3, 3.7, 2H); $^{13}$C NMR (126 MHz, MeOD) δ 158.05 (C), 155.63 (CH), 153.58 (C), 103.66 (C), 86.95 (C), 65.27 ($CH_2$), 56.73 ($CH_2$), 52.96 (2×$CH_2$), 44.30 (2×$CH_3$), 44.15 ($CH_2$), 32.97 (CH), 30.09 (2×$CH_2$); MS (ES +ve) [M+H]$^+$: 430.2.

54

1-[2-[4-(dimethylamino)-1-piperidyl]ethyl]-3-(1H-pyrrolo[2,3-b]pyridin-5-yl)pyrazolo[3,4-d]pyrimidin-4-amine (402)

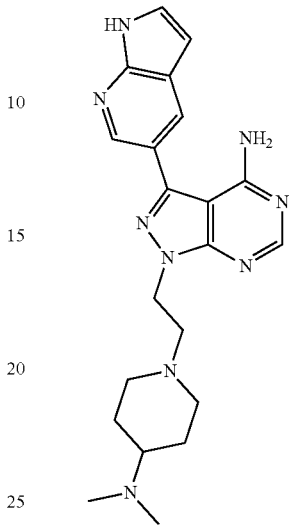

40 mg, 0.109 mmol of 1-(2,2-diethoxyethyl)-3-(1H-pyrrolo[2,3-b]pyridin-5-yl)pyrazolo[3,4-d]pyrimidin-4-amine was added to a 10 ml microwave tube. 2.5 ml of water and 2.5 ml of TFA were then added and the mixture heated to 100° C. for 30 mins in the microwave. The solvents were removed in vacuo to give a dark brown oil which was used without further purification. 0.109 mmol of 2-[4-amino-3-(1H-pyrrolo[2,3-b]pyridin-5-yl)pyrazolo[3,4-d]pyrimidin-1-yl]acetaldehyde was dissolved in 3 ml of THF. N,N-dimethylpiperidine-4-amine (1.5 eq., 0.1635 mmol, 20.9 mg) was added and the mixture was allowed to stir for 5 mins. Sodium triacetoxyborohydride (1.5 eq., 0.1635 mmol, 34.7 mg) was then added and the mixture allowed to stir for an hour. The reaction mixture was concentrated in vacuo and purified by column chromatography, MeOH/DCM (10% then 5-40 drops of $NH_3$ aq. per 50 ml) to give a light yellow solid (26.9 mg, 0.0664 mmol, 60.9%). $^1$H NMR (500 MHz, MeOD) δ 8.50 (d, J=1.9, 1H), 8.28 (d, J=2.0, 1H), 8.27 (s, 1H), 7.51 (d, J=3.5, 1H), 6.62 (d, J=3.5, 1H), 4.56 (t, J=6.4, 2H), 3.19 (d, J=12.1, 2H), 3.06 (tt, J=12.0, 3.9, 1H), 2.97 (t, J=6.4, 2H), 2.77 (s, 6H), 2.18 (t, J=11.1, 2H), 2.00 (d, J=12.4, 2H), 1.58 (qd, J=12.3, 3.9, 2H); $^{13}$C NMR (126 MHz, MeOD) δ 158.64 (C), 155.49 (CH), 154.32 (C), 148.16 (C), 143.50 (C), 141.84 (CH), 128.66 (CH), 127.12 (CH), 120.78 (C), 120.73 (C), 100.63 (CH), 98.08 (C), 63.37 (CH), 55.82 ($CH_2$), 51.54 (2×$CH_2$), 44.11 ($CH_2$), 39.16 (2×$CH_3$), 26.18 (2×$CH_2$); MS (ES +ve) (M+H)$^+$: 406.6; HRMS (ES +ve), $C_{21}H_{28}N_9$ (M+H)$^+$: calculated 406.24622, found 406.24490.

55

1-[2-[4-(dimethylamino)-1-piperidyl]ethyl]-3-iodo-pyrazolo[3,4-d]pyrimidin-4-amine

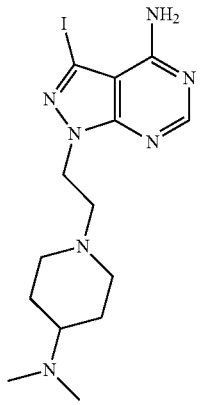 [SMILES: CN(C)C1CCN(CCn2nc(I)c3c(N)ncnc32)CC1]

150 mg, 0.398 mmol, of 1-(2,2-diethoxyethyl)-3-iodo-pyrazolo[3,4-d]pyrimidin-4-amine was added to a 10 ml microwave tube. 2.5 ml of water and 2.5 ml of TFA were added and the mixture heated to 100° C. for an hour. The mixture was concentrated in vacuo to give a white solid which was used without further purification. 0.398 mmol of 2-(4-amino-3-iodo-pyrazolo[3,4-d]pyrimidin-1-yl)acetaldehyde was suspended in 3 ml of DCM. N,N-dimethylpiperidine-4-amine (1.5 eq., 0.598 mmol, 76.6 mg) was added followed by a drop of acetic acid and the mixture allowed to stir for 10 mins. Sodium triacetoxyborohydride (1.5 eq., 0.598 mmol, 126.8 mg) was added and the mixture allowed to stir for 17 hours overnight. The mixture was concentrated in vacuo and the product purified by column chromatography, MeOH/DCM (0-10% then 5-20 drops of $NH_3$ aq. per 100 ml) to give a light orange/brown solid (163.8 mg, 0.405 mmol, 99.1%). $^1$H NMR (500 MHz, MeOD) δ 8.22 (s, 1H), 4.49 (t, J=6.4, 2H), 3.32 (s, 3H), 3.15 (d, J=12.1, 2H), 2.96 (ddd, J=16.0, 8.0, 4.0, 1H), 2.91 (t, J=6.4, 2H), 2.72 (s, 6H), 2.15 (td, J=12.0, 2.0, 2H), 2.04-1.96 (m, 2H), 1.54 (qd, J=12.2, 3.9, 2H); $^{13}$C NMR (126 MHz, MeOD) δ 158.07 (C), 155.67 (CH), 153.70 (C), 103.59 (C), 86.97 (C), 63.18 (CH), 55.86 ($CH_2$), 51.38 (2×$CH_2$), 44.37 ($CH_2$), 39.31 (2×$CH_3$), 26.42 (2×$CH_2$); MS (ES +ve) [M+H]$^+$: 416.2.

56 tert-butyl N-[4-[4-amino-1-[2-[4-(dimethylaminomethyl)-1-piperidyl]ethyl]pyrazolo[3,4-d]pyrimidin-3-yl]-2-methoxy-phenyl]carbamate (503)

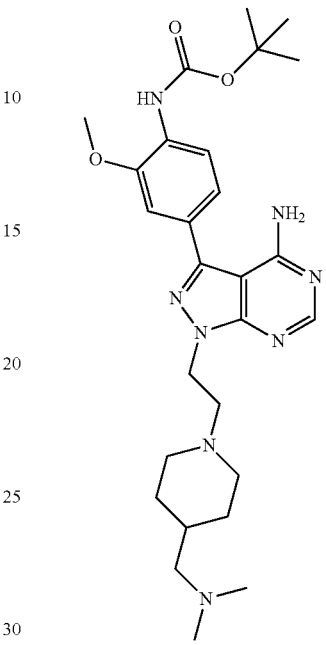

To a solution of 1-[2-[4-(dimethylaminomethyl)-1-piperidyl]ethyl]-3-iodo-pyrazolo[3,4-d]pyrimidin-4-amine (50 mg, 0.1165 mmol) in dioxane/water (4.5 ml/0.5 ml) was added [4-(tert-butoxycarbonylamino)-3-methoxy-phenyl]boronic acid (1.5 eq., 46.7 mg, 0.175 mmol), potassium carbonate (1.5 eq., 24.2 mg, 0.175 mmol) and triphenylphosphine (20 mol %, 9.2 mg) followed by palladium acetate (5 mol %) and the mixture heated in the microwave at 120° C. for 45 mins. EtOAc (50 ml) and water (50 ml) were added to the mixture and the organic layer separated. The aqueous layer was washed with EtOAc (20 ml, ×3) and the organics combined dried over $MgSO_4$ and concentrated in vacuo. The crude product was purified by column chromatography, MeOH/DCM (0-10% then 5-20 drops of $NH_3$ aq. per 100 ml) to give a dark brown solid (36.5 mg, 0.0696 mmol, 59.7%). $^1$H NMR (500 MHz, MeOD) δ 8.27 (s, 1H), 8.08 (d, J=8.2, 1H), 7.30 (d, J=1.8, 1H), 7.26 (dd, J=8.2, 1.8, 1H), 4.58 (t, J=6.8, 2H), 3.98 (s, 3H), 3.08 (d, J=11.7, 2H), 2.96 (t, J=6.8, 2H), 2.34 (s, 6H), 2.32 (d, J=7.2, 2H), 2.16 (dd, J=11.8, 9.6, 2H), 1.76 (d, J=12.3, 2H), 1.63-1.58 (m, 1H), 1.57 (s, 9H), 1.24-1.16 (m, 2H); $^{13}$C NMR (126 MHz, MeOD) δ 158.52 (C), 155.40 (CH), 154.07 (C), 153.46 (C), 149.24 (C), 145.04 (C), 128.77 (C), 127.39 (C), 120.43 (CH), 119.56 (CH), 110.29 (CH), 97.78 (C), 80.18 (C), 65.19 ($CH_2$), 56.76 ($CH_2$), 55.08 ($CH_3$), 52.96 (2×$CH_2$), 44.24 (2×$CH_3$), 43.79 ($CH_2$), 32.92 (CH), 29.89 (2×$CH_2$), 27.22 (3×$CH_3$); MS (ES +ve) [M+H]$^+$: 525.4, (ES −ve) [M−H]$^−$: 523.3; HRMS (ES +ve), $C_{27}H_{41}N_8O_3$ (M+H)$^+$: calculated 525.32961, found 525.32890.

tert-butyl N-[4-[4-amino-1-[2-[4-(dimethylamino)-1-piperidyl]ethyl]pyrazolo[3,4-d]pyrimidin-3-yl]-2-methoxy-phenyl]carbamate (506)

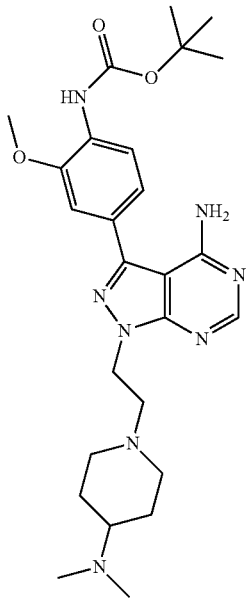

To a solution of 1-[2-[4-(dimethylamino)-1-piperidyl]ethyl]-3-iodo-pyrazolo[3,4-d]pyrimidin-4-amine (50 mg, 0.1205 mmol) in dioxane/water (4.5 ml/0.5 ml) was added [4-(tert-butoxycarbonylamino)-3-methoxy-phenyl]boronic acid (1.5 eq., 48.3 mg, 0.181 mmol), potassium carbonate (1.5 eq., 25.0 mg, 0.181 mmol) and triphenylphosphine (20 mol %, 9.5 mg) followed by palladium acetate (5 mol %) and the mixture heated in the microwave at 120° C. for an hour. EtOAc (50 ml) and water (50 ml) were added to the mixture and the organic layer separated. The aqueous layer was washed with EtOAc (20 ml, ×2) and the organics combined dried over MgSO$_4$ and concentrated in vacuo. The crude product was purified by column chromatography, MeOH/DCM (0-10% then 5-20 drops of NH$_3$ aq. per 100 ml) to give a light brown solid (23.1 mg, 0.0453 mmol, 37.6%). $^1$H NMR (500 MHz, MeOD) δ 8.27 (s, 1H), 8.08 (d, J=8.2, 1H), 7.30 (d, J=1.8, 1H), 7.26 (dd, J=8.2, 1.9, 1H), 4.56 (t, J=6.7, 2H), 3.98 (s, 3H), 3.14 (d, J=11.9, 2H), 2.94 (t, J=6.7, 2H), 2.39 (m, 7H), 2.14 (dd, J=12.0, 10.0, 2H), 1.90 (d, J=12.5, 2H), 1.57 (s, 9H), 1.49 (qd, J=12.1, 3.6, 2H); $^{13}$C NMR (126 MHz, MeOD) δ 158.53 (C), 155.40 (CH), 154.12 (C), 153.46 (C), 149.24 (C), 145.02 (C), 128.78 (C), 127.38 (C), 120.43 (CH), 119.56 (CH), 110.28 (CH), 97.73 (C), 80.18 (C), 62.29 (CH), 56.22 (CH$_2$), 55.07 (CH$_3$), 52.20 (2×CH$_2$), 44.00 (CH$_2$), 40.06 (2×CH$_3$), 27.24 (2×CH$_2$), 27.21 (3×CH$_3$); MS (ES +ve) [M+H]$^+$: 511.3; HRMS (ES +ve), C$_{26}$H$_{38}$N$_8$O$_3$ [M+H]$^+$: calculated 511.31396, found 511.3151.

3-iodo-1-[2-(4-pyrrolidin-1-yl-1-piperidyl)ethyl]pyrazolo[3,4-d]pyrimidin-4-amine

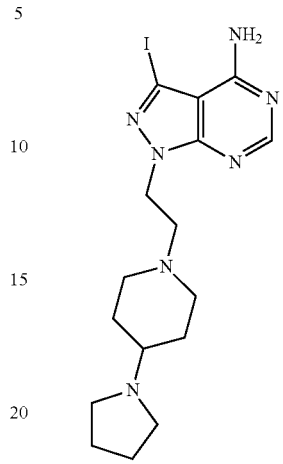

300 mg, 0.8646 mmol of 1-(1,3-dioxolan-2-ylmethyl)-3-iodo-pyrazolo[3,4-d]pyrimidin-4-amine was added to a 10 ml microwave tube. 2.5 ml of water and 2.5 ml of TFA were added and the mixture heated to 100° C. for 3 hours. The product was concentrated in vacuo and used without further purification. 0.432 mmol of 2-(4-amino-3-iodo-pyrazolo[3,4-d]pyrimidin-1-yl)acetaldehyde was suspended in 3 ml of DCM. 4-(1-pyrrolidinyl)piperidine (1.5 eq., 0.648 mmol, 99.9 mg) was added followed by a drop of acetic acid and the mixture allowed to stir for 10 mins. Sodium triacetoxyborohydride (1.5 eq., 0.648 mmol, 137.3 mg) was added and the mixture allowed to stir for 17 hours. The mixture was concentrated in vacuo and purified by column chromatography, MeOH/DCM (0-10%) to give a green/brown solid, (183.1 mg, 0.415 mmol, 96.1%). $^1$H NMR (500 MHz, MeOD) δ 8.22 (s, 1H), 4.50 (t, J=6.3, 2H), 3.34 (m, 4H), 3.12 (d, J=12.0, 2H), 3.06 (dd, J=13.9, 9.7, 1H), 2.90 (t, J=6.3, 2H), 2.21-2.00 (m, 8H), 1.52 (td, J=12.1, 8.1, 2H); MS (ES +ve) (M+H)$^+$: 442.2

3-iodo-1-[2-[4-(1-piperidyl)-1-piperidyl]ethyl]pyrazolo[3,4-d]pyrimidin-4-amine

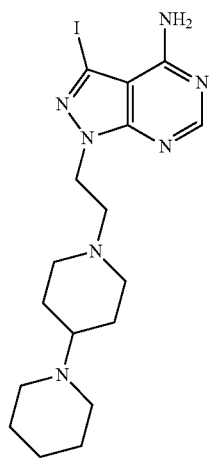 [SMILES: Nc1ncnc2c1c(I)nn2CCN1CCC(N2CCCCC2)CC1]

300 mg, 0.8646 mmol of 1-(1,3-dioxolan-2-ylmethyl)-3-iodo-pyrazolo[3,4-d]pyrimidin-4-amine was added to a 10 ml microwave tube. 2.5 ml of water and 2.5 ml of TFA were added and the mixture heated to 100° C. for 3 hours. The product was concentrated in vacuo and used without further purification. 0.432 mmol of 2-(4-amino-3-iodo-pyrazolo[3,4-d]pyrimidin-1-yl)acetaldehyde was suspended in 3 ml of DCM. 1,4-bipiperidine (1.5 eq., 0.648 mmol, 108.9 mg) was added followed by a drop of acetic acid and the mixture allowed to stir for 10 mins. Sodium triacetoxyborohydride (1.5 eq., 0.648 mmol, 137.3 mg) was added and the mixture allowed to stir for 17 hours. The mixture was concentrated in vacuo and purified by column chromatography, MeOH/DCM (0-10%) to give a dark green/brown thick oil, (191.6 mg, 0.421 mmol, 97.5%). $^1$H NMR (601 MHz, DMSO) δ 8.21 (s, 1H), 4.38 (t, J=6.6, 2H), 2.85 (broad m, 9H), 1.98 (m, 2H), 1.54 (broad m, 10H); MS (ES +ve) (M+H)$^+$: 456.2 tert-butyl N-[4-[4-amino-1-[2-(4-pyrrolidin-1-yl-1-piperidyl)ethyl]pyrazolo[3,4-d]pyrimidin-3-yl]-2-methoxy-phenyl]carbamate (518)

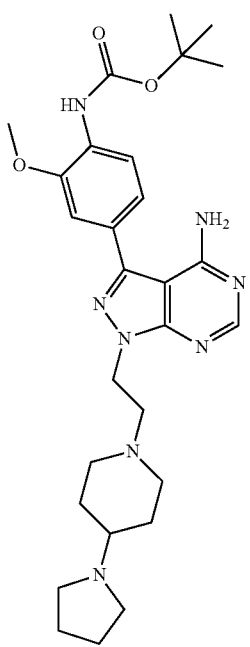 [SMILES: COc1cc(-c2nn(CCN3CCC(N4CCCC4)CC3)c3ncnc(N)c23)ccc1NC(=O)OC(C)(C)C]

To a solution of 3-iodo-1-[2-(4-pyrrolidin-1-yl-1-piperidyl)ethyl]pyrazolo[3,4-d]pyrimidin-4-amine (50 mg, 0.113 mmol) in dioxane/water (4.5 ml/0.5 ml) was added [4-(tert-butoxycarbonylamino)-3-methoxy-phenyl]boronic acid (1.5 eq., 45.4 mg, 0.170 mmol), potassium carbonate (1.5 eq., 23.5 mg, 0.170 mmol) and triphenylphosphine (20 mol %, 8.9 mg) followed by palladium acetate (5 mol %) and the mixture heated in the microwave at 120° C. for an hour. EtOAc (50 ml) and water (50 ml) were added to the mixture and the organic layer separated. The aqueous layer was washed with EtOAc (20 ml, ×2) and the organics combined and washed with brine then dried over MgSO$_4$ and concentrated in vacuo. The crude product was purified by column chromatography, MeOH/DCM (0-10% then 5-25 drops of NH$_3$ aq. per 100 ml) to give a light orange solid (16.69 mg, 31.12 μmol, 27.5%). $^1$H NMR (500 MHz, MeOD) δ 8.27 (s, 1H), 8.08 (d, J=8.2, 1H), 7.30 (d, J=1.8, 1H), 7.25 (dd, J=8.2, 1.8, 1H), 4.56 (t, J=6.6, 2H), 3.98 (s, 3H), 3.12 (d, J=12.0, 2H), 2.94 (m, 6H), 2.53 (m, 1H), 2.15 (t, J=11.1, 2H), 2.01 (d, J=12.2, 2H), 1.93 (dd, J=8.3, 5.0, 4H), 1.57 (s, 9H), 1.55-1.48 (m, 2H); $^{13}$C NMR (126 MHz, MeOD) δ 158.52 (C), 155.40 (CH), 154.15 (C), 153.45 (C), 149.24 (C), 145.00 (C), 128.80 (C), 127.36 (C), 120.43 (CH), 119.55 (CH), 110.27 (CH), 97.69 (C), 80.19 (C), 62.00 (CH), 56.16 (CH$_2$), 55.08 (CH$_3$), 51.62 (2×CH$_2$), 51.22 (2×CH$_2$), 44.01 (CH$_2$), 29.65 (2×CH$_2$), 27.22 (3×CH$_3$), 22.49 (2×CH$_2$); MS (ES +ve) [M+H]$^+$: 537.4, (ES −ve) [M−H]$^−$: 535.3; HRMS (ES +ve), C$_{28}$H$_{40}$N$_8$O$_3$ [M+H]$^+$: calculated 537.32961, found 537.3281.

tert-butyl N-[4-[4-amino-1-[2-[4-(1-piperidyl)-1-piperidyl]ethyl]pyrazolo[3,4-d]pyrimidin-3-yl]-2-methoxy-phenyl]carbamate (519)

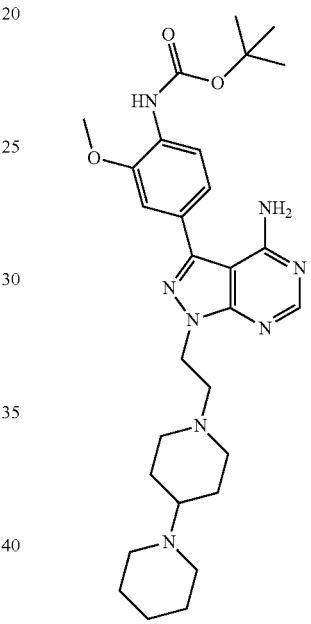

To a solution of 3-iodo-1-[2-[4-(1-piperidyl)-1-piperidyl]ethyl]pyrazolo[3,4-d]pyrimidin-4-amine (50 mg, 0.110 mmol) in dioxane/water (4.5 ml/0.5 ml) was added [4-(tert-butoxycarbonylamino)-3-methoxy-phenyl]boronic acid (1.5 eq., 44.0 mg, 0.165 mmol), potassium carbonate (1.5 eq., 22.8 mg, 0.165 mmol) and triphenylphosphine (20 mol %, 5.8 mg) followed by palladium acetate (5 mol %) and the mixture heated in the microwave at 120° C. for an hour. EtOAc (50 ml) and water (50 ml) were added to the mixture and the organic layer separated. The aqueous layer was washed with EtOAc (20 ml, ×2) and the organics combined, dried over MgSO$_4$ and concentrated in vacuo. The crude product was purified by column chromatography, MeOH/DCM (0-10% then 5-15 drops of NH$_3$ aq. per 100 ml) to give a light brown solid (12.3 mg, 22.35 μmol, 20.3%). $^1$H NMR (500 MHz, MeOD) δ 8.27 (s, 1H), 8.08 (d, J=8.2, 1H), 7.30 (d, J=1.7, 1H), 7.26 (dd, J=8.2, 1.8, 1H), 4.55 (t, J=6.6, 2H), 3.96 (s, 3H), 3.15 (d, J=11.8, 2H), 2.93 (t, J=6.6, 2H), 2.74 (br. s, 4H), 2.51 (br. s, 1H), 2.13 (t, J=11.1, 2H), 1.91 (d, J=12.0, 2H), 1.72-1.62 (m, 4H), 1.55 (m, 13H); $^{13}$C NMR (126 MHz, MeOD) δ 158.52 (C), 155.40 (CH), 154.13 (C), 153.45 (C), 149.24 (C), 145.02 (C), 128.79 (C), 127.37 (C), 120.43 (CH), 119.56 (CH), 110.28 (CH), 97.73 (C), 80.19

(C), 62.69 (CH), 56.21 (CH$_2$), 55.08 (CH$_3$), 52.43 (2×CH$_2$), 49.83 (2×CH$_2$), 44.00 (CH$_2$), 27.22 (3×CH$_3$), 26.78 (2×CH$_2$), 24.68 (2×CH$_2$), 23.34 (CH$_2$); MS (ES +ve) [M+H]$^+$: 551.2; HRMS (ES +ve), C$_{29}$H$_{42}$N$_8$O$_3$ [M+H]$^+$: calculated 551.34526, found 551.3469.

Phenyl N-[2-methoxy-4-(4,4,5,5-tetramethyl-1,3,2-dioxaborolan-2-yl)phenyl]carbamate

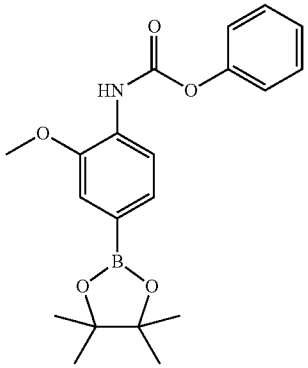 [SMILES: COc1cc(B2OC(C)(C)C(C)(C)O2)ccc1NC(=O)Oc1ccccc1]

To a solution of 4-Amino-3-methoxybenzeneboronic acid, pinacol ester (150 mg, 0.602 mmol) in DCM (2 ml) was added triethylamine (1.2 eq., 0.722 mmol, 73.1 mg, 100.76 µl) followed by phenyl chloroformate (1.2 eq., 0.722 mmol, 112.6 mg, 90.25 µl) and the mixture allowed to stir for 20 hours. Water was added to the mixture and the organic layer separated, dried over MgSO$_4$ and concentrated in vacuo. The product was purified by column chromatography, (100% DCM) to give a clear white solid (190.8 mg, 0.517 mmol, 85.9%). $^1$H NMR (500 MHz, CDCl3) δ 8.16 (d, J=7.6, 1H), 7.74 (s, 1H), 7.49 (dd, J=8.0, 1.1, 1H), 7.46-7.40 (m, 2H), 7.33 (d, J=1.0, 1H), 7.29-7.20 (m, 3H), 3.99 (s, 3H), 1.38 (s, 12H); $^{13}$C NMR (126 MHz, CDCl3) δ 151.36 (C), 150.61 (C), 146.98 (C), 129.97 (C), 129.41 (2×CH), 128.61 (CH), 125.68 (CH), 125.05 (C), 121.74 (2×CH), 117.30 (CH), 115.41 (CH), 83.80 (2×C), 55.96 (CH$_3$), 24.92 (4×CH$_3$); MS (ES +ve) [M+H]$^+$: 370.5, 392.5 (+Na).

N-[2-methoxy-4-(4,4,5,5-tetramethyl-1,3,2-dioxaborolan-2-yl)phenyl]-3,3-dimethyl-butanamide

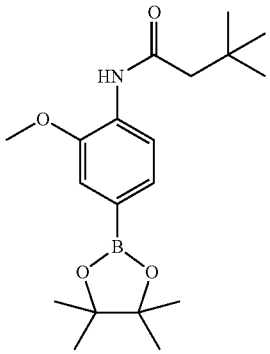 [SMILES: COc1cc(B2OC(C)(C)C(C)(C)O2)ccc1NC(=O)CC(C)(C)C]

To a solution of 4-Amino-3-methoxybenzeneboronic acid, pinacol ester (150 mg, 0.602 mmol) in DCM (2 ml) was added triethylamine (1.2 eq., 0.722 mmol, 73.1 mg, 100.76 µl) followed by t-butylacetal chloride (1.2 eq., 0.722 mmol, 96.8 mg, 99.9 µl) and the mixture allowed to stir for 20 hours. Water was added to the mixture and the organic layer separated, dried over MgSO$_4$ and concentrated in vacuo. The product was purified by column chromatography, MeOH/DCM (0-3%) to give a brown solid (195.7 mg, 0.564 mmol, 93.6%). $^1$H NMR (500 MHz, CDCl3) δ 8.44 (d, J=8.0, 1H), 7.83 (s, 1H), 7.47 (dd, J=8.0, 1.0, 1H), 7.32-7.29 (m, 1H), 3.95 (s, 3H), 2.31-2.27 (m, 2H), 1.36 (s, 12H), 1.13 (s, 9H); $^{13}$C NMR (126 MHz, CDCl3) δ 170.06 (C), 169.99 (C), 146.89 (C), 130.52 (C), 128.54 (CH), 118.61 (CH), 115.22 (CH), 83.75 (2×C), 55.86 (CH$_3$), 52.08 (CH$_2$), 31.22 (C), 29.81 (3×CH$_3$), 24.86 (4×CH$_3$); MS (ES +ve) [M+H]$^+$: 348.6, 370.6 (+Na).

N-[2-methoxy-4-(4,4,5,5-tetramethyl-1,3,2-dioxaborolan-2-yl)phenyl]-3-phenyl-propanamide

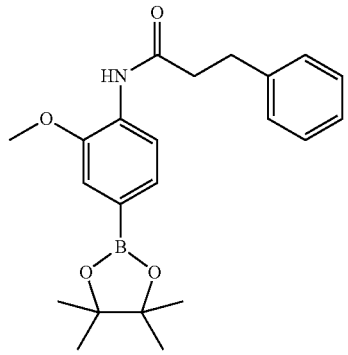 [SMILES: COc1cc(B2OC(C)(C)C(C)(C)O2)ccc1NC(=O)CCc1ccccc1]

To a solution of 4-Amino-3-methoxybenzeneboronic acid, pinacol ester (150 mg, 0.602 mmol) in DCM (2 ml) was added triethylamine (1.2 eq., 0.722 mmol, 73.1 mg, 100.76 µl) followed by hydrocinnamoyl chloride (1.2 eq., 0.722 mmol, 121.3 mg, 106.9 µl) and the mixture allowed to stir for 23 hours. The mixture was concentrated in vacuo and purified by column chromatography, MeOH/DCM (0-2%) to give a brown solid, (240.0 mg, 0.629 mmol, 100%). $^1$H NMR (500 MHz, CDCl3) δ 8.44 (d, J=8.0, 1H), 7.83 (s, 1H), 7.47 (d, J=8.0, 1H), 7.35-7.30 (m, 2H), 7.28-7.21 (m, 4H), 3.90 (s, 3H), 3.14-3.04 (m, 2H), 2.79-2.72 (m, 2H), 1.37 (s, 12H); $^{13}$C NMR (126 MHz, CDCl3) δ 170.25 (C), 170.17 (C), 146.82 (C), 140.70 (C), 130.40 (C), 128.56 (CH), 128.52 (CH), 128.40 (CH), 126.34 (CH), 118.68 (CH), 115.21 (CH), 83.78 (2×C), 55.84 (CH$_3$), 39.72 (CH$_2$), 31.42 (CH$_2$), 24.87 (4×CH$_3$); MS (ES +ve) [M+H]$^+$: 382.7, 390.6 (+Na)

N-[2-methoxy-4-(4,4,5-tetramethyl-1,3-dioxolan-2-yl)phenyl]-2-phenyl-acetamide

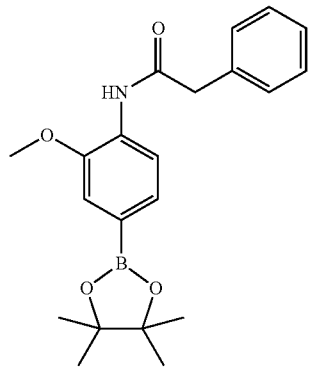 [SMILES: COc1cc(B2OC(C)(C)C(C)(C)O2)ccc1NC(=O)Cc1ccccc1]

To a solution of 4-Amino-3-methoxybenzeneboronic acid, pinacol ester (150 mg, 0.602 mmol) in DCM (2 ml) was added triethylamine (1.2 eq., 0.722 mmol, 73.1 mg, 100.76 µl) followed by phenylacetyl chloride (1.2 eq., 0.722 mmol, 111.2 mg, 95.1 µl) and the mixture allowed to stir for 18 hours. The mixture was concentrated in vacuo and purified by column chromatography, MeOH/DCM (0-1.5%) to give a cream solid, (200.9 mg, 0.547 mmol, 90.9%). $^1$H NMR (500 MHz, CDCl3) δ 8.40 (d, J=8.0, 1H), 7.95 (s, 1H), 7.43 (ddd, J=11.3, 6.6, 1.6, 3H), 7.39-7.33 (m, 3H), 7.22 (d, J=1.0, 1H), 3.78 (s, 5H), 1.35 (s, 12H); $^{13}$C NMR (126 MHz, CDCl3) δ 168.92 (C), 168.84 (C), 147.04 (C), 134.50 (C), 130.31 (C), 129.61 (2×CH), 129.05 (2×CH), 128.51 (CH), 127.47 (CH), 118.43 (CH), 115.31 (CH), 83.76 (C), 55.88 (CH$_3$), 45.24 (CH$_2$), 24.86 (4×CH$_3$); MS (ES +ve) [M+H]$^+$: 368.7, 390.6 (+Na)

N-benzyl-2-methoxy-4-(4,4,5,5-tetramethyl-1,3,2-dioxaborolan-2-yl)aniline

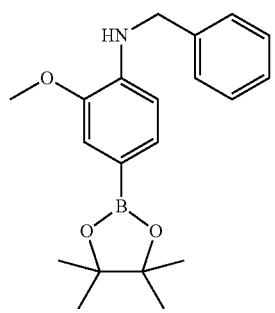 [SMILES: COc1cc(B2OC(C)(C)C(C)(C)O2)ccc1NCc1ccccc1]

To a solution of 4-Amino-3-methoxybenzeneboronic acid, pinacol ester (150 mg, 0.602 mmol) in DCM (2 ml) was added triethylamine (1.2 eq., 0.722 mmol, 73.1 mg, 100.76 µl) followed by benzyl chloroformate (1.2 eq., 0.722 mmol, 123.2 mg, 103.07 µl) and the mixture allowed to stir for 18 hours. The product was concentrated in vacuo and purified by column chromatography (100% DCM), to give a light brown thick oil, (65.9 mg, 0.172 mmol, 28.6%). Only after characterisation was it discovered that the alkylated product (shown) had been produced instead. $^1$H NMR (600 MHz, CDCl3) δ 7.43-7.26 (m, 8H), 6.68 (d, J=7.6, 1H), 4.41 (s, 2H), 3.91 (s, 3H), 1.35 (s, 12H); $^{13}$C NMR (126 MHz, MeOD) δ 158.39 (C), 146.09 (C), 141.18 (C), 139.78 (C), 128.82 (CH), 128.08 (CH), 126.76 (CH), 126.52 (CH), 114.34 (CH), 108.93 (CH), 83.13 (CH$_2$), 54.55 (CH$_3$), 46.58 (C), 23.73 (4×CH$_3$); MS (ES +ve) [M+H]$^+$: 340.6.

1-tert-butyl-3-[2-methoxy-4-(4,4,5,5-tetramethyl-1,3,2-dioxaborolan-2-yl)phenyl]urea

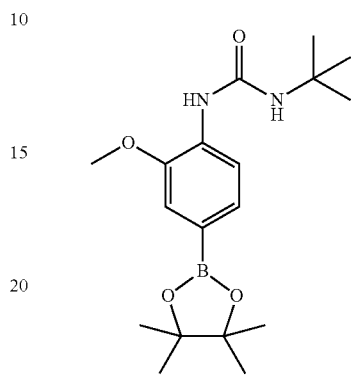

To a solution of 4-Amino-3-methoxybenzeneboronic acid, pinacol ester (150 mg, 0.602 mmol) in DCM (3 ml) was added t-butylisocyanate (20 eq., 12.04 mmol, 1.19 g) and the mixture left to stir at for 72 hours. DCM and water were added to the mixture and the organic layer separated, dried over MgSO$_4$ and concentrated in vacuo. The product was purified by column chromatography, MeOH/DCM (0-2%) to give a dark brown solid, (40.9 mg, 0.117 mmol, 19.5%). $^1$H NMR (500 MHz, CDCl3) δ 8.09 (d, J=8.0, 1H), 7.44 (dd, J=8.0, 1.2, 1H), 7.27 (d, J=1.0, 1H), 6.88 (s, 1H), 3.92 (s, 3H), 1.42 (s, 9H), 1.37 (d, J=3.9, 12H); $^{13}$C NMR (126 MHz, CDCl3) δ 153.97 (C), 146.81 (C), 131.78 (C), 128.70 (CH), 117.77 (CH), 115.36 (CH), 83.65 (CH), 55.74 (C), 50.97 (CH$_3$), 29.36 (C), 29.09 (3×CH), 24.87 (4×CH$_3$); MS (ES +ve) [M+H]$^+$: 349.7, 371.6 (+Na)

tert-butyl 2-[4-(4,4,5,5-tetramethyl-1,3,2-dioxaborolan-2-yl)phenyl]acetate

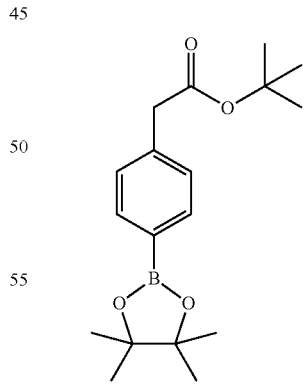

4-(Carboxymethyl)phenylboronic acid pinacol ester (150 mg, 0.572 mmol) was dissolved in 5 ml of dry toluene. Thionyl chloride (1.2 eq., 0.686 mmol, 81.6 mg, 49.8 ul) was added followed by a drop of DMF and the reaction heated to reflux (120° C.) for 2 hours. The reaction was cooled to r.t. then t-butylalcohol (5 eq., 2.86 mmol, 211.8 mg, 0.273 ml) and triethylamine (2.5 eq., 1.43 mmol, 199.3 ul) added and the mixture allowed to stir for 18 hours. Water and DCM were added to the mixture and the organic layer separated, dried over MgSO$_4$ and concentrated in vacuo. The crude product was purified by column chromatography, (100% DCM), to give a light brown oil, (60 mg, 0.189 mmol, 33.0%). MS (ES +ve) (M+H)$^+$: 340.8 (+Na)

[3-(tert-butoxycarbonylamino)-4-methoxy-phenyl] boronic acid

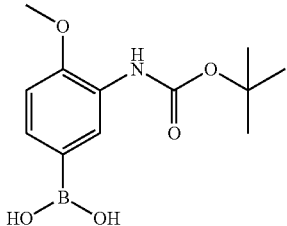 [SMILES: COc1ccc(B(O)O)cc1NC(=O)OC(C)(C)C]

(3-Amino-4-methoxyphenyl)boronic acid (150 mg, 0.898 mmol) was suspended in DCM (5 ml). Di-tertbutyldicarbonate (1.5 eq., 1.347 mmol, 294.0 mg) was added followed by a small spatula of DMAP and the reaction allowed to stir for 18 hours. Water was added to the mixture and the organic layer separated, dried over MgSO$_4$ and concentrated in vacuo. The product was purified by column chromatography, MeOH/DCM (0-4%) to give a dark brown solid (189.9 mg, 0.711 mmol, 79.2%). $^1$H NMR (500 MHz, MeOD) δ 8.12 (s, 1H), 7.34 (dd, J=8.2, 1.5, 1H), 6.98 (d, J=8.2, 1H), 3.88 (s, J=4.9, 3H), 1.53 (s, 9H); $^{13}$C NMR (126 MHz, MeOD) δ 153.77 (C), 150.52 (C), 129.82 (CH), 129.49 (CH), 126.76 (C), 125.18 (C), 109.48 (CH), 79.78 (C), 54.74 (CH$_3$), 27.26 (3×CH$_3$); MS (ES +ve) [M+H]$^+$: 268.5.

tert-butyl 2-[2-methoxy-4-(4,4,5,6-tetramethyl-1,3, 2-dioxaborolan-2-yl)phenyl]acetate

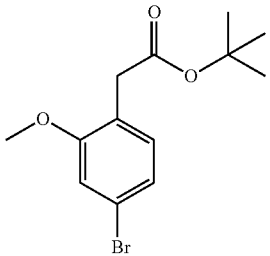 [SMILES: COc1cc(Br)ccc1CC(=O)OC(C)(C)C]

2-(4-Bromo-2-methoxyphenyl)acetic acid (2 g, 8.198 mmol) was dissolved in 20 ml of dry THF. Thionyl chloride (1.2 eq., 9.837 mmol, 1.17 g, 0.714 ml) was added followed by a drop of DMF and the reaction heated to reflux (80° C.) for 2 hours. The reaction was cooled to r.t. then t-butylalcohol (5 eq., 40.99 mmol, 3.04 g, 3.92 ml) and triethylamine (2.5 eq., 20.49 mmol, 2.86 ml) added and the mixture left to stir for 20 hours. Water and EtOAc were added to the mixture and the organic layer separated, dried over MgSO$_4$ and concentrated in vacuo. The product was purified by column chromatography, EtOAC/Hexane (0-4%) to give a light orange liquid, (694.8 mg, 2.316 mmol, 28.2%). $^1$H NMR (500 MHz, MeOD) δ 7.10 (s, 1H), 7.07-7.02 (m, 2H), 3.81 s, 3H), 3.47 (s, 2H), 1.42 (s, 9H); $^{13}$C NMR (126 MHz, MeOD) δ 171.39 (C), 158.43 (C), 131.77 (CH), 122.99 (C), 122.98 (CH), 121.02 (C), 113.67 (CH), 80.51 (C), 54.84 (CH$_3$), 36.42 (CH$_2$), 26.85 (3×CH$_3$); MS (ES +ve) (M+H)$^+$: 323.2/324.8 (+Na).

tert-butyl 2-[2-methoxy-4-(4,4,5,5-tetramethyl-1,3, 2-dioxaborolan-2-yl)phenyl]acetate

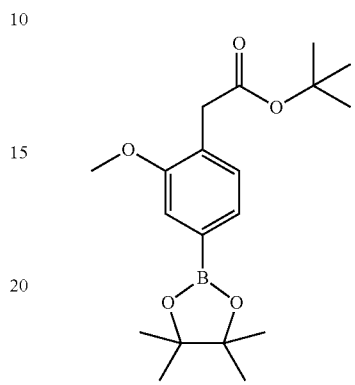

To a solution of tert-butyl 2-[2-methoxy-4-(4,4,5,5-tetramethyl-1,3,2-dioxaborolan-2-yl)phenyl]acetate (600 mg, 2.0 mmol) in dioxane/water (18/2 ml) was added bis(pinacolato)diboron (1.5 eq., 762.6 mg, 3.0 mmol), potassium carbonate (1.5 eq., 414.6 mg, 3.0 mmol) and triphenylphosphine (20 mol %, 104.9 mg) followed by palladium acetate (5 mol %, 22.5 mg) and the mixture heated in the microwave at 120° C. for an hour. MS showed a little SM so the mixture was heated for another hour. MS and TLC showed the reaction was complete. EtOAc and water were added to the mixture and the organic layer separated, dried over MgSO$_4$ and concentrated in vacuo. The product was purified by column chromatography, EtOAc/Hexane (0-10%) to give a colourless oil, (322.4 mg, 0.926 mmol, 46.3%). $^1$H NMR (500 MHz, CDCl3) δ 7.37 (d, J=8.0, 1H), 7.26 (d, J=3.0, 1H), 7.18 (d, J=7.3, 1H), 3.86 (s, 3H), 3.54 (s, 2H), 1.42 (s, 9H), 1.34 (s, 12H); $^{13}$C NMR (126 MHz, CDCl3) δ 170.96 (C), 157.02 (C), 130.25 (CH), 127.29 (C), 127.28 (CH), 115.89 (CH), 109.97 (C), 83.75 (C), 80.34 (C), 55.46 (CH$_3$), 37.58 (CH$_2$), 28.03 (3×CH$_3$), 24.85 (4×CH$_3$); MS (ES +ve) [M+H]$^+$: 349.7.

2-(4-bromo-2-methoxy-phenyl)-N-prop-2-ynyl-acetamide

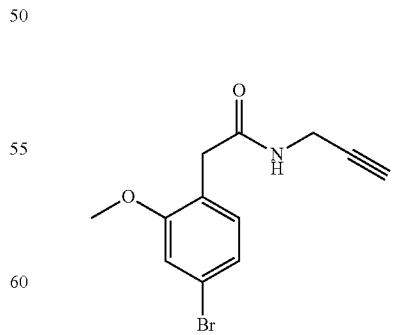

2-(4-Bromo-2-methoxyphenyl)acetic acid (500 mg, 2.049 mmol) was dissolved in 5 ml of dry toluene. Thionyl chloride (1.2 eq., 2.46 mmol, 292.7 mg, 178.3 ul) was added followed by a drop of DMF and the reaction heated to reflux (120° C.) for 3 hours. The reaction was cooled to r.t. then propargylamine (2.5 eq., 5.12 mmol, 282.2 mg, 0.328 ml) and triethylamine (2.5 eq., 5.12 mmol, 0.714 ml) added and the reaction left to stir for 20 hours. DCM and water were added to the mixture and the organic layer separated, dried over MgSO$_4$ and concentrated in vacuo. The product was purified by column chromatography, MeOH/DCM (0-3%) to give a cream coloured solid, (458.2 mg, 1.631 mmol, 79.6%). $^1$H NMR (500 MHz, CDCl3) δ 7.13-7.07 (m, 2H), 7.04 (s, 1H), 5.78 (s, 1H), 3.99 (dd, J=5.2, 2.6, 2H), 3.86 (s, 3H), 3.51 (s, 2H), 2.21-2.16 (m, 1H); $^{13}$C NMR (126 MHz, CDCl3) δ 170.11 (C), 157.79 (C), 132.32 (CH), 124.16 (CH), 122.35 (C), 122.07 (C), 114.50 (CH), 79.53 (C), 71.45 (CH), 55.85 (CH$_3$), 38.02 (CH$_2$), 29.23 (CH$_2$); MS (ES +ve) (M+H)$^+$: 281.6/283.6, 303.8/306.0 (+Na)

2-[(4-bromo-2-methoxy-phenyl)methyl]-5-methyl-oxazole

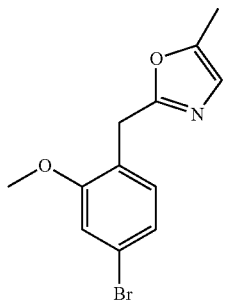 [SMILES: COc1cc(Br)ccc1Cc1ncc(C)o1]

2-(4-bromo-2-methoxy-phenyl)-N-prop-2-ynyl-acetamide (200 mg, 0.713 mmol) was dissolved in 2 ml of 1,2-dichloroethane in a microwave vial. FeCl$_3$ (0.5 eq., 57.6 mg, 0.356 mmol) was added and the mixture heated to 150° C. for 90 mins. Water and DCM were added to the mixture and the organic layer separated, dried over MgSO$_4$ and concentrated in vacuo. The product was purified by column chromatography, MeOH/DCM (1%), to give a light yellow/orange oil, (108.7 mg, 0.389 mmol, 54.3%). $^1$H NMR (500 MHz, CDCl3) δ 7.09-7.03 (m, 2H), 7.01 (s, 1H), 6.65 (d, J=1.1, 1H), 4.04 (s, 2H), 3.82 (s, 3H), 2.26 (d, J=1.2, 3H); $^{13}$C NMR (126 MHz, CDCl3) δ 161.66 (C), 157.87 (C), 148.90 (C), 131.42 (CH), 123.66 (CH), 123.09 (C), 122.03 (CH), 121.65 (C), 114.31 (CH), 55.83 (CH$_3$), 28.30 (CH$_2$), 10.88 (CH$_3$); MS (ES +ve) (M+H)$^+$: 281.6/283.6, 303.8/306.0 (+Na).

2-[[2-methoxy-4-(4,4,5,5-tetramethyl-1,3,2-dioxaborolan-2-yl)phenyl]methyl]-5-methyl-oxazole

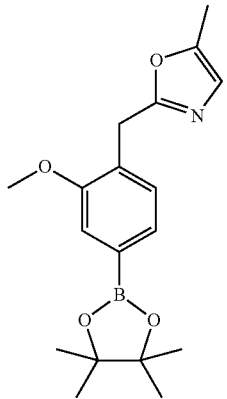 [SMILES: COc1cc(B2OC(C)(C)C(C)(C)O2)ccc1Cc1ncc(C)o1]

To a solution of 2-[(4-bromo-2-methoxy-phenyl)methyl]-5-methyl-oxazole (80 mg, 0.285 mmol) in dioxane/water (4.5/0.5 ml) was added bis(pinacolato)diboron (1.5 eq., 108.5 mg, 0.427 mmol), potassium carbonate (1.5 eq., 59.0 mg, 0.427 mmol) and triphenylphosphine (20 mol %, 15.0 mg) followed by palladium acetate (5 mol %) and the mixture heated in the microwave at 120° C. for 30 mins. The mixture was concentrated in vacuo and purified by column chromatography, EtOAc/hexane (30-40%) to give a clear oil, (37.0 mg, 0.1124 mmol, 39.4%). $^1$H NMR (500 MHz, MeOD) δ 7.35-7.30 (m, 1H), 7.20-7.12 (m, 1H), 6.69-6.65 (m, 1H), 5.97 (s, 1H), 4.51 (s, 2H), 4.08 (s, 3H), 2.28 (s, 3H), 1.37 (s, 12H); MS (ES +ve) (M+H)$^+$: 329.18

N-[4-[4-amino-1-[2-[4-(dimethylamino)-1-piperidyl]ethyl]pyrazolo[3,4-d]pyrimidin-3-yl]-2-methoxy-phenyl]-3,3-demethyl-butanamide (526)

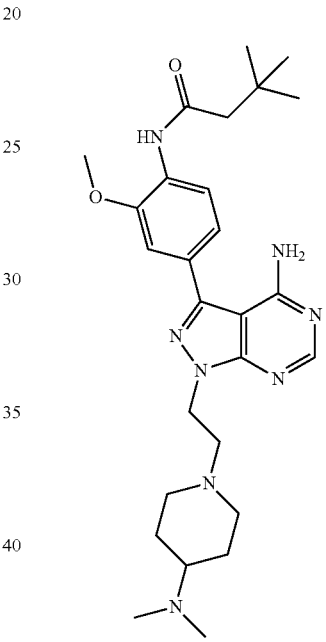

To a solution of 1-[2-[4-(dimethylamino)-1-piperidyl]ethyl]-3-iodo-pyrazolo[3,4-d]pyrimidin-4-amine (50 mg, 0.1205 mmol) in dioxane/water (4.5 ml/0.5 ml) was added N-[2-methoxy-4-(4,4,5,5-tetramethyl-1,3,2-dioxaborolan-2-yl)phenyl]-3,3-dimethyl-butanamide (1.5 eq., 63.1 mg, 0.181 mmol), potassium carbonate (1.5 eq., 25.0 mg, 0.181 mmol) and triphenylphosphine (20 mol %, 9.5 mg) followed by palladium acetate (5 mol %) and the mixture heated in the microwave at 120° C. for 30 mins. The product was concentrated in vacuo and purified by column chromatography, MeOH/DCM (5-10% then 0-30 drops of triethylamine per 100 ml) to give a sand coloured solid, (34.3 mg, 0.0675 mmol, 56.0%). $^1$H NMR (500 MHz, MeOD) δ 8.28 (s, 1H), 8.10 (d, J=8.1, 1H), 7.35 (d, J=1.8, 1H), 7.28 (dd, J=8.1, 1.8, 1H), 4.57 (t, J=6.7, 2H), 3.99 (s, 3H), 3.15 (m, 2H), 2.95 (t, J=6.7, 2H), 2.39 (m, 9H), 2.15 (t, J=11.0, 2H), 1.91 (d, J=16.8, 2H), 1.49 (m, 2H), 1.14 (s, 9H); $^{13}$C NMR (128 MHz, MeOD) δ 172.20 (C), 158.53 (C), 155.44 (CH), 154.22 (C), 151.00 (C), 144.89 (C), 129.52 (C), 127.69 (C), 123.12 (CH), 120.22 (CH), 110.74 (CH), 97.79 (C), 62.24 (CH), 56.24 (CH$_2$), 55.08 (CH$_3$), 52.23 (2×CH$_2$), 49.79 (CH$_2$), 44.04 (CH$_2$), 40.11 (2×CH), 30.67 (C), 28.81

(3×CH$_3$), 27.31 (2×CH$_2$); MS (ES +ve) [M+H]$^+$: 509.6; HRMS (ES +ve), C$_{27}$H$_{41}$N$_8$O$_2$ [M+H]$^+$: calculated 509.33470, found 509.3363.

3-(4-amino-3-methoxy-phenyl)-1-[2-[4-(dimethyl-amino)-1-piperidyl]ethyl]pyrazolo[3,4-d]pyrimidin-4-amine (532)

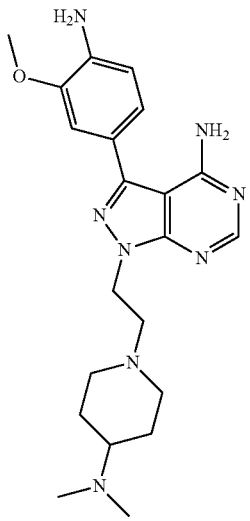 [SMILES: COc1cc(-c2nn(CCN3CCC(N(C)C)CC3)c3ncnc(N)c23)ccc1N]

To a solution of 1-[2-[4-(dimethylamino)-1-piperidyl]ethyl]-3-iodo-pyrazolo[3,4-d]pyrimidin-4-amine (50 mg, 0.1205 mmol) in dioxane/water (4.5 ml/0.5 ml) was added phenyl N-[2-methoxy-4-(4,4,5,5-tetramethyl-1,3,2-dioxaborolan-2-yl)phenyl]carbamate (1.5 eq., 66.8 mg, 0.181 mmol), potassium carbonate (1.5 eq., 25.0 mg, 0.181 mmol) and triphenylphosphine (20 mol %, 9.5 mg) followed by palladium acetate (5 mol %) and the mixture heated in the microwave at 120° C. for 30 mins. The mixture was concentrated in vacuo and the product purified by column chromatography, MeOH/DCM (10% then 0-30 drops of NEt$_3$ per 100 ml) to give a brown solid, (19.4 mg, 0.0473 mmol, 39.2%). $^1$H NMR (600 MHz, MeOD) δ 8.25 (s, 1H), 7.16 (d, J=1.8, 1H), 7.09 (dd, J=7.9, 1.8, 1H), 6.91 (d, J=7.9, 1H), 4.54 (t, J=6.7, 2H), 3.95 (s, 3H), 3.14 (d, J=12.0, 2H), 2.93 (t, J=6.7, 2H), 2.40 (m, 7H), 2.14 (t, J=11.0, 2H), 1.90 (d, J=12.3, 2H), 1.49 (d, J=12.1, 2H); $^{13}$C NMR (126 MHz, MeOD) δ 158.62 (C), 155.35 (CH), 153.98 (C), 147.74 (C), 146.01 (C), 138.32 (C), 121.70 (CH), 121.07 (C), 114.69 (CH), 110.25 (CH), 109.97 (C), 62.19 (CH$_2$), 56.24 (CH$_3$), 54.74 (2×CH$_2$), 52.29 (CH), 43.91 (CH$_2$), 40.14 (2×CH$_3$), 27.35 (2×CH$_2$); MS (ES +ve) (M+H)$^+$: 411.6; HRMS (ES +ve), C$_{21}$H$_{31}$N$_8$O$_1$ (M+H)$^+$: calculated 411.26208, found 411.26270.

N-[4-[4-amino-1-[2-[4-(dimethylamino)-1-piperidyl]ethyl]pyrazolo[3,4-d]pyrimidin-3-yl]-2-methoxy-phenyl]-2-phenyl-acetamide (630)

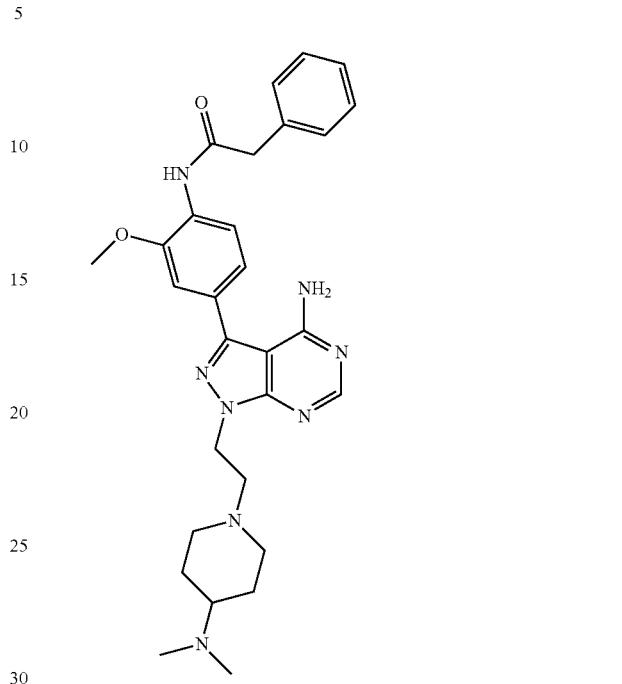

To a solution of 1-[2-[4-(dimethylamino)-1-piperidyl]ethyl]-3-iodo-pyrazolo[3,4-d]pyrimidin-4-amine (50 mg, 0.1205 mmol) in dioxane/water (4.5 ml/0.5 ml) was added N-[2-methoxy-4-(4,4,5,5-tetramethyl-1,3-dioxolan-2-yl)phenyl]-2-phenyl-acetamide (1.5 eq., 66.5 mg, 0.181 mmol), potassium carbonate (1.5 eq., 25.0 mg, 0.181 mmol) and triphenylphosphine (20 mol %, 9.5 mg) followed by palladium acetate (5 mol %) and the mixture heated in the microwave at 120° C. for 30 mins. The product was concentrated in vacuo and purified by column chromatography, MeOH/DCM (10% then 0-30 drops of triethylamine per 100 ml) to give a light brown solid, (37.9 mg, 0.0717 mmol, 59.5%). $^1$H NMR (600 MHz, MeOD) δ 8.27 (s, 1H), 8.20 (d, J=8.2, 1H), 7.40 (dt, J=15.2, 7.5, 4H), 7.32 (dd, J=11.0, 4.4, 2H), 7.26 (dd, J=8.2, 1.8, 1H), 4.56 (t, J=6.7, 2H), 3.95 (s, 3H), 3.83 (s, 2H), 3.13 (d, J=11.8, 2H), 2.93 (t, J=6.7, 2H), 2.34 (d, J=13.6, 7H), 2.13 (t, J=11.0, 2H), 1.88 (d, J=12.7, 2H), 1.47 (dt, J=12.2, 8.6, 2H); $^{13}$C NMR (126 MHz, MeOD) δ 171.20 (C), 158.51 (C), 155.42 (CH), 154.17 (C), 150.35 (C), 144.81 (C), 135.19 (C), 129.30 (C), 128.98 (2×CH), 128.38 (2×CH), 127.83 (C), 126.78 (CH), 122.00 (CH), 120.30 (CH), 110.62 (CH), 97.77 (C), 62.25 (CH), 56.21 (CH$_2$), 55.12 (CH$_3$), 52.24 (2×CH$_2$), 44.05 (CH$_2$), 43.30 (CH$_2$), 40.09 (2×CH$_3$), 27.29 (2×CH$_2$); MS (ES +ve) [M+H]$^+$: 529.6; HRMS (ES +ve), C$_{29}$H$_{37}$N$_8$O$_2$ [M+H]$^+$: calculated 529.30340, found 529.3051.

71

N-[4-[4-amino-1-[2-[4-(dimethylamino)-1-piperidyl]ethyl]pyrazolo[3,4-d]pyrimidin-3-yl]-2-methoxy-phenyl]-3-phenyl-propanamide (531)

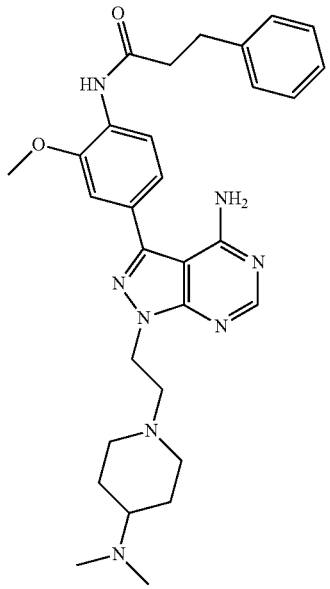 [SMILES: COc1cc(-c2nn(CCN3CCC(N(C)C)CC3)c3ncnc(N)c23)ccc1NC(=O)CCc1ccccc1]

To a solution of 1-[2-[4-(dimethylamino)-1-piperidyl]ethyl]-3-iodo-pyrazolo[3,4-d]pyrimidin-4-amine (50 mg, 0.1205 mmol) in dioxane/water (4.5 ml/0.5 ml) was added N-[2-methoxy-4-(4,4,5,5-tetramethyl-1,3,2-dioxaborolan-2-yl)phenyl]-3-phenyl-propanamide (1.5 eq., 69.0 mg, 0.181 mmol), potassium carbonate (1.5 eq., 25.0 mg, 0.181 mmol) and triphenylphosphine (20 mol %, 9.5 mg) followed by palladium acetate (5 mol %) and the mixture heated in the microwave at 120° C. for 30 mins. The product was concentrated in vacuo and purified by column chromatography, MeOH/DCM (10% then 0-30 drops of triethylamine per 100 ml) to give a light brown solid, (36.0 mg, 0.0664 mmol, 55.1%). $^1$H NMR (600 MHz, MeOD) δ 8.27 (s, 1H), 8.13 (d, J=8.1, 1H), 7.27 (d, J=1.7, 5H), 7.26 (dd, J=8.2, 1.8, 1H), 7.21 (dd, J=8.6, 4.4, 1H), 4.57 (t, J=6.7, 2H), 3.95 (s, 3H), 3.15 (d, J=11.8, 2H), 3.05 (m, 3H), 2.95 (t, J=6.7, 2H), 2.81 (t, J=7.7, 2H), 2.41 (s, 6H), 2.14 (t, J=11.0, 2H), 1.91 (d, J=17.2, 3H), 1.49 (d, J=8.7, 2H); $^{13}$C NMR (126 MHz, MeOD) δ 172.65 (C), 158.53 (CH), 155.44 (C), 154.18 (C), 150.64 (C), 144.88 (C), 140.73 (C), 129.32 (C), 128.15 (CH), 127.76 (C), 125.85 (CH), 122.70 (CH), 120.20 (CH), 110.65 (CH), 97.77 (CH), 62.38 (C), 56.18 (CH$_2$), 55.06 (CH$_3$), 52.14 (2×CH$_2$), 46.33 (CH$_2$), 44.04 (CH$_2$), 39.99 (2×CH$_3$), 38.18 (CH$_2$), 31.38 (CH$_2$), 27.17 (2×CH$_2$); MS (ES +ve) [M+H]$^+$: 543.6; HRMS (ES +ve), C$_{30}$H$_{39}$N$_8$O$_2$ [M+H]$^+$: calculated 543.31905, found 543.3204.

72

3-[4-(benzylamino)-3-methoxy-phenyl]-1-[2-[4-(dimethylamino)-1-piperidyl]ethyl]pyrazolo[3,4-d]pyrimidin-4-amine (533)

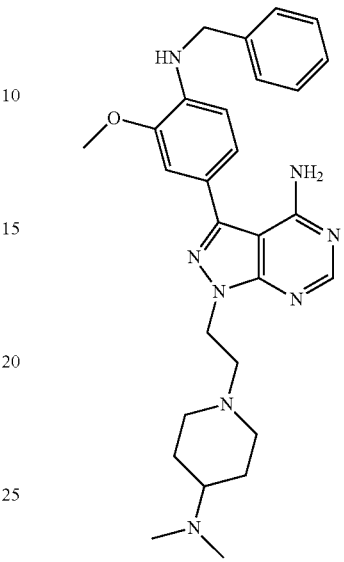

To a solution of 1-[2-[4-(dimethylamino)-1-piperidyl]ethyl]-3-iodo-pyrazolo[3,4-d]pyrimidin-4-amine (50 mg, 0.1205 mmol) in dioxane/water (4.5 ml/0.5 ml) was added N-benzyl-2-methoxy-4-(4,4,5,5-tetramethyl-1,3,2-dioxaborolan-2-yl)aniline (1.5 eq., 61.4 mg, 0.181 mmol), potassium carbonate (1.5 eq., 25.0 mg, 0.181 mmol) and triphenylphosphine (20 mol %, 9.5 mg) followed by palladium acetate (5 mol %) and the mixture heated in the microwave at 120° C. for 30 mins. The mixture was concentrated in vacuo without and purified by column chromatography, MeOH/DCM (10% then 5-20 drops of NEt$_3$ per 100 ml) to give a light brown coloured solid, (31.8 mg, 0.0584, 48.5%). $^1$H NMR (400 MHz, MeOD) δ 8.24 (a, 1H), 7.40 (d, J=7.5, 2H), 7.33 (t, J=7.5, 2H), 7.24 (t, J=7.3, 1H), 7.15 (d, J=1.8, 1H), 7.08 (dd, J=8.1, 1.8, 1H), 6.67 (d, J=8.1, 1H), 4.52 (t, J=6.7, 2H), 4.47 (s, 2H), 3.98 (s, 3H), 3.13 (d, J=11.9, 2H), 2.92 (t, J=6.7, 2H), 2.37 (s, 7H), 2.13 (t, J=11.0, 2H), 1.88 (d, J=12.3, 2H), 1.47 (d, J=8.5, 2H); $^{13}$C NMR (126 MHz, MeOD) δ 166.23 (C), 158.62 (C), 155.34 (CH), 153.97 (C), 147.34 (C), 139.75 (C), 139.27 (C), 128.13 (2×CH), 126.78 (2×CH), 126.58 (CH), 121.15 (CH), 119.94 (C), 109.78 (CH), 109.27 (CH), 97.66 (C), 62.17 (CH), 56.20 (CH$_2$), 54.81 (CH$_3$), 52.22 (2×CH$_2$), 46.71 (CH$_2$), 43.89 (CH$_2$), 40.08 (2×CH$_3$), 27.28 (2×CH$_2$); MS (ES +ve) [M+H]$^+$: 501.4; HRMS (ES +ve), C$_{28}$H$_{37}$N$_8$O$_1$ [M+H]$^+$: calculated 501.30848, found 501.3087.

73

1-[4-[4-amino-1-[2-[4-(dimethylamino)-1-piperidyl]ethyl]pyrazolo[3,4-d]pyrimidin-3-yl]-2-methoxyphenyl]-3-tert-butyl-urea (540)

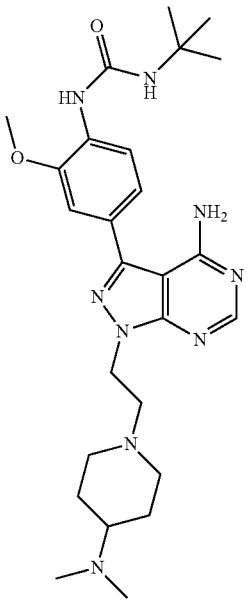

To a solution of 1-[2-[4-(dimethylamino)-1-piperidyl]ethyl]-3-iodo-pyrazolo[3,4-d]pyrimidin-4-amine (50 mg, 0.1205 mmol) in dioxane/water (4.5/0.5 ml) was added 1-tert-butyl-3-[2-methoxy-4-(4,4,5,5-tetramethyl-1,3,2-dioxaborolan-2-yl)phenyl]urea (1.5 eq., 62.9 mg, 0.181 mmol), potassium carbonate (1.5 eq., 25.0 mg, 0.181 mmol) and triphenylphosphine (20 mol %, 9.5 mg) followed by palladium acetate (5 mol %) and the mixture heated in the microwave at 120° C. for 30 mins. The mixture was concentrated in vacuo and purified by column chromatography, MeOH/DCM (10% then 0-30 drops of NEt$_3$ per 100 ml) to give a light brown solid, (30.4 mg, 0.0597 mmol, 49.5%). $^1$H NMR (500 MHz, MeOD) δ 8.24 (s, 1H), 8.16 (d, J=8.3, 1H), 7.25 (d, J=1.8, 1H), 7.19 (dd, J=8.3, 1.9, 1H), 4.53 (t, J=6.7, 2H), 3.96 (s, 3H), 3.12 (d, J=11.9, 2H), 2.92 (t, J=6.7, 2H), 2.36 (m, 7H), 2.12 (t, J=11.1, 2H), 1.87 (d, J=12.5, 2H), 1.51-1.42 (m, 2H), 1.38 (s, 9H); $^{13}$C NMR (126 MHz, MeOD) δ 155.74 (C), 155.40 (CH), 154.09 (C), 148.52 (C), 145.33 (C), 130.34 (C), 125.66 (C), 120.49 (CH), 118.66 (CH), 110.02 (CH), 97.73 (C), 62.27 (CH), 56.23 (CH$_2$), 55.02 (CH$_3$), 52.22 (2×CH$_2$), 49.71 (C), 43.97 (CH$_2$), 40.07 (2×CH$_3$), 28.15 (3×CH$_3$), 27.20 (2×CH$_2$); MS (ES +ve) [M+H]$^+$: 510.8; HRMS (ES +ve), C$_{26}$H$_{40}$N$_9$O$_2$ (M+H)$^+$: calculated 510.32995, found 510.32830.

74 tert-butyl N-[3-[4-amino-1-[2-[4-(dimethylamino)-1-piperidyl]ethyl]pyrazolo[3,4-d]pyrimidin-3-yl]phenyl]carbamate (542)

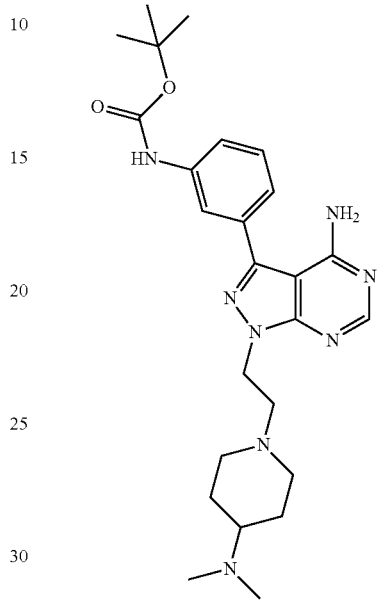

To a solution of 1-[2-[4-(dimethylamino)-1-piperidyl]ethyl]-3-iodo-pyrazolo[3,4-d]pyrimidin-4-amine (50 mg, 0.1205 mmol) in dioxane/water (4.5/0.5 ml) was added 3-(boc-amino)benzeneboronic acid (1.5 eq., 42.9 mg, 0.181 mmol), potassium carbonate (1.5 eq., 25.0 mg, 0.181 mmol) and triphenylphosphine (20 mol %, 9.5 mg) followed by palladium acetate (5 mol %) and the mixture heated in the microwave at 120° C. for 30 mins. The mixture was concentrated in vacuo and purified by column chromatography, MeOH/DCM (10% then 0-30 drops NEt$_3$ per 100 ml) to give a cream solid, (28.0 mg, 0.0583 mmol, 48.4%). $^1$H NMR (500 MHz, MeOD) δ 8.27 (s, 1H), 7.88 (s, 1H), 7.50-7.44 (m, 2H), 7.37 (d, J=7.0, 1H), 4.57 (t, J=6.7, 2H), 3.16-3.10 (m, 2H), 2.95 (t, J=6.7, 2H), 2.35 (m, 7H), 2.14 (t, J=11.0, 2H), 1.88 (d, J=12.7, 2H), 1.56 (s, 9H), 1.47 (m, 2H); $^{13}$C NMR (126 MHz, MeOD) δ 158.42 (C), 155.37 (CH), 154.22 (C), 154.00 (C), 144.97 (C), 140.14 (C), 133.30 (C), 129.46 (CH), 122.27 (CH), 119.16 (CH), 118.54 (CH), 97.74 (C), 79.72 (C), 62.16 (CH), 56.21 (CH$_2$), 52.29 (2×CH$_2$), 44.06 (CH$_2$), 40.16 (2×CH$_3$), 27.38 (2×CH$_2$), 27.28 (3×CH$_3$); MS (ES +ve) [M+H]$^+$: 481.4; HRMS (ES +ve), C$_{25}$H$_{37}$N$_8$O$_2$ [M+H]$^+$: calculated 480.30340, found 481.3054.

75
tert-butyl N-[5-[4-amino-1-[2-[4-(dimethylamino)-1-piperidyl]ethyl]pyrazolo[3,4-d]pyrimidin-3-yl]-2-pyridyl]carbamate (549)

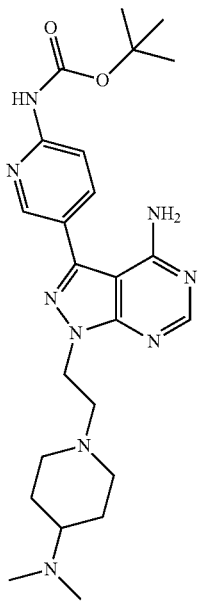 [SMILES: CN(C)C1CCN(CCn2nc(-c3ccc(NC(=O)OC(C)(C)C)nc3)c3c(N)ncnc32)CC1]

To a solution of 1-[2-[4-(dimethylamino)-1-piperidyl]ethyl]-3-iodo-pyrazolo[3,4-d]pyrimidin-4-amine (50 mg, 0.1205 mmol) in dioxane/water (4.5/0.5 ml) was added (6-((tert-Butoxycarbonyl)amino)pyridin-3-yl)boronic acid (1.5 eq., 43.1 mg, 0.181 mmol), potassium carbonate (1.5 eq., 25.0 mg, 0.181 mmol) and triphenylphosphine (20 mol %, 9.5 mg) followed by palladium acetate (5 mol %) and the mixture heated in the microwave at 120° C. for 30 mins. The mixture was concentrated in vacuo and purified by column chromatography, MeOH/DCM (10% then 10-30 drops of NEt$_3$ per 100 ml) to give a white solid, (23.8 mg, 0.0495 mmol, 41.0%). $^1$H NMR (500 MHz, MeOD) δ 8.55-8.51 (m, 1H), 8.26 (s, 1H), 8.06-8.01 (m, 2H), 4.55 (t, J=6.5, 2H), 3.14 (d, J=12.0, 2H), 2.94 (t, J=6.5, 2H), 2.68 (m, 1H), 2.55 (s, 6H), 2.14 (t, J=11.0, 2H), 1.92 (d, J=12.7, 2H), 1.55 (s, 9H), 1.53-1.46 (m, 2H); $^{13}$C NMR (126 MHz, MeOD) δ 158.58 (C), 155.47 (CH), 154.40 (C), 153.05 (C), 152.96 (C), 147.13 (CH), 141.83 (C), 137.78 (CH), 123.46 (C), 112.28 (CH), 97.92 (C), 80.49 (C), 62.79 (CH), 56.00 (CH$_2$), 51.78 (2×CH), 44.12 (CH$_2$), 39.64 (2×CH$_3$), 27.16 (3×CH$_3$), 26.76 (2×CH$_2$); MS (ES +ve) [M+H]$^+$: 481.8; HRMS (ES +ve), C$_{24}$H$_{36}$N$_9$O$_2$ [M+H]$^+$: calculated 482.29865, found 482.3004.

76
tert-butyl 2-[4-[4-amino-1-[2-[4-(dimethylamino)-1-piperidyl]ethyl]pyrazolo[3,4-d]pyrimidin-3-yl]phenyl]acetate (553)

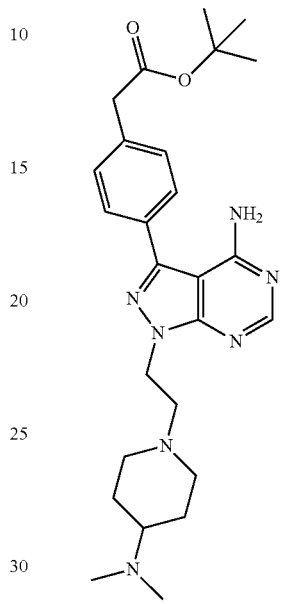

To a solution of 1-[2-[4-(dimethylamino)-1-piperidyl]ethyl]-3-iodo-pyrazolo[3,4-d]pyrimidin-4-amine (50 mg, 0.1205 mmol) in dioxane/water (4.5/0.5 ml) was added tert-butyl 2-[4-(4,4,5,5-tetramethyl-1,3,2-dioxaborolan-2-yl)phenyl]acetate (1.5 eq., 57.6 mg, 0.181 mmol), potassium carbonate (1.5 eq., 25.0 mg, 0.181 mmol) and triphenylphosphine (20 mol %, 9.5 mg) followed by palladium acetate (5 mol %) and the mixture heated in the microwave at 120° C. for 30 mins. The mixture was concentrated in vacuo and purified by column chromatography, MeOH/DCM (10% then 0-30 drops of NEt$_3$ per 100 ml) to give a light brown thick oil, (40.5 mg, 0.0845 mmol, 70.1%). $^1$H NMR (500 MHz, MeOD) δ 8.26 (s, 1H), 7.68-7.63 (m, 2H), 7.47 (d, J=8.2, 2H), 4.55 (t, J=6.6, 2H), 3.68 (s, 2H), 3.12 (d, J=11.9, 2H), 2.93 (t, J=6.6, 2H), 2.43 (m, 7H), 2.13 (t, J=11.0, 2H), 1.87 (m, 2H), 1.47 (m, 11H); $^{13}$C NMR (126 MHz, MeOD) δ 171.52 (C), 158.52 (C), 155.44 (CH), 154.21 (C), 144.85 (C), 136.00 (C), 131.41 (C), 129.95 (2×CH), 128.45 (2×CH), 97.81 (C), 81.01 (C), 62.40 (CH), 56.15 (CH$_2$), 52.10 (2×CH$_2$), 44.04 (CH$_2$), 41.58 (CH$_2$), 39.95 (2×CH$_3$), 27.13 (2×CH$_2$), 26.88 (3×CH$_3$); MS (ES +ve) [M+H]$^+$: 480.0; HRMS (ES +ve), C$_{26}$H$_{38}$N$_7$O$_2$ [M+H]$^+$: calculated 480.30815, found 480.3121.

2-[4-[4-amino-1-[2-[4-(dimethylamino)-1-piperidyl]ethyl]pyrazolo[3,4-d]pyrimidin-3-yl]phenyl]acetic acid (556)

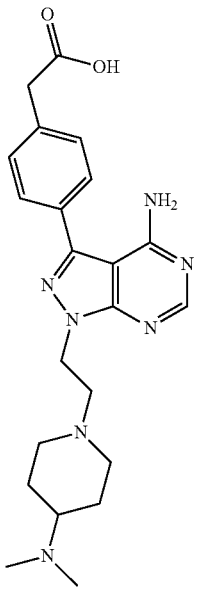 [SMILES: CN(C)C1CCN(CCn2nc(-c3ccc(CC(=O)O)cc3)c3c(N)ncnc32)CC1]

tert-butyl N-[5-[4-amino-1-[2-[4-(dimethylamino)-1-piperidyl]ethyl]pyrazolo[3,4-d]pyrimidin-3-yl]-2-methoxy-phenyl]carbamate (559)

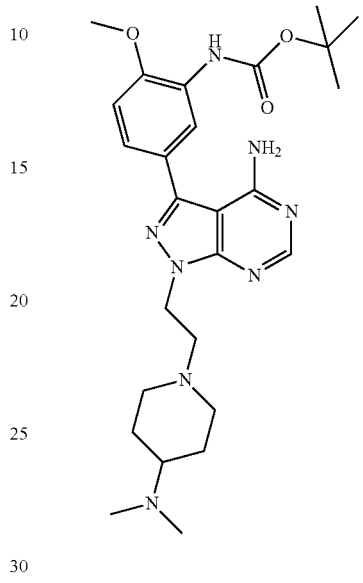

To a solution of 1-[2-[4-(dimethylamino)-1-piperidyl]ethyl]-3-iodo-pyrazolo[3,4-d]pyrimidin-4-amine (50 mg, 0.1205 mmol) in dioxane/water (4.5/0.5 ml) was added 4-(Carboxymethyl)phenylboronic acid pinacol ester (1.5 eq., 47.4 mg, 0.181 mmol), potassium carbonate (1.5 eq., 25.0 mg, 0.181 mmol) and triphenylphosphine (20 mol %, 9.5 mg) followed by palladium acetate (5 mol %) and the mixture heated in the microwave at 120° C. for 30 mins. The mixture was concentrated in vacuo and purified by column chromatography, MeOH/DCM (10% then 0-50 drops of $NEt_3$ per 100 ml) to give a cream solid, (25.0 mg, 0.0591 mmol, 49.0%). $^1$H NMR (500 MHz, MeOD) δ 8.26 (s, 1H), 7.59 (d, J=8.2, 2H), 7.49 (d, J=8.2, 2H), 4.55 (t, J=6.3, 2H), 3.62 (s, 2H), 3.20-3.15 (m, 2H), 2.98 (t, J=6.3, 3H), 2.74 (s, 6H), 2.18 (t, J=11.0, 2H), 2.03-1.96 (m, 2H), 1.56 (dd, J=12.1, 3.9, 2H); $^{13}$C NMR (126 MHz, MeOD) δ 177.81 (C), 158.57 (C), 155.42 (CH), 154.16 (C), 145.31 (C), 139.11 (C), 130.29 (C), 129.88 (2×CH), 128.10 (2×CH), 97.82 (C), 63.29 ($CH_2$), 55.78 ($CH_2$), 51.37 (2×$CH_2$), 44.08 ($CH_2$), 39.26 (2×$CH_3$), 29.53 (CH), 26.34 (2×$CH_2$); MS (ES +ve) [M+H]$^+$: 424.4; HRMS (ES +ve), $C_{22}H_{30}N_7O_2$ [M+H]$^+$: calculated 424.24555, found 424.2475.

To a solution of 1-[2-[4-(dimethylamino)-1-piperidyl]ethyl]-3-iodo-pyrazolo[3,4-d]pyrimidin-4-amine (50 mg, 0.1205 mmol) in dioxane/water (4.5/0.5 ml) was added [3-(tert-butoxycarbonylamino)-4-methoxy-phenyl]boronic acid (1.5 eq., 48.4 mg, 0.181 mmol), potassium carbonate (1.5 eq., 25.0 mg, 0.181 mmol) and triphenylphosphine (20 mol %, 9.5 mg) followed by palladium acetate (5 mol %) and the mixture heated in the microwave at 120° C. for 30 mins. The mixture was concentrated in vacuo and purified by column chromatography, MeOH/DCM (0-10% then 0-20 drops of $NEt_3$ per 100 ml) to give a light brown solid, (32.9 mg, 0.0645 mmol, 53.5%). $^1$H NMR (500 MHz, MeOD) δ 8.26 (d, J=5.2, 1H), 8.19 (d, J=2.1, 1H), 7.41 (dd, J=8.4, 2.2, 1H), 7.19 (d, J=8.5, 1H), 4.56 (t, J=6.6, 2H), 3.99 (d, J=5.1, 3H), 3.15 (d, J=12.1, 2H), 2.96 (t, J=6.6, 2H), 2.54 (m, 1H), 2.48 (s, 6H), 2.16 (t, J=10.9, 2H), 1.92 (d, J=10.5, 2H), 1.56 (d, J=5.1, 9H), 1.55-1.46 (m, 2H); $^{13}$C NMR (126 MHz, MeOD) δ 158.48 (C), 155.35 (CH), 154.20 (C), 153.82 (C), 149.93 (C), 145.03 (C), 128.25 (C), 124.95 (C), 123.27 (CH), 119.69 (CH), 111.00 (CH), 97.67 (C), 80.15 (C), 62.52 (CH), 56.07 ($CH_2$), 55.11 ($CH_3$), 51.99 (2×$CH_2$), 44.01 ($CH_2$), 39.86 (2×$CH_3$), 27.22 (3×$CH_3$), 27.03 (2×$CH_2$); MS (ES +ve) [M+H]$^+$: 511.4; HRMS (ES +ve), $C_{26}H_{39}N_8O_3$ [M+H]$^+$: calculated 511.31396, found 511.3166.

tert-butyl 2-[4-[4-amino-1-[2-[4-(dimethylamino)-1-piperidyl]ethyl]pyrazolo[3,4-d]pyrimidin-3-yl]-2-methoxy-phenyl]acetate (565)

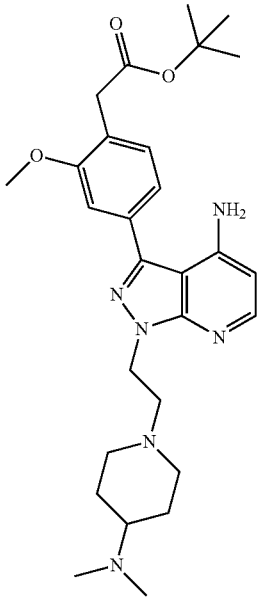 [SMILES: COc1cc(-c2nn(CCN3CCC(N(C)C)CC3)c3nccc(N)c23)ccc1CC(=O)OC(C)(C)C]

To a solution of 1-[2-[4-(dimethylamino)-1-piperidyl]ethyl]-3-iodo-pyrazolo[3,4-d]pyrimidin-4-amine (34.7 mg, 0.0836 mmol) in dioxane/water (4.5/0.5 ml) was added tert-butyl 2-[2-methoxy-4-(4,4,5,5-tetramethyl-1,3,2-dioxaborolan-2-yl)phenyl]acetate (1 eq., 29.1 mg, 0.0836 mmol), potassium carbonate (1.5 eq., 17.3 mg, 0.125 mmol) and triphenylphosphine (20 mol %, 4.4 mg) followed by palladium acetate (5 mol %) and the mixture heated in the microwave at 120° C. for 30 mins. The mixture was concentrated in vacuo and purified by column chromatography, MeOH/DCM (0-10% then 0-30 drops of NEt$_3$ per 100 ml) to give a cream solid, (19 mg, 0.0373 mmol, 44.6%). $^1$H NMR (500 MHz, MeOD) δ 8.26 (s, 1H), 7.35 (d, J=7.6, 1H), 7.26 (d, J=1.4, 1H), 7.22 (dd, J=7.5, 1.6, 1H), 4.56 (t, J=6.7, 2H), 3.91 (s, 3H), 3.64 (s, 2H), 3.13 (d, J=11.9, 2H), 2.94 (t, J=6.7, 2H), 2.37 (m, 7H), 2.13 (t, J=11.0, 2H), 1.91-1.85 (m, 2H), 1.48 (m, 11H); $^{13}$C NMR (126 MHz, MeOD) δ 172.07 (C), 158.55 (C), 158.18 (C), 155.46 (CH), 154.14 (C), 145.09 (C), 133.02 (C), 131.48 (CH), 124.76 (C), 120.21 (CH), 110.45 (CH), 97.82 (C), 80.76 (C), 62.26 (CH), 56.22 (CH$_2$), 54.70 (CH$_3$), 52.24 (2×CH$_2$), 44.04 (CH$_2$), 40.09 (2×CH$_3$), 36.61 (CH$_2$), 27.28 (2×CH$_2$), 26.90 (3×CH$_3$); MS (ES +ve) [M+H]$^+$: 510.2; HRMS (ES +ve), C$_{27}$H$_{40}$N$_7$O$_3$ [M+H]$^+$: calculated 510.31872, found 510.3185.

3-iodo-1-[2-(4-methylpiperazin-1-yl)ethyl]pyrazolo[3,4-d]pyrimidin-4-amine

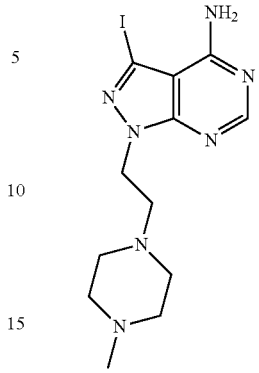

100 mg, 0.265 mmol of 1-(2,2-diethoxyethyl)-3-iodo-pyrazolo[3,4-d]pyrimidin-4-amine was added to a 5 ml microwave tube. 2.5 ml of water and 2.5 ml of TFA were then added and the mixture heated to 100° C. for 30 mins in the microwave. The solvents were removed in vacuo to give a dark brown oil. 0.265 mmol of 2-(4-amino-3-iodo-pyrazolo[3,4-d]pyrimidin-1-yl)acetaldehyde was suspended in 3 ml of DCM. 1-methylpiperizine (1.5 eq., 0.399 mmol, 39.8 mg, 44.1 ul) was added followed by a drop of acetic acid and the mixture allowed to stir for 10 mins. Sodium triacetoxyborohydride (1.5 eq., 0.399 mmol, 84.6 mg) was added and the mixture allowed to stir for 17 hours overnight. The mixture was concentrated in vacuo and purified by column chromatography, MeOH/DCM (5-10% then 0-15 drops of NEt$_3$ per 100 ml) to give a light orange thick oil, (89.1 mg, 0.2302 mmol, 86.9%). $^1$H NMR (500 MHz, MeOD) δ 8.22 (s, 1H), 4.51 (t, J=6.0, 2H), 3.33 (d, J=1.7, 4H), 3.20-3.04 (m, 4H), 2.98 (t, J=6.0, 2H), 2.83 (s, 3H); 3C NMR (126 MHz, MeOD) δ 158.05 (C), 155.67 (CH), 153.80 (C), 103.55 (C), 87.02 (C), 55.51 (CH$_2$), 53.44 (CH$_2$), 49.45 (CH$_2$), 44.18 (CH$_2$), 43.07 (CH$_2$), 42.03 (CH$_3$); MS (ES +ve) (M+H)$^+$: 388.4.

1-[2-[4-(dimethylamino)-1-piperidyl]ethyl]-3-[3-methoxy-4-[(5-methyloxazol-2-yl)methyl]phenyl]pyrazolo[3,4-d]pyrimidin-4-amine (584)

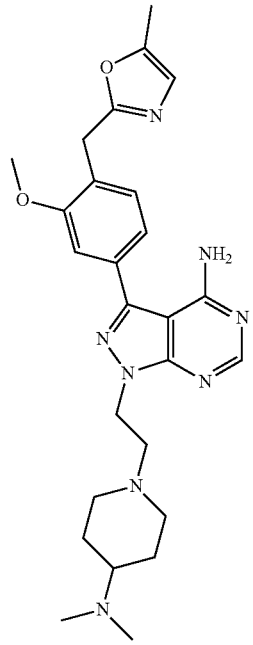 [SMILES: COc1cc(-c2nn(CCN3CCC(N(C)C)CC3)c3ncnc(N)c23)ccc1Cc1ncc(C)o1]

To a solution of 1-[2-[4-(dimethylamino)-1-piperidyl]ethyl]-3-iodo-pyrazolo[3,4-d]pyrimidin-4-amine (50 mg, 0.1205 mmol) in dioxane/water (4.5/0.5 ml) was added 2-[[2-methoxy-4-(4,4,5,5-tetramethyl-1,3,2-dioxaborolan-2-yl)phenyl]methyl]-5-methyl-oxazole (1 eq., 39.7 mg, 0.1205 mmol), potassium carbonate (1.5 eq., 25.0 mg, 0.181 mmol) and triphenylphosphine (20 mol %, 9.5 mg) followed by palladium acetate (5 mol %) and the mixture heated in the microwave at 120° C. for 30 mins. The mixture was concentrated in vacuo and purified by column chromatography, MeOH/DCM (10% then 0-30 drops of NEt$_a$ per 100 ml) to give a pale yellow solid, (36.8 mg, 0.0751 mmol, 62.3%). $^1$H NMR (500 MHz, MeOD) δ 8.28 (s, 1H), 7.38 (d, J=7.6, 1H), 7.29 (s, 1H), 7.26 (dd, J=7.6, 1.6, 1H), 6.69 (d, J=1.2, 1H), 4.57 (t, J=6.6, 2H), 4.15 (s, 2H), 3.91 (s, 3H), 3.17 (d, J=7.4, 2H), 2.96 (t, J=6.6, 2H), 2.69 (m, 1H), 2.56 (s, 6H), 2.31 (s, 3H), 2.17 (t, J=11.0, 2H), 1.94 (m, 2H), 1.54 (m, 2H); $^{13}$C NMR (126 MHz, MeOD) δ 162.54 (C), 158.55 (C), 157.95 (C), 155.47 (CH), 154.21 (C), 149.33 (C), 145.01 (C), 133.18 (C), 130.96 (CH), 124.85 (C), 121.56 (CH), 120.34 (CH), 110.70 (CH), 97.78 (C), 62.77 (CH), 56.03 (CH$_2$), 54.78 (CH$_3$), 51.82 (2×CH$_2$), 44.08 (CH$_2$), 39.66 (2×CH$_3$), 28.17 (CH$_2$), 26.79 (2×CH$_2$), 9.16 (CH$_3$); MS (ES +ve) [M+H]$^+$: 491.8; HRMS (ES +ve), C$_{26}$H$_{35}$N$_8$O$_2$ [M+H]$^+$: calculated 491.28775, found 491.2862.

3-iodo-1-[2-(4-methoxy-1-piperidyl)ethyl]pyrazolo[3,4-d]pyrimidin-4-amine

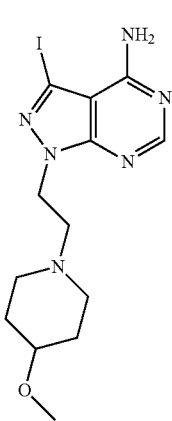 [SMILES: COC1CCN(CCn2nc(I)c3c(N)ncnc32)CC1]

100 mg, 0.287 mmol of 1-(2,2-dimethoxyethyl)-3-iodo-pyrazolo[3,4-d]pyrimidin-4-amine was added to a 5 ml microwave tube. The mixture was then concentrated in vacuo. 0.287 mmol of 2-(4-amino-3-iodo-pyrazolo[3,4-d]pyrimidin-1-yl)acetaldehyde was suspended in 3 ml of DCM. 4-methoxypiperidine (1.5 eq., 0.430 mmol, 49.5 mg) was added followed by a drop of acetic acid and the mixture allowed to stir for 10 mins. Sodium triacetoxyborohydride (1.5 eq., 0.430 mmol, 91.1 mg) was then added and the mixture allowed to stir for 72 hours. The product was concentrated in vacuo and the product purified by column chromatography, MeOH/DCM (0-8%) to give a pale yellow solid, (112 mg, 0.279 mmol, 97.1%). $^1$H NMR (500 MHz, MeOD) δ 8.23 (s, 1H), 4.53 (t, J=6.6, 2H), 3.29 (s, 3H), 2.98 (t, J=6.5, 2H), 2.91 (s, 2H), 2.45 (s, 2H), 1.89 (s, 2H), 1.57 (s, 2H); $^{13}$C NMR (126 MHz, MeOD) δ 158.09 (C), 155.71 (CH), 153.68 (C), 103.71 (C), 87.16 (C), 75.13 (CH), 56.19 (CH$_2$), 54.43 (CH$_3$), 50.24 (2×CH$_2$), 43.96 (CH$_2$), 29.68 (2×CH$_2$); MS (ES +ve) (M+H)$^+$: 403.0.

tert-butyl N-[4-[4-amino-1-[2-(4-methoxy-1-piperidyl)ethyl]pyrazolo[3,4-d]pyrimidin-3-yl]-2-methoxy-phenyl]carbamate (593)

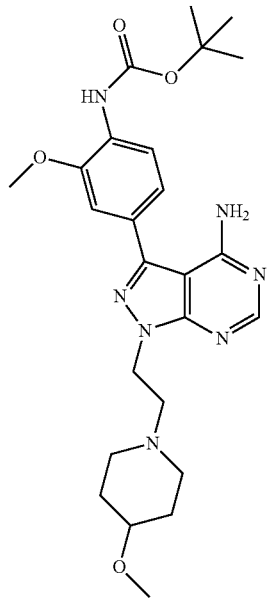 [SMILES: COc1cc(-c2nn(CCN3CCC(OC)CC3)c3ncnc(N)c23)ccc1NC(=O)OC(C)(C)C]

To a solution of 3-iodo-1-[2-(4-methoxy-1-piperidyl)ethyl]pyrazolo[3,4-d]pyrimidin-4-amine (50 mg, 0.124 mmol) in dioxane/water (4.5 ml/0.5 ml) was added [4-(tert-butoxycarbonylamino)-3-methoxy-phenyl]boronic acid (1.5 eq., 49.8 mg, 0.187 mmol), potassium carbonate (1.5 eq., 25.8 mg, 0.181 mmol) and triphenylphosphine (20 mol %, 6.5 mg) followed by palladium acetate (5 mol %) and the mixture heated in the microwave at 120° C. for 30 mins. The mixture was concentrated in vacuo and purified by column chromatography, MeOH/DCM (0-10%) to give a cream coloured solid, (60.0 mg, 0.121 mmol, 97.3%). $^1$H NMR (500 MHz, MeOD) δ 8.29 (s, 1H), 8.08 (d, J=8.2, 1H), 7.31 (d, J=1.8, 1H), 7.27 (dd, J=8.2, 1.8, 1H), 4.63 (t, J=6.6, 2H), 3.98 (s, 3H), 3.34 (s, 3H), 3.12 (m, 2H), 3.02 (m, 2H), 2.60 (m, 2H), 1.93 (m, 2H), 1.65 (m, 2H), 1.57 (s, 9H); $^{13}$C NMR (126 MHz, MeOD) δ 158.53 (C), 155.46 (CH), 154.22 (C), 153.42 (C), 149.28 (C), 145.17 (C), 128.73 (C), 127.38 (C), 120.44 (CH), 119.50 (CH), 110.33 (CH), 97.94 (C), 80.15 (C), 75.12 (CH), 56.21 (CH$_2$), 55.10 (CH), 54.79 (CH$_3$), 50.02 (2×CH$_2$), 43.60 (CH$_2$), 29.69 (2×CH$_2$), 27.21 (3×CH$_3$); MS (ES +ve) [M+H]$^+$: 498.2; HRMS (ES +ve), C$_{25}$H$_{35}$N$_7$O$_4$ [M+H]$^+$: calculated 498.28233, found 498.2850.

1-(2,2-dimethoxyethyl)-3-iodo-pyrazole

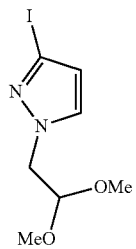 [SMILES: COC(Cn1ccc(I)n1)OC]

To a solution of 3-iodo-1H-pyrazole (500 mg, 2.578 mmol) in DMF (10 ml) was added sodium hydride (1.5 eq., 3.867 mol, 60% dispersion in mineral oil, 154.7 mg) and the suspension allowed to stir for 30 mins until the gas evolution had subsided. Bromoacetaldehyde dimethyl acetal (1.5 eq. 3.867 mmol, 649.6 mg, 0.454 ml) was then added dropwise and the mixture heated at 150° C. in the microwave for an hour. The mixture was concentrated in vacuo in order to remove as much DMF as possible. EtOAc and water were then added to the mixture and the organic layer separated. The aqueous layer was washed twice with EtOAc and organics combined, dried over MgSO$_4$ and concentrated in vacuo. The product was purified by column chromatography, MeOH/DCM (0-1%) to give a light orange solid, (519.2 mg, 1.841 mmol, 71.4%). $^1$H NMR (500 MHz, CDCl3) δ 7.28 (d, J=2.3, 1H), 6.40 (d, J=2.3, 1H), 4.62 (t, J=5.4, 1H), 4.20 (d, J=5.4, 2H), 3.37 (d, J=2.4, 6H); $^{13}$C NMR (126 MHz, CDCl3) δ 132.61 (CH), 114.84 (CH), 103.29 (CH$_2$), 94.49 (C), 55.20 (2×CH$_3$), 54.55 (CH); MS (ES +ve) (M+H)$^+$: 304.6 (+Na).

1-[2-(3-iodopyrazol-1-yl)ethyl]-N,N-dimethyl-piperidin-4-amine

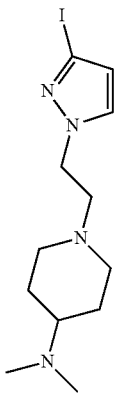 [SMILES: CN(C)C1CCN(CCn2ccc(I)n2)CC1]

1-(2,2-dimethoxyethyl)-3-iodo-pyrazole (250 mg, 0.887 mmol) was added to a microwave vial followed by water (0.25 ml) and TFA (0.25 ml) and the mixture heated to 100° C. in the microwave for an hour. The product was concentrated in vacuo and used without further purification. 0.887 mmol of 2-(3-iodopyrazol-1-yl)acetaldehyde was suspended in 5 ml of DCM. N,N-dimethylpiperidine-4-amine (1.5 eq., 1.33 mmol, 170.5 mg) was added followed by a drop of acetic acid and the mixture allowed to stir for 10 mins. Sodium triacetoxyborohydride (1.5 eq., 1.33 mmol, 281.9 mg) was added and the mixture allowed to stir for 72 hours. The mixture was concentrated in vacuo and purified by column chromatography, MeOH/DCM (5-10% then 10-20 drops of NEt$_3$ per 100 ml) to give a thick light orange oil, (306.3 mg, 0.880 mmol, 99.2%). $^1$H NMR (500 MHz, MeOD) δ 7.54 (d, J=2.3, 1H), 6.43 (d, J=2.3, 1H), 4.27 (t, J=6.4, 2H), 3.10-3.05 (m, 1H), 3.05-2.99 (m, 2H), 2.85-2.76 (m, 8H), 2.17 (td, J=12.0, 2.3, 2H), 2.01 (d, J=13.2, 2H), 1.67 (tt, J=12.1, 6.1, 2H); $^{13}$C NMR (126 MHz, MeOD) δ 132.70 (CH), 114.34 (CH), 93.40 (C), 63.39 (CH), 56.57 (CH$_2$), 51.40 (2×CH$_2$), 49.59 (CH$_2$), 39.17 (2×CH$_2$), 26.24 (CH$_2$); MS (ES +ve) (M+H)$^+$: 348.8.

tert-butyl N-[4-[1-[2-[4-(dimethylamino)-1-piperidyl]ethyl]pyrazol-3-yl]-2-methoxy-phenyl]carbamate (597)

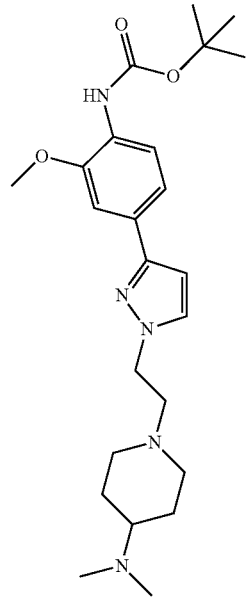 [SMILES: COc1cc(-c2ccn(CCN3CCC(N(C)C)CC3)n2)ccc1NC(=O)OC(C)(C)C]

To a solution of 1-[2-(3-iodopyrazol-1-yl)ethyl]-N,N-dimethyl-piperidin-4-amine (50 mg, 0.1436 mmol) in dioxane/water (4.5 ml/0.5 ml) was added [4-(tert-butoxycarbonylamino)-3-methoxy-phenyl]boronic acid (1.5 eq., 57.6 mg, 0.215 mmol), potassium carbonate (1.5 eq., 29.7 mg, 0.215 mmol) and triphenylphosphine (20 mol %, 7.5 mg) followed by palladium acetate (5 mol %) and the mixture heated in the microwave at 120° C. for an hour. The reaction was concentrated in vacuo and purified by column chromatography, MeOH/DCM (5-10%) to give a dark orange solid, (42.7 mg, 0.0963 mmol, 67.1%). $^1$H NMR (500 MHz, MeOD) δ 7.88 (s, 1H), 7.69 (d, J=2.3, 1H), 7.42 (d, J=1.7, 1H), 7.33 (dd, J=8.3, 1.8, 1H), 6.62 (d, J=2.3, 1H), 4.33 (t, J=6.4, 2H), 3.96 (s, 3H), 3.22-3.15 (m, 11H), 3.11 (s, 2H), 2.94 (s, 2H), 2.85 (d, J=14.6, 6H), 2.26 (s, 2H), 2.05 (s, 2H), 1.73 (d, J=8.3, 2H), 1.55 (d, J=4.2, 9H); $^{13}$C NMR (126 MHz, MeOD) δ 153.56 (C), 151.55 (C), 149.10 (C), 131.77 (CH), 128.50 (C), 127.36 (C), 123.00 (C), 119.24 (CH), 117.75 (CH), 107.31 (CH), 102.25 (CH), 63.48 (CH), 56.69 (CH$_2$), 54.95 (CH$_3$), 51.21 (2×CH$_2$), 49.11 (CH$_2$), 39.19 (2×CH$_3$), 27.23 (3×CH$_3$), 26.22 (2×CH$_2$); MS (ES +ve) (M+H)$^+$: 444.2; HRMS (ES +ve), C$_{24}$H$_{38}$N$_5$O$_3$(M+H)$^+$: calculated 444.29692, found 444.29650.

2-[4-[4-amino-1-[2-[4-(dimethylamino)-1-piperidyl]ethyl]pyrazolo[3,4-d]pyrimidin-3-yl]phenyl]acetonitrile (5-100)

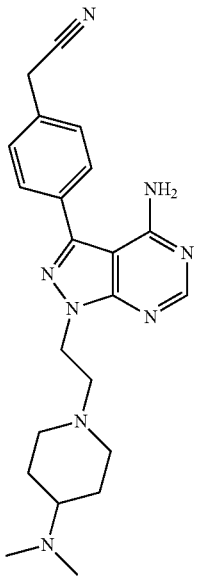 [SMILES: CN(C)C1CCN(CCn2nc(-c3ccc(CC#N)cc3)c3c(N)ncnc32)CC1]

To a solution of 1-[2-[4-(dimethylamino)-1-piperidyl]ethyl]-3-iodo-pyrazolo[3,4-d]pyrimidin-4-amine (50 mg, 0.1205 mmol) in dioxane/water (4.5/0.5 ml) was added 4-(Cyanomethyl)benzeneboronic acid, (1 eq., 29.1 mg, 0.181 mmol), potassium carbonate (1.5 eq., 25.0 mg, 0.181 mmol) and triphenylphosphine (20 mol %, 9.5 mg) followed by palladium acetate (5 mol %) and the mixture heated in the microwave at 120° C. for 30 mins. The mixture was concentrated in vacuo and purified by column chromatography, MeOH/DCM (5-10% then 20 drops of $NEt_3$ per 100 ml) to give a cream solid, (41.8 mg, 0.1034 mmol, 85.8%). $^1$H NMR (500 MHz, MeOD) δ 8.27 (s, 1H), 7.79-7.70 (m, 2H), 7.59 (d, J=8.3, 2H), 4.56 (t, J=6.4, 2H), 4.03 (s, 2H), 3.18 (d, J=5.8, 2H), 3.04-2.93 (m, 3H), 2.74 (s, 6H), 2.17 (dd, J=15.1, 6.9, 2H), 1.99 (d, J=12.8, 2H), 1.61-1.51 (m, 2H); $^{13}$C NMR (126 MHz, MeOD) δ 158.49 (C), 155.47 (CH), 154.36 (C), 144.35 (C), 132.22 (C), 128.84 (2×CH), 128.70 (2×CH), 117.95 (C), 110.00 (C), 97.74 (C), 63.27 (CH), 55.84 ($CH_2$), 51.39 (2×$CH_2$), 44.11 ($CH_2$), 39.27 (2×$CH_3$), 26.32 (2×$CH_2$), 21.98 ($CH_2$); MS (ES +ve) [M+H]$^+$: 405.0; HRMS (ES +ve), $C_{22}H_{29}N_8$ (M+H)$^+$: calculated 405.25097, found 405.24950.

1-[2-[3-(dimethylamino)-1-piperidyl]ethyl]-3-iodo-pyrazolo[3,4-d]pyrimidin-4-amine

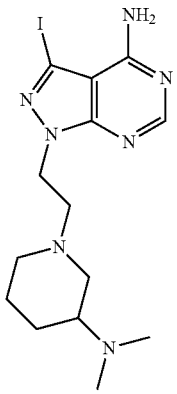 [SMILES: CN(C)C1CCCN(CCn2nc(I)c3c(N)ncnc32)C1]

100 mg, 0.287 mmol of 1-(2,2-dimethoxyethyl)-3-iodo-pyrazolo[3,4-d]pyrimidin-4-amine was added to a 5 ml microwave tube. 2.5 ml of water and 2.5 ml of TFA were then added and the mixture heated to 100° C. for 30 mins in the microwave. The product was then concentrated in vacuo. 0.287 mmol of 2-(4-amino-3-iodo-pyrazolo[3,4-d]pyrimidin-1-yl)acetaldehyde was suspended in 3 ml of DCM. 3-dimethylaminopiperidine (1.5 eq., 0.430 mmol, 55.1 mg) was added followed by a drop of acetic acid and the mixture allowed to stir for 10 mins. Sodium triacetoxyborohydride (1.5 eq., 0.430 mmol, 91.1 mg) was added and the mixture allowed to stir for 18 hours. The mixture was concentrated in vacuo and purified by column chromatography, MeOH/DCM (5-10%) to give a cream solid, (117.5 mg, 0.283 mmol, 98.6%). $^1$H NMR (500 MHz, MeOD) δ 8.22 (s, 1H), 4.54-4.43 (m, 2H), 3.08 (m, 1H), 2.99-2.90 (m, 3H), 2.84 (s, 6H), 2.65 (m, 2H), 2.38 (m, 1H), 1.88 (m, 1H), 1.75-1.65 (m, 2H), 1.55-1.47 (m, 1H); $^{13}$C NMR (126 MHz, MeOD) δ 158.13 (C), 155.80 (CH), 153.62 (C), 103.65 (C), 87.01 (C), 62.48 (CH), 56.37 ($CH_2$), 52.78 ($CH_2$), 52.75 ($CH_2$), 44.50 ($CH_2$), 40.40 (2×$CH_3$), 24.67 ($CH_2$), 21.95 ($CH_2$); MS (ES +ve) (M+H)$^+$: 415.8 tert-butyl N-[4-[4-amino-1-[2-[3-(dimethylamino)-1-piperidyl]ethyl]pyrazolo[3,4-d]pyrimidin-3-yl]-2-methoxy-phenyl]carbamate (5-103)

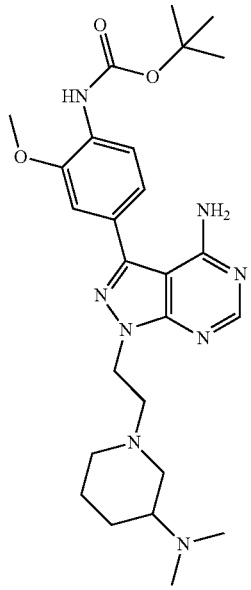 [SMILES: COc1cc(-c2nn(CCN3CCCC(N(C)C)C3)c3ncnc(N)c23)ccc1NC(=O)OC(C)(C)C]

To a solution of 1-[2-[3-(dimethylamino)-1-piperidyl]ethyl]-3-iodo-pyrazolo[3,4-d]pyrimidin-4-amine (50 mg, 0.1205 mmol) in dioxane/water (4.5 ml/0.5 ml) was added [4-(tert-butoxycarbonylamino)-3-methoxy-phenyl]boronic acid (1.5 eq., 48.3 mg, 0.181 mmol), potassium carbonate (1.5 eq., 25.0 mg, 0.181 mmol) and triphenylphosphine (20 mol %, 9.5 mg) followed by palladium acetate (5 mol %) and the mixture heated in the microwave at 120° C. for 30 mins. The mixture was concentrated in vacuo and purified by column chromatography, MeOH/DCM (5-10%) to give a dark red solid, (60.5 mg, 0.119 mmol, 98.4%). $^1$H NMR (500 MHz, MeOD) δ 8.25 (s, 1H), 8.05 (d, J=8.2, 1H), 7.26 (d, J=1.8, 1H), 7.22 (dd, J=8.2, 1.8, 1H), 4.58-4.48 (m, 2H), 3.94 (s, 3H), 3.13 (m, 1H), 2.97 (m, 3H), 2.82 (s, 6H), 2.66

(m, 2H), 2.42 (m, 1H), 1.86 (m, 1H), 1.71 (m, 2H), 1.52 (m, 10H); $^{13}$C NMR (126 MHz, MeOD) δ 158.61 (C), 155.59 (CH), 154.11 (C), 153.49 (C), 149.33 (C), 145.10 (C), 128.93 (C), 127.24 (C), 120.44 (CH), 119.66 (CH), 110.28 (CH), 97.76 (C), 80.24 (C), 62.58 (CH), 56.39 (CH$_2$), 55.12 (CH$_3$), 52.86 (CH$_2$), 52.73 (CH$_2$), 44.28 (CH$_2$), 40.32 (2×CH$_3$), 27.20 (3×CH$_3$), 24.59 (CH$_2$), 21.84 (CH$_2$); MS (ES +ve) [M+H]$^+$: 511.0; HRMS (ES +ve), C$_{26}$H$_{39}$N$_8$O$_3$ (M+H)$^+$: calculated 511.31396, found 511.31140.

Biological Methods & Materials

Cell Culture General

Cells were grown in Dulbecco's Modified Eagle Medium (DMEM) or Roswell Park Memorial Institute (RPMI) medium supplemented with serum (10% fetal bovine serum) and L-glutamine (2 mM) and incubated in a Heracell 240i tissue culture incubator at 37° C. and 5% CO$_2$.

Cell Viability Assay

Cells were plated in 96-well plates at 2000 cells/well in 100 μl of DMEM or RPMI medium containing 10% FBS and 2 mM L-glutamine and incubated for 48 h in an incubator at 37° C. and 5% CO$_2$. After 48 hours, the media was aspirated from each well and replaced with 95 μl of fresh medium. Compounds, including DMSO, were prepared at 20× in DMEM medium in a separate 96-well intermediate plate. 5 μl from the intermediate plate was then added to each well containing cells. Untreated cells were incubated with DMSO (0.1% v/v). After 5 days, PrestoBlue™ cell viability reagent (10 μl) was added to each well and the plates incubated for 60-90 min. Fluorescence emission was detected using a fluorescence plate reader (excitation 540 nm, emission 590 nm). All conditions were normalised to the untreated cells (100%) and dose-response curves were fitted using GraphPad Prism software.

Apoptosis Assay—Using the IncuCyte-ZOOM® System from Essen BioScience

Cells were plated in 96-well Nunc™ black optical-bottom plates (Thermo Scientific) at 3000 cells/well in 100 μl of DMEM or RPMI medium containing 10% FBS and 2 mM L-glutamine and incubated for 48 h in an incubator at 37° C. and 5% CO$_2$. The media was replaced with 95 μl of fresh media containing NucView™ 488 at 1 μM concentration and drugs or DMSO added along a concentration gradient, as described in the cell viability assay, and the plates placed in the IncuCyte for incubation. Cell growth and apoptosis was monitored over 5 days using brightfield and green fluorescence channels (excitation 460 nm, emission 524 nm) microscopy. Cell confluence (brightfield) and apoptotic (green) count was performed by the IncuCyte software.

Cell Cycle Assay

Cells were plated at 5000 cell/well in 100 μl of DMEM or RPMI medium containing 10% FBS and 2 mM L-glutamine in 96-well Nunc™ black optical-bottom plates and incubated at 37° C. with 5% CO$_2$. After 48 hours, the media was aspirated off and replaced with 95 μl of fresh media. Compounds, including DMSO, were prepared at 20× in DMEM or RMPI medium in a separate plate and 5 μl then added to each well containing cells. Untreated cells were incubated with DMSO (0.1% v/v). The cells were incubated for 24 hours at 37° C. then 100 μl of 8% PFA in PBS was added to each well and left to incubate at room temperature for 20 mins. The media/PFA was removed and wells washed with 100 μl of PBS (×3). 100 μl of blocking buffer (PBS containing 1.1% BSA and 0.2% Trixton X100) was added to each well and left for 30 minutes. 30 μl of a primary antibody solution containing anti-Cyclin B1 mixed mouse monoclonal antibody (1:300) and anti-pHH3 rabbit polyclonal antibody (1:800) was added to each well and plates incubated for one hour at room temperature. The solution was then removed and wells washed with 100 μl of blocking buffer (×3). 100 μl of blocking buffer was added to each well and plates incubated for 30 minutes at room temperature. 30 μl of a secondary antibody solution containing 4 μg/ml of DAPI, AlexaFluor® 488 Donkey anti-mouse antibody (1:500) and AlexaFluor® 594 Goat anti-rabbit antibody (1:500) was added to each well and left to incubate for 45 mins at room temperature in the dark. The solution was then removed and plates washed with 100 μl of PBS (×3) and stored in 100 μl PBS in the dark until imaged. Images were acquired using the scan^R fluorescence microscope from Olympus or ImageXpress System from Molecular Devices and analysed using scan^R or ImageXpress software. Cells were sorted according to their cell cycle state by DNA content and intensity.

Western Blotting Protocol

Cells were plated at 1×10$^6$ cells/well in 2 ml of DMEM or RPMI medium containing 10% FBS and 2 mM L-glutamine in 6-well plates and incubated at 37° C. with 5% CO$_2$. After 24 hours, the media was aspirated and replaced with 2 ml of DMEM medium containing 0.1% FBS and 2 mM L-glutamine and the cells incubated for a further 24 hours. 2 μl of compounds dissolved in DMSO at appropriate concentration was then added to each well and plates incubated for 30 mins. 222 μl of FBS was then added to each well (giving a final concentration of 10%) and cells incubated for one hour. Cell lysates were then prepared using 100 μl of MD Anderson lysate buffer per well. The total cell protein concentration in each lysate was determined using Precision Red Advanced Protein Reagent #2 from Cytoskeleton. 25 μl of SDS-PAGE sample loading buffer, 10 μl of 1M DDT, lysate and water up to 100 μl to give solutions of 2-3 mg/ml were boiled at 100° C. for 3 mins. Samples were subjected to SDS-PAGE on BioRad 4-15% precast gels over 60 mins at 140 V and transferred to PVDF membranes over 150 mins at 210 mA. Membranes were blocked for an hour at room temperature using Roche's blocking buffer then primary antibodies added in 0.5% blocking buffer at 4° C. overnight. Membranes were washed with TBS/T (×3, 5 mins) then secondary antibody linked to horseradish peroxidase (HRP) added for an hour at room temperature. Following further washing with TBS/T (×3, 5 mins) and TBS (×2, 5 mins) HRP was detected by peroxidase enhanced chemiluminescence (POD ECL from Roche) and bands visualised using X-ray film or the ChemiDoc™ MP Imaging System from BioRad.

Cell Migration Assay

Cells were plated at 50000 cells/well in 100 μl of DMEM or RPMI medium containing 10% FBS and 2 mM L-glutamine in a 96-well ImageLock plate from Essen BioScience and left overnight to adhere in an incubator at 37° C. and 5% CO$_2$. Scratch wounds were created in each well using the WoundMaker™ supplied by Essen BioScience and each well washed with media (100 μl, ×2) to remove floating cells. 95 μl of fresh media was added in each well. Compounds, including DMSO, were prepared at 20× in DMEM medium in a separate plate and 5 μl then added to each well containing cells. Untreated cells were incubated with DMSO (0.1% v/v). Images were recorded every 30 mins using the IncuCyte-ZOOM™ for 24 hours. Analysis of wound width to monitor cell migration was performed using the IncuCyte software.

Zebrafish Assay

Wild-type zebrafish embryos were collected from AB-TPL breeding pairs and reared at 28° C. in E3 embryo media. The embryos, 2 days post fertilisation (dpf), were treated with compound 506 or Dasatinib at 100 μM, and DMSO (0.1% v/v) as negative control, for 2 hours prior to tail amputation. The tails were then clipped from the embryos. The embryos were incubated with drug for a further 2 hours before being washed off and replaced with fresh E3 media. The embryos were left to develop in E3 media at 28° C. for 2 days, after which, they were imaged by phase contrast microscopy.

Kinase Screening Assay

Compound $IC_{50}$ values were determined from 10-point, 1:3 dilution curves starting at either 100 μM or 10 μM with 10 μM ATP, by Reaction Biology Corp. For the whole kinome screen compounds were screened against 340 wild type kinases at a single dose of 1 μM, in duplicate, with 10 μM of ATP by Reaction Biology Corp. The data was averaged and plotted as percentage enzyme activity relative to DMSO, as negative control, using DiscoverRX TREEspot™ software.

Zebrafish PD/Toxicology Assay

Transgenic cldnb:EGFP zebrafish embryos were collected from breeding pairs and reared at 28° C. in E3 embryo media. 1 dpf embryos were treated with 506 or dasatinib at different doses (10-750 μM) at 20 hpf, 36 hpf and 48 hpf, or DMSO (0.1% v/v). Zebrafish embryos were imaged by fluorescent microscopy at 72 hpf. Safety assays. Wild-type zebrafish embryos were collected from AB-TPL breeding pairs and reared at 28° C. in E3 embryo media. 1 dpf embryos were treated with 506 or dasatinib at 100 μM, and DMSO (0.1% v/v) as negative control, for 4 h before being washed off and replaced with fresh E3 media. For PP20 treatment, the fish were incubated for 2 h post-amputation then replaced with fresh E3 media. The embryos were left to develop in E3 media at 28° C. for 2 d, after which, they were imaged by light microscopy. Zebrafish husbandry was performed under Home Office License in compliance with the Animals (Scientific Procedures) Act 1986 and approved by the University of Edinburgh Ethics Committee.

In Vivo PD Study

Tumor xenografts were generated in mice by injection of 2 million HCT116 cells subcutaneously. Tumors were allowed to grow until 3-4 mm in diameter. A daily dose of 50 mg/kg of 506 in pure water was administered by oral gavage. Mice were sacrificed 3 h after the last dose and tumors excised, fixed in 4% formaldehyde in 0.1 M phosphate buffer (pH 7.2), and embedded in paraffin. Sections were cut using a Reichert-Jung 1150/Autocut microtome to perform phospho-SRC immunochemistry. Antigen retrieval was performed using heat treatment under pressure in a microwave oven for 10 min in 10 mM citrate buffer pH=6. Sections were blocked for endogenous peroxidase followed by incubation with anti-phospho-SRC antibody (Cell Signaling Technology) (1:200 dilution) at 4° C. overnight. Staining was developed using EnVision (Dako) and diaminobenzidene (Dako) before slides were counterstained in haematoxylin, dehydrated and mounted in DPX. Slices were imaged on a NanoZoomer digital slide scanner, Hammamatsu. Staining was scored by a single experienced observer, blinded to treatment, using a weighted histoscore method.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

TABLE 1

Activities of Dasatinib and inhibitors with high SRC-over-ABL selectivity

| Code | Structure | Antiproliferative activity ($EC_{50}$) | Target inhibition ($IC_{50}$) |
|---|---|---|---|
| 109 | (structure shown) | MCF7: −<br>MDA-MB-231: ND<br>SYF (−/− Src): ND | ABL: −<br>BRK/PTK6: ND<br>KIT: −<br>mTOR: −<br>PDGFRa: −<br>RET: −<br>BLK: −<br>FGR: +<br>FRK/PTK5: +<br>FYN: +<br>HCK: −<br>LCK: +<br>LYN: +<br>SRC: +<br>YES: ++<br>$IC_{50}^{ABL}/IC_{50}^{SRC} = 50$ |

TABLE 1-continued

Activities of Dasatinib and inhibitors with high SRC-over-ABL selectivity

| Code | Structure | Antiproliferative activity (EC$_{50}$) | Target inhibition (IC$_{50}$) |
|---|---|---|---|
| 105 | 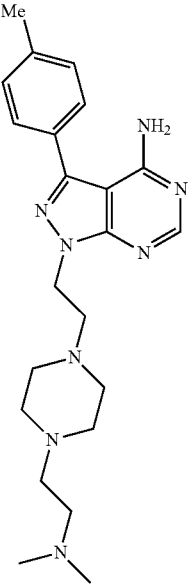 [SMILES: Cc1ccc(-c2nn(CCN3CCN(CCN(C)C)CC3)c3ncnc(N)c23)cc1] | MCF7: −<br>MDA-MB-231: ND<br>SYF (−/− Src): ND | ABL: −<br>BRK/PTK6: ND<br>KIT: −<br>mTOR: −<br>PDGFRa: −<br>RET: −<br>BLK: −<br>FGR: +<br>FRK/PTK5: −<br>FYN: +<br>HCK: −<br>LCK: −<br>LYN: +<br>SRC: +<br>YES: +<br>IC$_{50}^{ABL}$/IC$_{50}^{SRC}$ = 25 |
| 112 | 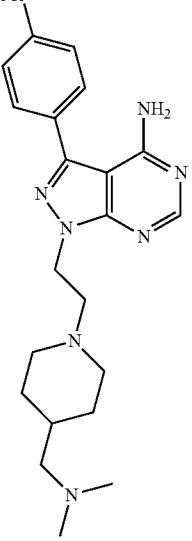 | MCF7: −<br>MDA-MB-231: ND<br>SYF (−/− Src): ND | ABL: −<br>BRK/PTK6: ND<br>KIT: −<br>mTOR: −<br>PDGFRa: −<br>RET: −<br>BLK: −<br>FGR: +<br>FRK/PTK5: −<br>FYN: +<br>HCK: −<br>LCK: −<br>LYN: −<br>SRC: +<br>YES: +<br>IC$_{50}^{ABL}$/IC$_{50}^{SRC}$ = 25 |

TABLE 1-continued

Activities of Dasatinib and inhibitors with high SRC-over-ABL selectivity

| Code | Structure | Antiproliferative activity ($EC_{50}$) | Target inhibition ($IC_{50}$) |
|---|---|---|---|
| 503 | 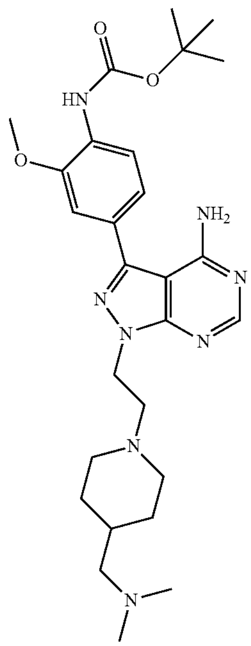 [SMILES: COc1cc(-c2nn(CCN3CCC(CN(C)C)CC3)c3ncnc(N)c23)ccc1NC(=O)OC(C)(C)C] | MCF7: ++<br>MDA-MB-231: ++<br>SYF (−/− Src): −<br>NCI-H358: ++<br>PC3: ND<br>HT1080: ND<br>MEF: +<br>BT549: ND | ABL: +<br>BRK/PTK6: ++<br>KIT: −<br>mTOR: −<br>PDGFRa: −<br>RET: −<br>BLK: +++<br>FGR: +++<br>FRK/PTK5: +++<br>FYN: +++<br>HCK: +++<br>LCK: +++<br>LYN: +++<br>SRC: +++<br>YES: +++<br>$IC_{50}^{ABL}/IC_{50}^{SRC} > 350$ |
| 506 | 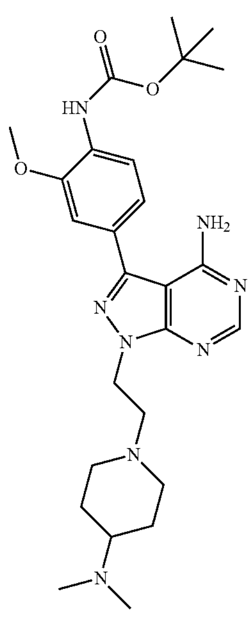 | MCF7: +++<br>MDA-MB-231: +++<br>SYF (−/− Src): −<br>NCI-H358: +++<br>PC3: +<br>HT1080: −<br>MEF: −<br>BT549: − | ABL: +<br>BRK/PTK6: ++<br>KIT: −<br>mTOR: −<br>PDGFRa: −<br>RET: −<br>BLK: +++<br>FGR: +++<br>FRK/PTK5: +++<br>FYN: +++<br>HCK: +++<br>LCK: +++<br>LYN: +++<br>SRC: +++<br>YES: +++<br>$IC_{50}^{ABL}/IC_{50}^{SRC} > 950$ |

TABLE 1-continued

Activities of Dasatinib and inhibitors with high SRC-over-ABL selectivity

| Code | Structure | Antiproliferative activity ($EC_{50}$) | Target inhibition ($IC_{50}$) |
|---|---|---|---|
| 518 | 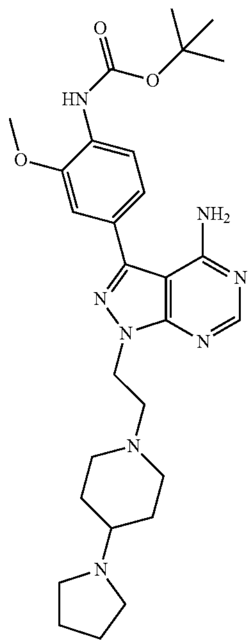 [SMILES: COc1cc(-c2nn(CCN3CCC(N4CCCC4)CC3)c3ncnc(N)c23)ccc1NC(=O)OC(C)(C)C] | MCF7: +++<br>MDA-MB-231: +++<br>SYF (−/− Src): − | ABL: +<br>BRK/PTK6: ++<br>KIT: −<br>mTOR: −<br>PDGFRa: −<br>RET: −<br>BLK: +++<br>FGR: +++<br>FRK/PTK5: +++<br>FYN: +++<br>HCK: +++<br>LCK: +++<br>LYN: +++<br>SRC: +++<br>YES: +++<br>$IC_{50}^{ABL}/IC_{50}^{SRC} > 800$ |
| 519 | 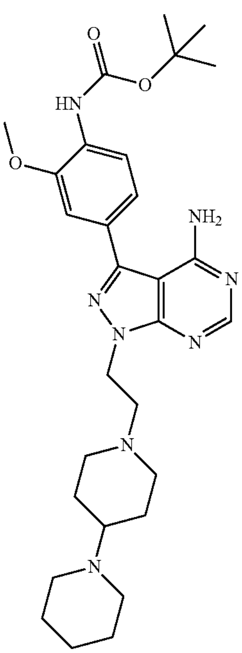 [SMILES: COc1cc(-c2nn(CCN3CCC(N4CCCCC4)CC3)c3ncnc(N)c23)ccc1NC(=O)OC(C)(C)C] | MCF7: ++<br>MDA-MB-231: +++<br>SYF (−/− Src): + | ABL: +<br>BRK/PTK6: ++<br>KIT: −<br>mTOR: −<br>PDGFRa: −<br>RET: −<br>BLK: +++<br>FGR: +++<br>FRK/PTK5: +++<br>FYN: +++<br>HCK: +++<br>LCK: +++<br>LYN: +++<br>SRC: +++<br>YES: +++<br>$IC_{50}^{ABL}/IC_{50}^{SRC} > 1,340$ |

TABLE 1-continued

Activities of Dasatinib and inhibitors with high SRC-over-ABL selectivity

| Code | Structure | Antiproliferative activity (EC$_{50}$) | Target inhibition (IC$_{50}$) |
|---|---|---|---|
| 526 | 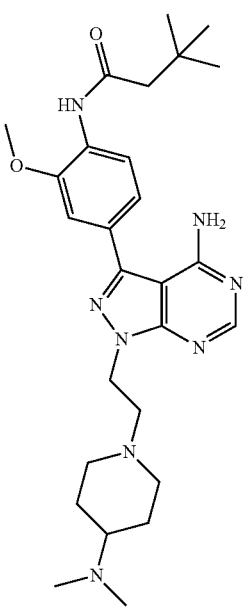 | MCF7: −<br>MDA-MB-231: −<br>SYF (−/− Src): − | ABL: −<br>BRK/PTK6: +<br>KIT: −<br>mTOR: −<br>PDGFRa: −<br>RET: −<br>BLK: +<br>FGR: ++<br>FRK/PTK5: −<br>FYN: +<br>HCK: +<br>LCK: ++<br>LYN: +<br>SRC: +<br>YES: ++<br>IC$_{50}^{ABL}$/IC$_{50}^{SRC}$ > 85 |
| 533 | 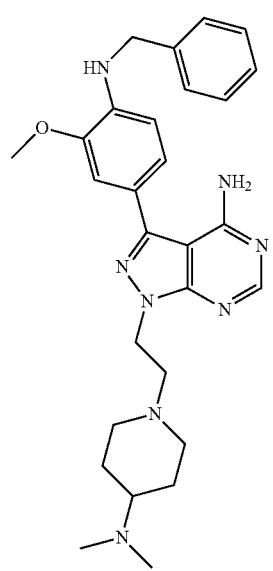 [SMILES: COc1cc(-c2nn(CCN3CCC(N(C)C)CC3)c3ncnc(N)c23)ccc1NCc1ccccc1] | MCF7: ++<br>MDA-MB-231: ++<br>SYF (−/− Src): + | ABL: −<br>BRK/PTK6: ++<br>KIT: +<br>mTOR: −<br>PDGFRa: −<br>RET: −<br>BLK: +++<br>FGR: +++<br>FRK/PTK5: +<br>FYN: +++<br>HCK: +++<br>LCK: +++<br>LYN: +++<br>SRC: +++<br>YES: +++<br>IC$_{50}^{ABL}$/IC$_{50}^{SRC}$ = 340 |

TABLE 1-continued

Activities of Dasatinib and inhibitors with high SRC-over-ABL selectivity

| Code | Structure | Antiproliferative activity ($EC_{50}$) | Target inhibition ($IC_{50}$) |
|---|---|---|---|
| 540 | 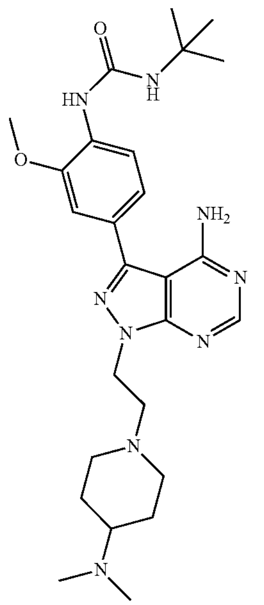 [SMILES: COc1cc(-c2nn(CCN3CCC(N(C)C)CC3)c3ncnc(N)c23)ccc1NC(=O)NC(C)(C)C] | MCF7: −<br>MDA-MB-231: −<br>SYF (−/− Src): − | ABL: −<br>BRK/PTK6: +<br>KIT: −<br>mTOR: −<br>PDGFRa: −<br>RET: −<br>BLK: +<br>FGR: ++<br>FRK/PTK5: −<br>FYN: +<br>HCK: +<br>LCK: ++<br>LYN: +<br>SRC: +<br>YES: ++<br>$IC_{50}^{ABL}/IC_{50}^{SRC} = 49$ |
| 543 | 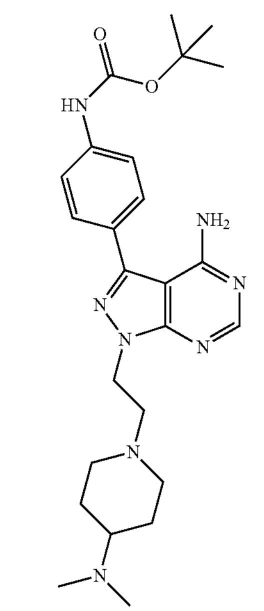 [SMILES: CN(C)C1CCN(CCn2nc(-c3ccc(NC(=O)OC(C)(C)C)cc3)c3c(N)ncnc32)CC1] | MCF7: +<br>MDA-MB-231: +<br>SYF (−/− Src): ND | ABL: −<br>BRK/PTK6: +<br>KIT: −<br>mTOR: −<br>PDGFRa: −<br>RET: −<br>BLK: +<br>FGR: +++<br>FRK/PTK5: +<br>FYN: +<br>HCK: +<br>LCK: ++<br>LYN: +<br>SRC: ++<br>YES: +++<br>$IC_{50}^{ABL}/IC_{50}^{SRC} > 50$ |

TABLE 1-continued

Activities of Dasatinib and inhibitors with high SRC-over-ABL selectivity

| Code | Structure | Antiproliferative activity (EC$_{50}$) | Target inhibition (IC$_{50}$) |
|---|---|---|---|
| 553 | 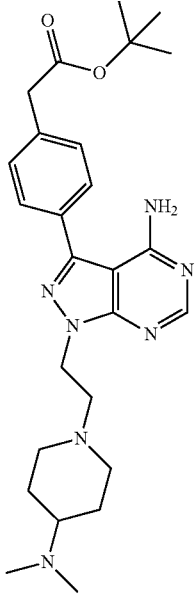 [SMILES: CN(C)C1CCN(CCn2nc(-c3ccc(CC(=O)OC(C)(C)C)cc3)c3c(N)ncnc32)CC1] | MCF7: +<br>MDA-MB-231: ++<br>SYF (−/− Src): − | ABL: −<br>BRK/PTK6: ++<br>KIT: −<br>mTOR: −<br>PDGFRa: −<br>RET: −<br>BLK: ++<br>FGR: +++<br>FRK/PTK5: ++<br>FYN: +++<br>HCK: ++<br>LCK: +++<br>LYN: +++<br>SRC: +++<br>YES: +++<br>IC$_{50}^{ABL}$/IC$_{50}^{SRC}$ > 2,850 |
| 565 | 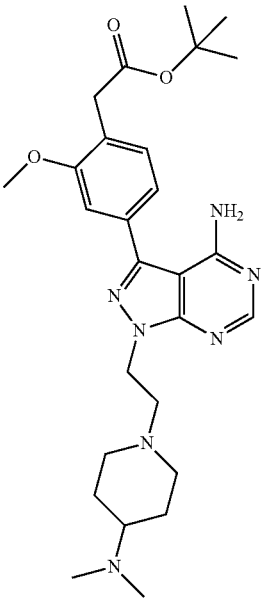 [SMILES: COc1cc(-c2nn(CCN3CCC(N(C)C)CC3)c3ncnc(N)c23)ccc1CC(=O)OC(C)(C)C] | MCF7: ++<br>MDA-MB-231: +++<br>SYF (−/− Src): − | ABL: +<br>BRK/PTK6: ++<br>KIT: −<br>mTOR: −<br>PDGFRa: −<br>RET: −<br>BLK: +++<br>FGR: +++<br>FRK/PTK5: +++<br>FYN: +++<br>HCK: ++<br>LCK: +++<br>LYN: +++<br>SRC: +++<br>YES: +++<br>IC$_{50}^{ABL}$/IC$_{50}^{SRC}$ > 350 |

TABLE 1-continued

Activities of Dasatinib and inhibitors with high SRC-over-ABL selectivity

| Code | Structure | Antiproliferative activity (EC$_{50}$) | Target inhibition (IC$_{50}$) |
|---|---|---|---|
| 584 | 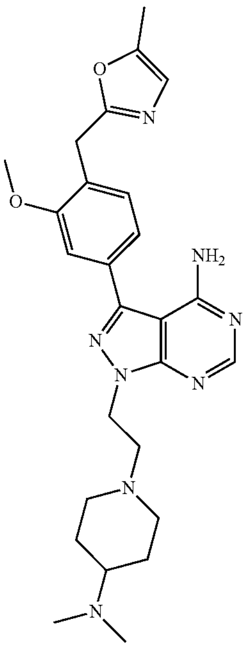 [SMILES: COc1cc(-c2nn(CCN3CCC(N(C)C)CC3)c3ncnc(N)c23)ccc1Cc1ncc(C)o1] | MCF7: ND<br>MDA-MB-231: ++<br>SYF (−/− Src): ND | ABL: −<br>BRK/PTK6: ++<br>KIT: −<br>mTOR: −<br>PDGFRa: −<br>RET: −<br>BLK: ++<br>FGR: +++<br>FRK/PTK5: +<br>FYN: +<br>HCK: +<br>LCK: +++<br>LYN: ++<br>SRC: ++<br>YES: +++<br>IC$_{50}^{ABL}$/IC$_{50}^{SRC}$ = 75 |

EC$_{50}$ = − > 10 µM + > 1 µM > ++ > 0.1 µM > +++
IC$_{50}$ = − > 1.0 uM > + > 100 nM > ++ > 10 nM > +++

TABLE 2

Activities of Dasatinib and structures related to the novel inhibitors but exhibiting low antiproliferative properties or low SRC-over-ABL selectivity

| Code | Structure | Antiproliferative activity (EC$_{50}$) | Target inhibition (IC$_{50}$) |
|---|---|---|---|
| Dasatinib (gold-standard Abl/Src inhibitor) POSITIVE CONTROL | 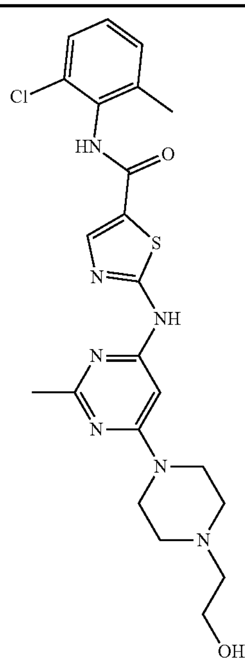 | MCF7: +++<br>MDA-MB-231: +++<br>SYF (−/− Src): +<br>NCI-H358: +<br>PC3: +<br>HT1080: −<br>MEF: +<br>BT549: − | ABL: +++<br>BRK/PTK6: ++<br>KIT: ++<br>mTOR: −<br>PDGFRa: +++<br>RET: +<br>BLK: +++<br>FGR: +++<br>FRK/PTK5: +++<br>FYN: +++<br>HCK: +++<br>LCK: +++<br>LYN: +++<br>SRC: +++<br>YES: +++<br>IC$_{50}^{ABL}$/IC$_{50}^{SRC}$ < 1 |

TABLE 2-continued

*Activities of Dasatinib and structures related to the novel inhibitors but exhibiting low antiproliferative properties or low SRC-over-ABL selectivity*

| Code | Structure | Antiproliferative activity ($EC_{50}$) | Target inhibition ($IC_{50}$) |
|---|---|---|---|
| 103 | 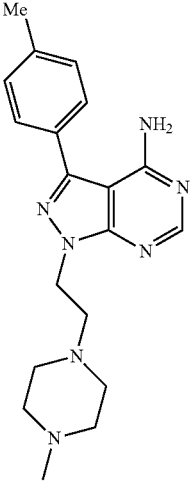 [SMILES: Cc1ccc(-c2nn(CCN3CCN(C)CC3)c3ncnc(N)c23)cc1] | MCF7: –<br>MDA-MB-231: ND<br>SYF (–/– Src): ND | ABL: –<br>BRK/PTK6: ND<br>KIT: –<br>mTOR: –<br>PDGFRa: –<br>RET: –<br>BLK: –<br>FGR: +<br>FRK/PTK5: –<br>FYN: –<br>HCK: –<br>LCK: –<br>LYN: –<br>SRC: +<br>YES: +<br>$IC_{50}^{ABL}/IC_{50}^{SRC} = 10$ |
| 113 | 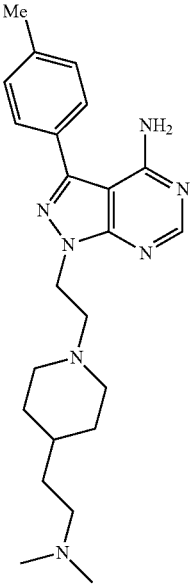 | MCF7: –<br>MDA-MB-231: ND<br>SYF (–/– Src): ND | ABL: –<br>BRK/PTK6: ND<br>KIT: –<br>mTOR: –<br>PDGFRa: –<br>RET: –<br>BLK: –<br>FGR: +<br>FRK/PTK5: –<br>FYN: –<br>HCK: –<br>LCK: –<br>LYN: –<br>SRC: –<br>YES: +<br>$IC_{50}^{ABL}/IC_{50}^{SRC} = 7$ |

TABLE 2-continued

Activities of Dasatinib and structures related to the novel inhibitors but exhibiting low antiproliferative properties or low SRC-over-ABL selectivity

| Code | Structure | Antiproliferative activity ($EC_{50}$) | Target inhibition ($IC_{50}$) |
|---|---|---|---|
| 221 | 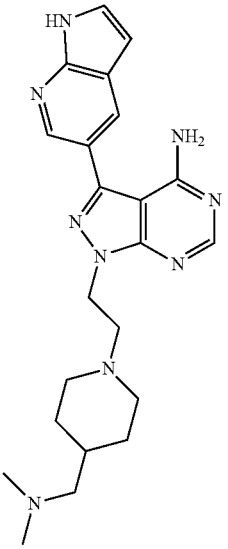 [SMILES: CN(C)CC1CCN(CCn2nc(-c3cnc4[nH]ccc4c3)c3c(N)ncnc32)CC1] | MCF7: + <br> MDA-MB-231: + <br> SYF (−/− Src): ND | ABL: + <br> BRK/PTK6: ND <br> KIT: − <br> mTOR: − <br> PDGFRa: − <br> RET: + <br> BLK: + <br> FGR: ++ <br> FRK/PTK5: + <br> FYN: ++ <br> HCK: + <br> LCK: + <br> LYN: ++ <br> SRC: ++ <br> YES: ++ <br> $IC_{50}^{ABL}/IC_{50}^{SRC} = 4$ |
| 223 | 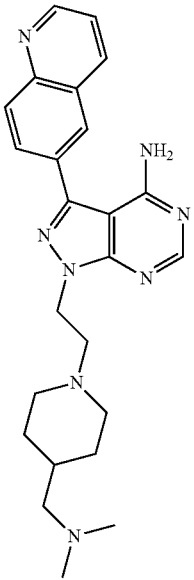 [SMILES: CN(C)CC1CCN(CCn2nc(-c3ccc4ncccc4c3)c3c(N)ncnc32)CC1] | MCF7: − <br> MDA-MB-231: ND <br> SYF (−/− Src): ND | ND |

TABLE 2-continued
Activities of Dasatinib and structures related to the novel inhibitors but exhibiting low antiproliferative properties or low SRC-over-ABL selectivity
| Code | Structure | Antiproliferative activity (EC$_{50}$) | Target inhibition (IC$_{50}$) |
|---|---|---|---|
| 224 | 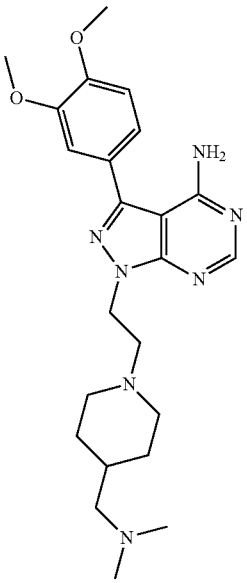 [SMILES: COc1ccc(-c2nn(CCN3CCC(CN(C)C)CC3)c3ncnc(N)c23)cc1OC] | MCF7: −<br>MDA-MB-231: ND<br>SYF (−/− Src): ND | ND |
| 225 | 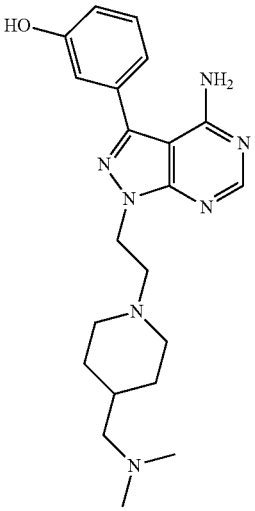 [SMILES: CN(C)CC1CCN(CCn2nc(-c3cccc(O)c3)c3c(N)ncnc32)CC1] | MCF7: −<br>MDA-MB-231: ND<br>SYF (−/− Src): ND | ND |

TABLE 2-continued

*Activities of Dasatinib and structures related to the novel inhibitors but exhibiting low antiproliferative properties or low SRC-over-ABL selectivity*

| Code | Structure | Antiproliferative activity (EC$_{50}$) | Target inhibition (IC$_{50}$) |
|---|---|---|---|
| 226 | 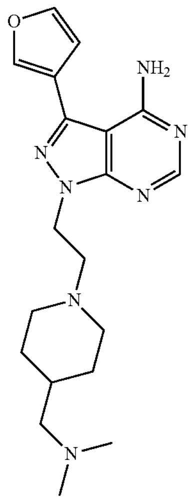 [SMILES: CN(C)CC1CCN(CCn2nc(-c3ccoc3)c3c(N)ncnc32)CC1] | MCF7: −<br>MDA-MB-231: ND<br>SYF (−/− Src): ND | ND |
| 230 | 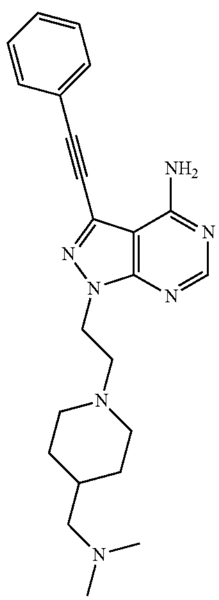 [SMILES: CN(C)CC1CCN(CCn2nc(C#Cc3ccccc3)c3c(N)ncnc32)CC1] | MCF7: −<br>MDA-MB-231: ND<br>SYF (−/− Src): ND | ND |
| 232 | 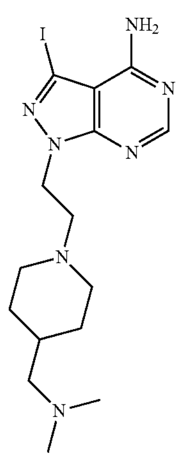 [SMILES: CN(C)CC1CCN(CCn2nc(I)c3c(N)ncnc32)CC1] | MCF7: −<br>MDA-MB-231: ND<br>SYF (−/− Src): ND | ND |

TABLE 2-continued

Activities of Dasatinib and structures related to the novel
inhibitors but exhibiting low antiproliferative properties or low SRC-over-ABL selectivity

| Code | Structure | Antiproliferative activity (EC$_{50}$) | Target inhibition (IC$_{50}$) |
|---|---|---|---|
| 402 | 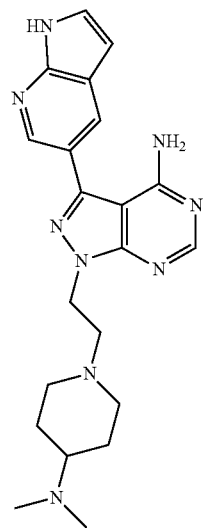 [SMILES: CN(C)C1CCN(CCn2nc(-c3cnc4[nH]ccc4c3)c3c(N)ncnc32)CC1] | MCF7: + <br> MDA-MB-231: ND <br> SYF (−/− Src): ND | ABL: + <br> BRK/PTK6: ND <br> KIT: − <br> mTOR: − <br> PDGFRa: − <br> RET: + <br> BLK: + <br> FGR: ++ <br> FRK/PTK5: + <br> FYN: ++ <br> HCK: − <br> LCK: ++ <br> LYN: ++ <br> SRC: ++ <br> YES: ++ <br> IC$_{50}^{ABL}$/IC$_{50}^{SRC}$ = 4 |
| 530 | 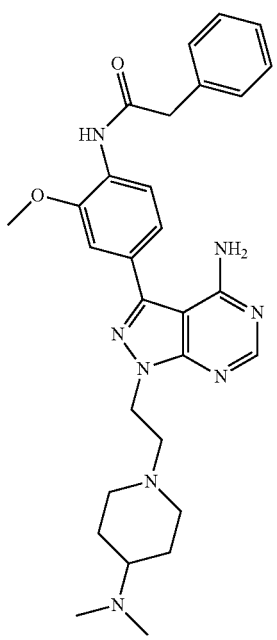 [SMILES: COc1cc(-c2nn(CCN3CCC(N(C)C)CC3)c3ncnc(N)c23)ccc1NC(=O)Cc1ccccc1] | MCF7: − <br> MDA-MB-231: − <br> SYF (−/− Src): − | ND |

TABLE 2-continued
Activities of Dasatinib and structures related to the novel
inhibitors but exhibiting low antiproliferative properties or low SRC-over-ABL selectivity
| Code | Structure | Antiproliferative activity (EC$_{50}$) | Target inhibition (IC$_{50}$) |
|---|---|---|---|
| 531 | 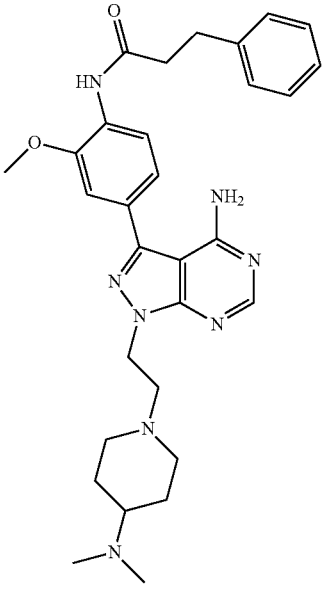 [SMILES: COc1cc(-c2nn(CCN3CCC(N(C)C)CC3)c3ncnc(N)c23)ccc1NC(=O)CCc1ccccc1] | MCF7: +<br>MDA-MB-231: −<br>SYF (−/− Src): − | ND |
| 532 | 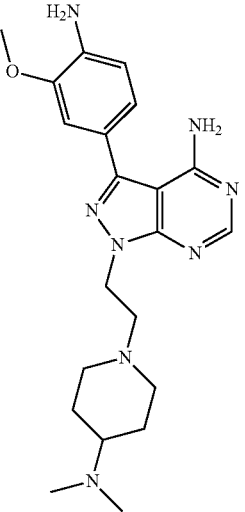 [SMILES: COc1cc(-c2nn(CCN3CCC(N(C)C)CC3)c3ncnc(N)c23)ccc1N] | MCF7: +<br>MDA-MB-231: +<br>SYF (−/− Src): − | ND |

TABLE 2-continued
*Activities of Dasatinib and structures related to the novel inhibitors but exhibiting low antiproliferative properties or low SRC-over-ABL selectivity*
| Code | Structure | Antiproliferative activity ($EC_{50}$) | Target inhibition ($IC_{50}$) |
| --- | --- | --- | --- |
| 542 | 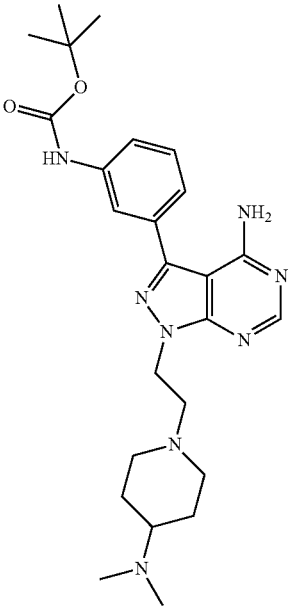 [SMILES: CN(C)C1CCN(CCn2nc(-c3cccc(NC(=O)OC(C)(C)C)c3)c3c(N)ncnc32)CC1] | MCF7: −<br>MDA-MB-231: −<br>SYF (−/− Src): − | ND |
| 549 | 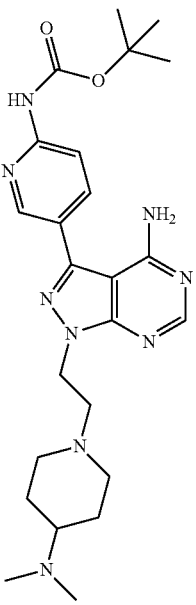 [SMILES: CN(C)C1CCN(CCn2nc(-c3ccc(NC(=O)OC(C)(C)C)nc3)c3c(N)ncnc32)CC1] | MCF7: −<br>MDA-MB-231: −<br>SYF (−/− Src): ND | ND |

TABLE 2-continued

Activities of Dasatinib and structures related to the novel inhibitors but exhibiting low antiproliferative properties or low SRC-over-ABL selectivity

| Code | Structure | Antiproliferative activity (EC$_{50}$) | Target inhibition (IC$_{50}$) |
|------|-----------|----------------------------------------|-------------------------------|
| 556 | 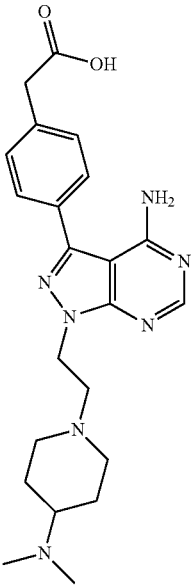 [SMILES: CN(C)C1CCN(CCn2nc(-c3ccc(CC(=O)O)cc3)c3c(N)ncnc32)CC1] | MCF7: –<br>MDA-MB-231: –<br>SYF (–/– Src): – | ABL: –<br>BRK/PTK6: –<br>KIT: –<br>mTOR: –<br>PDGFRa: –<br>RET: –<br>BLK: –<br>FGR: –<br>FRK/PTK5: –<br>FYN: –<br>HCK: –<br>LCK: –<br>LYN: –<br>SRC: –<br>YES: –<br>No inhibition found |
| 559 | 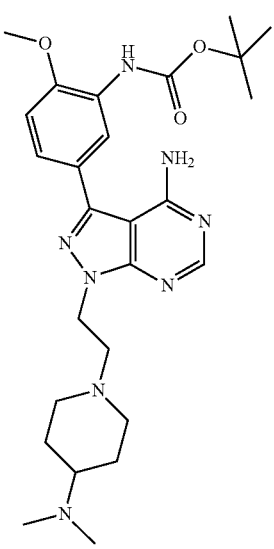 [SMILES: COc1ccc(-c2nn(CCN3CCC(N(C)C)CC3)c3ncnc(N)c23)cc1NC(=O)OC(C)(C)C] | MCF7: –<br>MDA-MB-231: –<br>SYF (–/– Src): ND | ND |

TABLE 2-continued
Activities of Dasatinib and structures related to the novel inhibitors but exhibiting low antiproliferative properties or low SRC-over-ABL selectivity
| Code | Structure | Antiproliferative activity ($EC_{50}$) | Target inhibition ($IC_{50}$) |
|---|---|---|---|
| 593 | 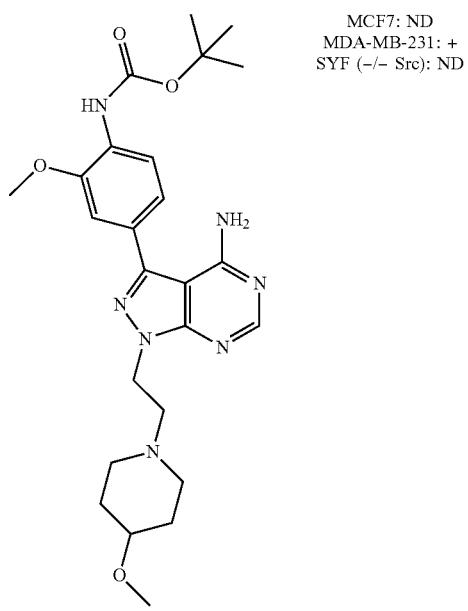 | MCF7: ND<br>MDA-MB-231: +<br>SYF (−/− Src): ND | ND |
| 597 | 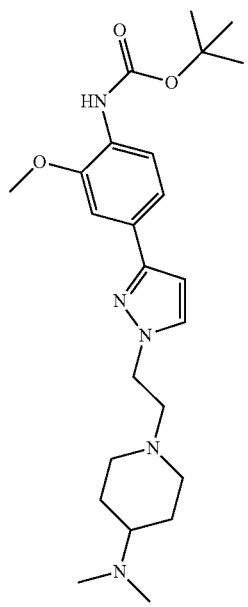 [SMILES: COc1cc(-c2ccn(CCN3CCC(N(C)C)CC3)n2)ccc1NC(=O)OC(C)(C)C] | MCF7: ND<br>MDA-MB-231: −<br>SYF (−/− Src): ND | ND |

123

TABLE 2-continued

Activities of Dasatinib and structures related to the novel
inhibitors but exhibiting low antiproliferative properties or low SRC-over-ABL selectivity

| Code | Structure | Antiproliferative activity (EC$_{50}$) | Target inhibition (IC$_{50}$) |
|---|---|---|---|
| 5-100 | 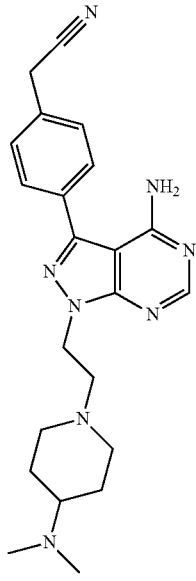 [SMILES: CN(C)C1CCN(CCn2nc(-c3ccc(CC#N)cc3)c3c(N)ncnc32)CC1] | MCF7: ND<br>MDA-MB-231: −<br>SYF (−/− Src): ND | ND |
| 5-103 | 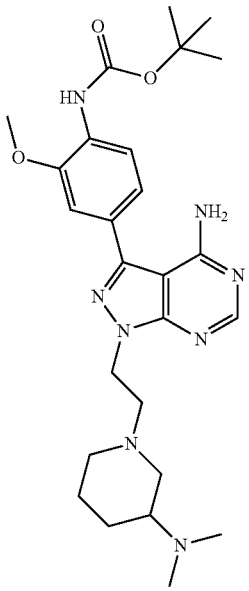 [SMILES: COc1cc(-c2nn(CCN3CCCC(N(C)C)C3)c3ncnc(N)c23)ccc1NC(=O)OC(C)(C)C] | MCF7: ND<br>MDA-MB-231: +<br>SYF (−/− Src): ND | ND |

EC$_{50}$ = − > 10 μM + > 1 μM > ++ > 0.1 μM > +++
IC$_{50}$ = − >1.0 uM > + > 100 nM > ++ > 10 nM > +++

TABLE 3

IC$_{50}$ (nM) values calculated for Dasatinib, compound 506, and compound 503 with a selection of recombinant kinases.

| Kinase | Dasatinib | Hit 506 | 503 |
|---|---|---|---|
| Abl | <0.5 | 479 | 189 |
| Fyn[1] | <0.5 | 4.1 | 4.6 |
| Kit | 39 | 5,130 | 7,130 |
| mTOR | >10$^4$ | >10$^4$ | >10$^4$ |
| PDGFRα | 9.9 | >10$^4$ | >10$^4$ |
| Src[1] | <0.5 | <0.5 | <0.5 |
| Ret | 433 | >10$^4$ | >10$^4$ |
| Yes[1] | <0.5 | <0.5 | <0.5 |

[1]SFK member.

TABLE 4

Cell Screening (EC$_{50}$*)

| Cell Line | DASATINIB | 506 | 518 | 519 | 533 | 553 | 565 |
|---|---|---|---|---|---|---|---|
| MDA-MB-231 | 13 nM | 11 nM | 39 nM | 85 nM | 167 nM | 73 nM | 31 nM |
| SYF cells (lack of Src) | 1,540 nM | 21,400 nM | 15,100 nM | 8,500 nM | 7,040 nM | 15,400 nM | 15,600 nM |

*EC$_{50}$: 8-point half-log dose response profiling against cell viability endpoint

TABLE 5

Kinase Screening (IC$_{50}$) (*) Src Family

| Kinase | DASATINIB | 506 | 518 | 519 | 533 | 553 | 585 |
|---|---|---|---|---|---|---|---|
| ABL1 | +++ | + | + | + | − | − | + |
| BRK | ++ | ++ | ++ | ++ | ++ | ++ | ++ |
| c-KIT | ++ | − | − | − | + | − | − |
| mTOR | − | − | − | − | − | − | − |
| PDGFRa | +++ | − | − | − | − | − | − |
| RET | + | − | − | − | − | − | − |
| (*) BLK | +++ | +++ | +++ | +++ | +++ | ++ | +++ |
| (*) SRC | +++ | +++ | +++ | +++ | +++ | +++ | +++ |
| (*) FGR | +++ | +++ | +++ | +++ | +++ | +++ | +++ |
| (*) FRK | +++ | +++ | +++ | +++ | + | ++ | +++ |
| (*) FYN | +++ | +++ | +++ | +++ | +++ | +++ | +++ |
| (*) HCK | +++ | +++ | +++ | +++ | +++ | ++ | +++ |
| (*) LCK | +++ | +++ | +++ | +++ | +++ | +++ | +++ |
| (*) LYN | +++ | +++ | +++ | +++ | +++ | +++ | +++ |
| (*) YES | +++ | +++ | +++ | +++ | +++ | +++ | +++ |
| IC$_{50}$ABL/IC$_{50}$SRC | 1 | 958 | 814 | 1,616 | 340 | 2,868 | 370 |

IC50 = − > 1.0 μM > + > 100 nM > ++ > 10 nM > +++

TABLE 6

Physicochemical & ADME Properties

| Properties | DASATINIB | 506 | 518 | 819 | 533 | 553 | 565 |
|---|---|---|---|---|---|---|---|
| MW | 488.0 | 510.6 | 536.7 | 560.7 | 500.6 | 479.6 | 509.6 |
| cLogP$_{OSIRIS}$ | 3.63 | 2.22 | 3.01 | 3.35 | 2.23 | 2.29 | 2.22 |
| Solubility in PBS | <0.1 mg/mL | >100 mg/mL | N/D | N/D | N/D | N/D | >100 mg/mL |
| % free in rat serum | 3% | 19.1% | 13.4% | 10.6% | 10.6% | N/D | 13.9% |
| % free in human serum | 6% | 9.4% | 17.2% | 14.3% | 11.8% | N/D | 17.7% |
| 30 $^{min}$Liver Microsome stability* | N/D | 93.6% | 87.0% | N/D | 98.8% | N/D | 78.7% |

*% of unmodified drug after 30 min incubation with liver microsomes. Controls: Lidocaine 92.0%; Propanolol 68.1%; Verapamil 8.1%.

TABLE 7 hERG Channel Inhibition, Stability in Plasma and Oral Bioavailability

| Properties | 506 | 518 | 519 | 533 | 553 | 565 |
|---|---|---|---|---|---|---|
| hERG inhibition (IC50, μM) | 18.2 | 20.1 | 12.6 | 2.55 | 12.6 | >25 |
| Stability in human plasma* | 100% | N/D | N/D | N/D | 98.3% | 94% |
| Stability in mouse plasma* | 100% | N/D | N/D | N/D | 70.4% | 100% |
| Stability in rat plasma* | 100% | N/D | N/D | N/D | 68.2% | 93.3% |
| Oral Bioavailability | 25% | N/D | N/D | N/D | N/D | 52% |
| Plasma half life | 2.9 h | N/D | N/D | N/D | N/D | 2 h |

*% of unmodified drug after 120 min in plasma. Controls: Eucatropine 10.5% (human) and 20.3 (mouse); Diltiazem 21.5% (rat).

TABLE 8

CYP P450 inhibition values at 10 μM. All the compounds led to less than 50% inhibition of metabolic activity at the concentration tested.

| Properties | 506 | 518 | 519 | 533 | 553 | 565 |
|---|---|---|---|---|---|---|
| CYP450 1A2 (% inhibition) | 24.6% | 6.9% | −1.6% | 8.3% | N/D | 4.3% |
| CYP450 3A4 (% inhibition) | −74.6% | −29.8% | −12.1% | 3.1% | N/D | 5.7% |
| CYP450 2C9 (% inhibition) | −23.1% | −92.3% | −70.3% | −35.4% | N/D | −35.8% |
| CYP450 2D6 (% inhibition) | 31.8% | 6.7% | 3.0% | 7.4% | N/D | 9.4% |
| CYP450 2C19 (% inhibition) | −5.4% | −6.5% | −3.1% | 26.8% | N/D | −0.4% |

REFERENCES

1. Hughes, J. P., Rees, S., Kalindjian, S. B. & Philpott, K. L. Principles of early drug discovery. *Br. J. Pharmacol.* 162, 1239-1249 (2011).
2. Smith, A. Screening for drug discovery. *Nature* 418, 451-463 (2002).

3. Holdgate, G. et al. Biophysical Methods in Drug Discovery from Small Molecule to Pharmaceutical. *Methods Mol. Biol.* 1008, 327-355 (2013).
4. McInnes, C. Virtual screening strategies in drug discovery. *Curr. Opin. Chem. Biol.* 11, 494-502 (2007).
5. Vistoli, G., Pedretti, A. & Testa, B. Assessing drug-likeness-what are we missing? *Drug Discov. Today* 13, 285-294 (2008).
6. Kamb, A., Wee, S. & Lengauer, C. Why is cancer drug discovery so difficult? *Nat. Rev. Drug Discov.* 6, 115-20 (2007).
7. Chin, L. & Gray, J. W. Translating insights from the cancer genome into clinical practice. *Nature* 452, 553-563 (2008).
8. Stommel, J. M. et al. Coactivation of receptor tyrosine kinases affects the response of tumor cells to targeted therapies. *Science* 318, 287-290 (2007).
9. Carragher, N., Unciti-Broceta, A. & Cameron, D. Advancing cancer drug discovery towards more agile development of targeted combination therapies. *Fut. Med. Chem.* 4, 87-105 (2012).
10. Knight, Z. A. Lin, H. & Shokat, K. M. Targeting the cancer kinome through polypharmacology. *Nat. Rev. Cancer.*, 10, 130-137 (2010).
11. Kola, I. & Landis, J. Can the pharmaceutical industry reduce attrition rates? *Nat. Rev. Drug Discov.* 3, 711-716 (2004).
12. Sassoon, I. & Blanc, V. Antibody-drug conjugate (ADC) clinical pipeline: a review. *Methods Mol. Biol.* 1045, 1-27 (2013).
13. Velema, W. A., Szymanski, W. & Feringa, B. L. Photopharmacology: beyond proof of principle. *J. Am. Chem. Soc.* 136, 2178-2191 (2014).
14. Versteegen, R. M., Rossin, R., ten Hoeve, W., Janssen H. M. & Robillard, M. S. Click to Release: Instantaneous Doxorubicin Elimination upon Tetrazine Ligation. *Angew. Chem. Int. Ed. Engl.* 52, 14112-14116 (2013).
15. Clavel, C. M. et al. Thermoresponsive Chlorambucil Derivatives for Tumour Targeting. *Angew. Chem., Int. Ed.* 50, 7124-7127 (2011).
16. Weiss, J. T. et al. Extracellular palladium-catalyzed dealkylation of 5-fluoro-1-propargyl-uracil as a bioorthogonally-activated prodrug approach. *Nat. Commun.* 5, 3277 (2014).
17. Weiss, J. T. et al. Development and Bioorthogonal Activation of Palladium-Labile Prodrugs of Gemcitabine. *J. Med. Chem.* 57, 5395-5404 (2014).
18. Lee, J. A.; Uhlik, M. T.; Moxham, C. M.; Tomandl, D. & Sail, D. J. Modern phenotypic drug discovery is a viable, neoclassic pharma strategy. *J. Med. Chem.* 55, 4527-4538 (2012).
19. Eder, J., Sedrani, R. & Wiesmann, C. The discovery of first-in-class drugs: origins and evolution Nat. Rev. Drug Discov. 13, 577-587 (2014).
20. Carragher, N. O., Brunton, V. G. & Frame, M. C. Combining imaging and pathway profiling: an alternative approach to cancer drug discovery. *Drug Discov. Today* 17, 203-214 (2012).
21. Cohen, P. Protein kinases—the major drug targets of the twenty-first century? *Nat. Rev. Drug. Discov.* 1, 309-315 (2002).
22. Zhang, J.; Yang, P. L & Gray, N. S. Targeting cancer with small molecule kinase inhibitors. *Nat. Rev. Cancer.* 9, 28-39 (2009).
23. Lu, L. et al. Hippo signaling is a potent in vivo growth and tumor suppressor pathway in the mammalian liver. *Proc. Natl. Acad. Sci. USA* 107, 1437-1442 (2010).
24. Zhou, B.-B. S. & Bartek, J. Targeting the checkpoint kinases: chemosensitization versus chemoprotection. *Nat. Rev. Cancer* 4, 216-225 (2004).
25. Fujimoto, H. et al. Regulation of the antioncogenic Chk2 kinase by the oncogenic Wip1 phosphatase. *Cell Death Differ.* 13, 1170-1180 (2006).
26. Wilhelm, S. et al. Discovery and development of sorafenib: a multikinase inhibitor for treating cancer. *Nat. Rev. Drug Discov.* 5, 835-844 (2006).
27. Greuber, E. K.; Smith-Pearson, P.; Wang, J. & Pendergast, A. M. Role of ABL family kinases in cancer from leukaemia to solid tumours. *Nat. Rev. Cancer.* 13, 559-571 (2013).
28. Noren, N. K.; Foos, G.; Hauser, C. A. & Pasquale, E. B. The EphB4 receptor suppresses breast cancer cell tumorigenicity through an Abl-Crk pathway. *Nat. Cell Biol.* 8, 815-825 (2006).
29. Allington, T. M.; Galliher-Beckley, A. J. & Schiemann, W. P. Activated Abl kinase inhibits oncogenic transforming growth factor-beta signaling and tumorigenesis in mammary tumors. *FASEB J.* 23, 4231-4243 (2009).
30. Gil-Henn, H. et al. Arg/Abl2 promotes invasion and attenuates proliferation of breast cancer in vivo. *Oncogene* 32, 2622-2630 (2013).
31. Hanke, J. H. et al. Discovery of a novel, potent, and Src family-selective tyrosine kinase inhibitor. Study of Lck- and FynT-dependent T cell activation, *J. Biol. Chem.* 271, 695-701 (1996).
32. Tatton, L., Morley, G. M., Chopra, R. & Khwaja, A. The Src-selective kinase inhibitor PP1 also inhibits Kit and Bcr-Abl tyrosine kinases. *J. Biol. Chem.* 278, 4847-4853 (2003).
33. Jester, B. W., Gaj, A., Shomin, C. D., Cox, K. J. & Ghosh, I. Testing the promiscuity of commercial kinase inhibitors against the AGC kinase group using a split-luciferase screen. *J. Med. Chem.* 55, 1526-1537 (2012).
34. Dinér, P., Alao, J. P., Söderlund, J., Sunnerhagen, P. & Grøtli, M. Preparation of 3-substituted-1-isopropyl-1H-pyrazolo[3,4-d]pyrimidin-4-amines as RET kinase inhibitors. *J. Med. Chem.* 55, 4872-4876 (2012).
35. Apsel, B. et al. Targeted polypharmacology: discovery of dual inhibitors of tyrosine and phosphoinositide kinases. *Nat. Chem. Biol.* 4, 691-699 (2008).
36. Antonelli, A., et al. CLM29, a multi-target pyrazolopyrimidine derivative, has anti-neoplastic activity in medullary thyroid cancer in vitro and in vivo. *Mol. Cell Endocrinol.* 393, 56-64 (2014).
37. Schindler, T. et al. Crystal structure of Hck in complex with a Src family-selective tyrosine kinase inhibitor. *Mol. Cell.* 3, 639-648 (1999).
38. Knowles, P. P. et al. Structure and chemical inhibition of the RET tyrosine kinase domain. *J. Biol. Chem.* 281, 33577-87 (2006).
39. Liu, Y. & Gray, N. S. Rational design of inhibitors that bind to inactive kinase conformations. *Nat. Chem. Bio.* 2, 358-364 (2006).
40. Liu, Y. et al. Structural basis for selective inhibition of Src family kinases by PP1. *Chem Biol.* 8, 671-678 (1999).
41. Dar, A. C., Lopez, M. S. & Shokat, K. M. Small molecule recognition of c-Src via the Imatinib-binding conformation. *Chem. Biol.* 15, 1015-1022 (2008).
42. Hann, M. M. & Keserü, G. M. Finding the sweet spot: the role of nature and nurture in medicinal chemistry. *Nat. Rev. Drug Discov.* 11, 355-365 (2012).
43. Hsieh, A. C. et al. The translational landscape of mTOR signalling steers cancer initiation and metastasis. Nature 485, 55-61 (2012).

44. Kerkela R, Grazette L, Yacobi R, Iliescu C, Patten R, Beahm C, Walters B, Shevtsov S, Pesant S, Clubb F J, Rosenzweig A, Salomon R N, Van Etten R A, Airoy J, Durand J B, Force T. (2006). Cardiotoxicity of the cancer therapeutic agent imatinib mesylate. Nature Med August; 12(8):908-16.

45. Allington, T. M.; Galliher-Beckley, A. J.; Schiemann, W. P. Activated Abl kinase inhibits oncogenic transforming growth factor-beta signaling and tumorigenesis in mammary tumors. FASEB J. 2009, 23, 4231-4243.

46. Boyce, B. F., Xing, L, Yao, Z., Yamashita, T., Shakespeare, W. C., Wang, Y., Metcalf, C. A., 3rd, Sundaramoorthi, R., Dalgarno, D. C., Iuliucci, J. D., and Sawyer, T. K. (2006). SRC inhibitors in metastatic bone disease. Clin Cancer Res 12, 6291s-6295s.

47. Brunton, V. G., and Frame, M. C. (2008). Src and focal adhesion kinase as therapeutic targets in cancer. Curr Opin Pharmacol 8, 427-432.

48. Chaturvedi, D., Gao, X., Cohen, M. S., Taunton, J., and Patel, T. B. (2009). Rapamycin induces transactivation of the EGFR and increases cell survival. Oncogene 28, 1187-1196.

49. Creedon, H., and Brunton, V. G. (2012). Src kinase inhibitors: promising cancer therapeutics? Crit Rev Oncog 17, 145-159.

50. Girotti R et al. (2015). Paradox-Breaking RAF Inhibitors that Also Target SRC Are Effective in Drug-Resistant BRAF Mutant Melanoma. Cancer Cell 27(1): 85-96.

51. Kerkela R, Grazette L, Yacobi R, Iliescu C, Patten R, Beahm C, Walters B, Shevtsov S, Pesant S, Clubb F J, Rosenzweig A, Salomon R N, Van Etten R A, Alroy J, Durand J B, Force T. (2006). Cardiotoxicity of the cancer therapeutic agent imatinib mesylate. Nature Med 12(8): 908-16.

52. Qiu Z, Cang Y, Goff S P. (2010). Abl family tyrosine kinases are essential for basement membrane integrity and cortical lamination in the cerebellum. J Neurosci. 2010 Oct. 27; 30(43):14430-9.

53. De Wispelaere, M., Lacroix, A. J., and Yang, P. L. (2013). The small molecules AZD0530 and dasatinib inhibit dengue virus RNA replication via Fyn kinase. J Virol 87, 7367-7381.

54. Duxbury, M. S., Ito, H., Zinner, M. J., Ashley, S. W., and Whang, E. E. (2004). Inhibition of SRC tyrosine kinase impairs inherent and acquired gemcitabine resistance in human pancreatic adenocarcinoma cells. Clin Cancer Res 10, 2307-2318.

55. Gil-Henn, H.; Patsialou, A.; Wang, Y.; Warren, M. S.; Condeelis, J. S.; Koleske, A. J. Arg/Abl2 promotes invasion and attenuates proliferation of breast cancer in vivo. Oncogene, 2013, 32, 2622-2630.

56. Hawthorne, V. S., Huang, W. C., Neal, C. L, Tseng, L. M., Hung, M. C., and Yu, D. (2009). ErbB2-mediated Src and signal transducer and activator of transcription 3 activation leads to transcriptional up-regulation of p21Cip1 and chemoresistance in breast cancer cells. Mol Cancer Res 7, 592-600.

57. Kopetz, S., Lesslie, D. P., Dallas, N. A., Park, S. I., Johnson, M., Parikh, N. U., Kim, M. P., Abbruzzese, J. L., Ellis, L. M., Chandra, J., and Gallick, G. E. (2009). Synergistic activity of the SRC family kinase inhibitor dasatinib and oxaliplatin in colon carcinoma cells is mediated by oxidative stress. Cancer Res 69, 3842-3849.

58. Mayer, E. L., and Krop, I. E. (2010). Advances in targeting SRC in the treatment of breast cancer and other solid malignancies. Clin Cancer Res 16, 3526-3532.

59. Mccarthy, S. D., Jung, D., Sakac, D., and Branch, D. R. (2014). c-Src and Pyk2 protein tyrosine kinases play protective roles in early HIV-1 infection of CD4+ T-cell lines. J Acquir Immune Defic Syndr 66, 118-126.

60. Murrills, R. J., Fukayama, S., Boschelli, F., Matteo, J. J., Owens, J., Golas, J. M., Patel, D., Lane, G., Liu, Y. B., Carter, L., Jussif, J., Spaulding, V., Wang, Y. D., Boschelli, D. H., Mckew, J. C., Li, X. J., Lockhead, S., Milligan, C., Kharode, Y. P., Diesl, V., Bai, Y., Follettie, M., Bex, F. J., Komm, B., and Bodine, P. V. (2012). Osteogenic effects of a potent Src-over-Abl-selective kinase inhibitor in the mouse. J Pharmacol Exp Ther 340, 676-687.

61. Myoui, A., Nishimura, R., Williams, P. J., Hiraga, T., Tamura, D., Michigami, T., Mundy, G. R., and Yoneda, T. (2003). C-SRC tyrosine kinase activity is associated with tumor colonization in bone and lung in an animal model of human breast cancer metastasis. Cancer Res 63, 5028-5033.

62. Noren, N. K.; Foos, G.; Hauser, C. A.; Pasquale, E. B (2006). The EphB4 receptor suppresses breast cancer cell tumorigenicity through an Abl-Crk pathway. Nat. Cell Biol. 8, 815-825.

63. Park, G. B., Kim, D., Kim, Y. S., Kim, S., Lee, H. K., Yang, J. W., and Hur, D. Y. (2014). The Epstein-Barr virus causes epithelial-mesenchymal transition in human corneal epithelial cells via Syk/src and Akt/Erk signaling pathways. Invest Ophthalmol Vis Sci 55, 1770-1779.

64. Sawyers, C. L., Mclaughlin, J., Goga, A., Havlik, M., and Witte, O. (1994). The nuclear tyrosine kinase c-Abl negatively regulates cell growth. Cell 77, 121-131.

65. Wheeler, D. L., Iida, M., Kruser, T. J., Nechrebecki, M. M., Dunn, E. F., Armstrong, E. A., Huang, S., and Harari, P. M. (2009). Epidermal growth factor receptor cooperates with Src family kinases in acquired resistance to cetuximab. Cancer Biol Ther 8, 696-703.

66. Zhang, S., Huang, W. C., Li, P., Guo, H., Poh, S. B., Brady, S. W., Xiong, Y., Tseng, L. M., Li, S. H., Ding, Z., Sahin, A. A., Esteva, F. J., Hortobagyi, G. N., and Yu, D. (2011). Combating trastuzumab resistance by targeting SRC, a common node downstream of multiple resistance pathways. Nat Med 17, 461-469.

67. Summy J M, Gallick G E (2003). Src family kinases in tumor progression and metastasis. Cancer Metastasis Rev. 22(4):337-58.

68. Frame M C et al. (2002). v-Src's hold over actin and cell adhesions. Nat Rev Mol Cell Biol. 3(4):233-45.

69. Yoo S K et al. (2012) Early redox, Src family kinase, and calcium signaling integrate wound responses and tissue regeneration in zebrafish. J Cell Biol 199, 225-234.

70. Tyryshkin A et al., SRC kinase is a novel therapeutic target in lymphangioleiomyomatosis. Cancer Res; 74(7) Apr. 1, 2014.

71. Walcher D et al., C-Peptide induces vascular smooth muscle cell proliferation: involvement of SRC-kinase, phosphatidylinositol 3-kinase, and extracellular signal-regulated kinase 1/2. Circulation Research. 2006; 99: 1181-1187.

72. Cho H M et al., The Src/PLC/PKC/MEK/ERK signaling pathway is involved in aortic smooth muscle cell proliferation induced by glycated LDL. Molecules and Cells [2005, 19(1):60-6].

73. Yang K1, Belrose J, Trepanier C H, Lei G, Jackson M F, MacDonald J F. Fyn, a potential target for Alzheimer's disease. *J Alzheimers Dis.* 2011, 27, 243-52.

74. Nygaard H B, van Dyck C H, Strittmatter S M. Fyn kinase inhibition as a novel therapy for Alzheimer's disease. *Alzheimers Res Ther.* 2014, 6, 8.
75. Kaufman A C1, Salazar S V, Haas L T, Yang J, Kostylev M A, Jeng A T, Robinson S A, Gunther E C, van Dyck C H, Nygaard H B, Strittmatter S M. Fyn inhibition rescues established memory and synapse loss in Alzheimer mice. *Ann Neural.* 2015, doi: 10.1002/ana.24394 [ahead of print].
76. Nygaard H B, Wagner A F, Bowen G S, Good S P, MacAvoy M G, Strittmatter K A, Kaufman A C, Rosenberg B J, Sekine-Konno T, Varma P, Chen K, Koleske A J, Reiman E M, Strittmatter S M, van Dyck C H. A phase Ib multiple ascending dose study of the safety, tolerability, and central nervous system availability of AZD0530 (saracatinib) in Alzheimer's disease. *Alzheimers Res Ther.* 2015, 7, 35.
77. H. Ma, S. Deacon & K. Horiuchi. The challenge of selecting protein kinase assays for lead discovery optimization. *Expert Opin. Drug Discov.* (2008) 3(6).
78. Patton, E. E.; Dhillon, P.; Amatruda, J. F.; Ramakrishnan, L. Spotlight on zebrafish: translational impact. *Dis. Model. Mech.* 2014, 7, 731-733.
79. Gallardo, V. E.; Varshney, G. K.; Lee, M.; Bupp, S.; Xu, L; Shinn, P.; Crawford, N. P.; Inglese, J.; Burgess, S. M. Phenotype-driven chemical screening in zebrafish for compounds that inhibit collective cell migration identifies multiple pathways potentially involved in metastatic invasion. *Dis. Model. Mech.* 2015, 8, 565-576.
80. Xiao, T.; Roeser, T.; Staub, W.; Baier H. A GFP-based genetic screen reveals mutations that disrupt the architecture of the zebrafish retinotectal projection. *Development* 2005, 132, 2955-2967.
81. Qiu, Z.; Cang, Y.; Goff, S. P. c-Abl tyrosine kinase regulates cardiac growth and development. *Proc. Natl. Acad. Sci. USA* 2010, 107, 1136-1141.
82. Chislock, E. M.; Ring, C.; Pendergast, A. M. Abl kinases are required for vascular function, Tie2 expression, and angiopoietin-1-mediated survival. *Proc. Natl. Acad. Sci. USA* 2013, 110, 12432-12437.
83. Animal experiments were performed under Home Office License in compliance with the Animals (Scientific Procedures) Act 1986 and approved by the University of Edinburgh Ethics Committee.

The invention claimed is:

1. A compound of formula I, or a pharmaceutically acceptable salt or ester thereof,

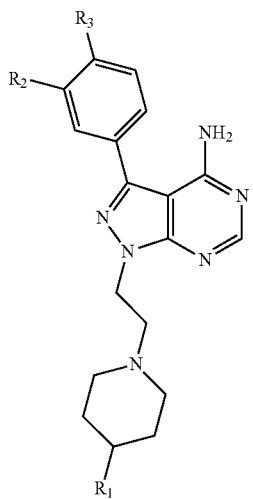

(I)

wherein:

$R_1$ is $(CH_2)_m NR_{11}R_{12}$;

$R_2$ is selected from H, halo, $OR_{13}$, $NHR_{13}$, alkyl, alkenyl and alkynyl;

$R_3$ is selected from alkyl, alkenyl, alkynyl, aryl, halo, aryloxy, $NHCO_2R_4$, $NHCONR_5R_6$, $NHCOR_7$, NH-alkyl, NH-alkenyl, $NH(CH_2)_n$-aryl, $(CH_2)_p$-heteroaryl, $(CH_2)_q CO_2 R_8$, $(CH_2)_r COR_9$ and $NHSO_2R_{10}$, wherein each alkyl, alkenyl, aryl or heteroaryl moiety in the aforementioned list is optionally further substituted by one or more groups selected from alkyl, halo, OH, $NH_2$, alkoxy, aryloxy, alkylamino, arylamino, carboxyl and carboxamide;

$R_4$ to $R_{10}$ and $R_{13}$ are each independently selected from alkyl, alkenyl and aryl;

$R_{11}$ and $R_{12}$ are each independently selected from alkyl and alkenyl; or $R_{11}$ and $R_{12}$ are linked together with the nitrogen to which they are attached to form a heterocycloalkyl or heterocycloalkenyl group;

n, m, p, q and r are each independently selected from 0, 1, 2, 3, 4, 5 and 6.

2. A compound according to claim 1 wherein $R_{11}$ and $R_{12}$ are alkyl.

3. A compound according to claim 1 wherein $R_{11}$ and $R_{12}$ are linked together with the nitrogen to which they are attached to form a heterocycloalkyl group.

4. A compound according to claim 1 wherein $R_1$ is selected from $NMe_2$, $CH_2NMe_2$, pyrrolidin-1-yl and piperidin-1-yl.

5. A compound according to claim 1 wherein $R_2$ is selected from H OMe and alkoxy and alkoxy.

6. A compound according to claim 1 wherein $R_3$ is selected from alkyl, $NHCO_2R_4$, $NHCOR_7$, $NH(CH_2)_n$-aryl, $NHCONR_5R_6$, $(CH_2)_p$-heteroaryl and $(CH_2)_q CO_2 R_8$.

7. A compound according to claim 1 wherein $R_4$ to $R_{10}$ are each independently alkyl.

8. A compound according to claim 1 wherein $R_3$ is selected from Me, $NHCO_2$-alkyl, NHCO-alkyl, $NH(CH_2)_n$-aryl, NHCONH-alkyl, $(CH_2)_p$-heteroaryl and $(CH_2)_q CO_2$-alkyl.

9. A compound according to claim 1 wherein each of n, p, q and r is 1.

10. A compound according to claim 1 wherein $R_3$ is selected from Me, $NHCO_2$-$^tBu$, $NHCOCH_2C(Me)_3$, $NHCH_2$phenyl, NHCONH-$^tBu$, $CH_2$-(4-methyl-oxazol-2-yl) and $CH_2CO_2$-$^tBu$.

11. A compound according to claim 1 wherein $R_3$ is selected from Me and $NHCO_2$—$^tBu$.

12. A compound which is selected from the following:
| Compound No: | Structure |
|---|---|
| 109 | 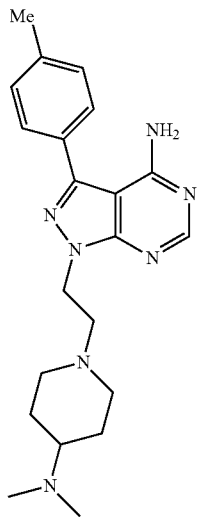 [SMILES: Cc1ccc(-c2nn(CCN3CCC(N(C)C)CC3)c3ncnc(N)c23)cc1] |
| 105 | 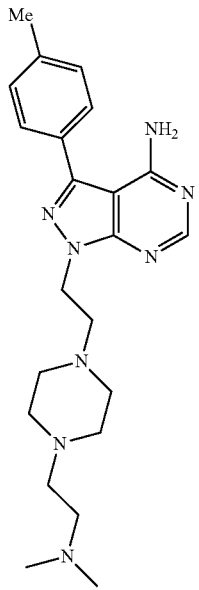 [SMILES: Cc1ccc(-c2nn(CCN3CCN(CCN(C)C)CC3)c3ncnc(N)c23)cc1] |
-continued
| Compound No: | Structure |
|---|---|
| 112 | 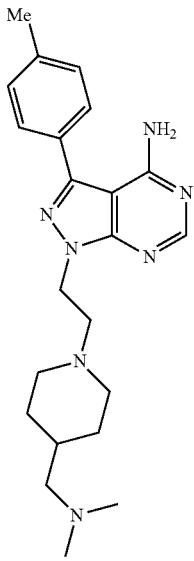 [SMILES: Cc1ccc(-c2nn(CCN3CCC(CN(C)C)CC3)c3ncnc(N)c23)cc1] |
| 503 | 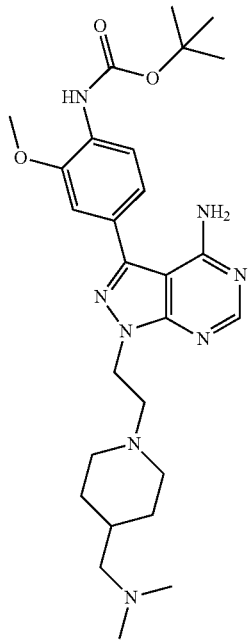 [SMILES: COc1cc(-c2nn(CCN3CCC(CN(C)C)CC3)c3ncnc(N)c23)ccc1NC(=O)OC(C)(C)C] |

| Compound No: | Structure |
|---|---|
| 506 | 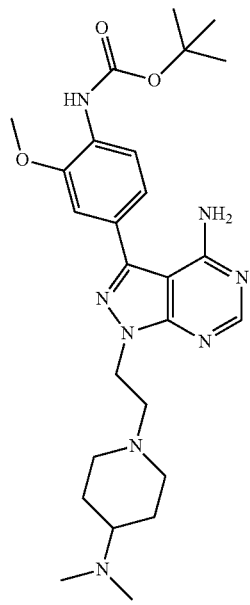 |
| 518 | |
| Compound No: | Structure |
|---|---|
| 519 | 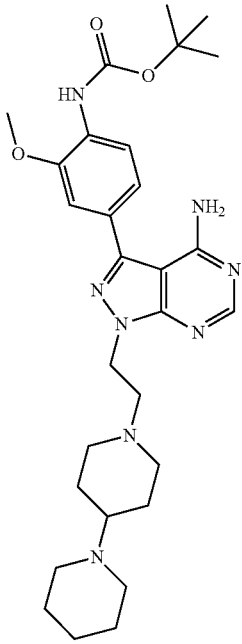 [SMILES: COc1cc(-c2nn(CCN3CCC(N4CCCCC4)CC3)c3ncnc(N)c23)ccc1NC(=O)OC(C)(C)C] |
| 526 | 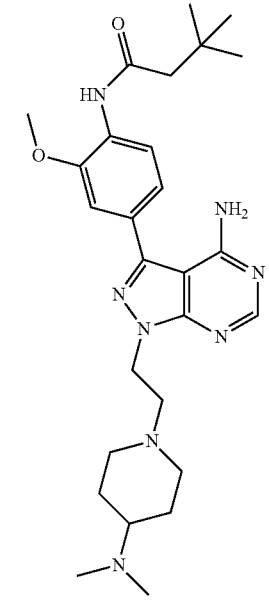 [SMILES: COc1cc(-c2nn(CCN3CCC(N(C)C)CC3)c3ncnc(N)c23)ccc1NC(=O)CC(C)(C)C] |

| Compound No: | Structure |
|---|---|
| 533 | 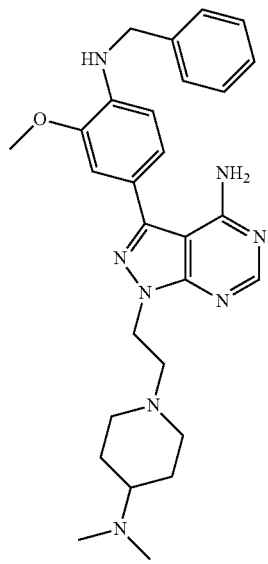 [SMILES: COc1cc(-c2nn(CCN3CCC(N(C)C)CC3)c3ncnc(N)c23)ccc1NCc1ccccc1] |
| 540 | 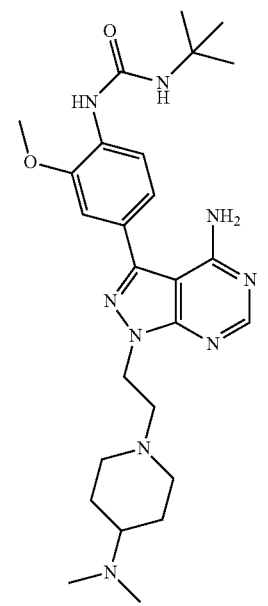 [SMILES: COc1cc(-c2nn(CCN3CCC(N(C)C)CC3)c3ncnc(N)c23)ccc1NC(=O)NC(C)(C)C] |
| Compound No: | Structure |
|---|---|
| 543 | 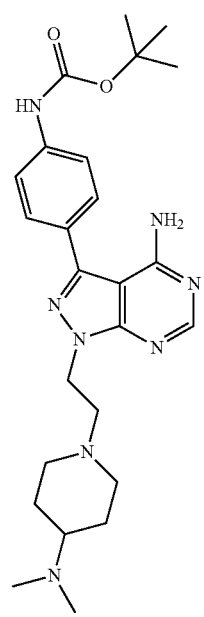 [SMILES: CN(C)C1CCN(CCn2nc(-c3ccc(NC(=O)OC(C)(C)C)cc3)c3c(N)ncnc32)CC1] |
| 553 | 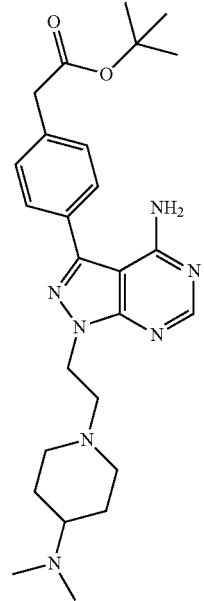 [SMILES: CN(C)C1CCN(CCn2nc(-c3ccc(CC(=O)OC(C)(C)C)cc3)c3c(N)ncnc32)CC1] |

-continued

| Compound No: | Structure |
|---|---|
| 565 | 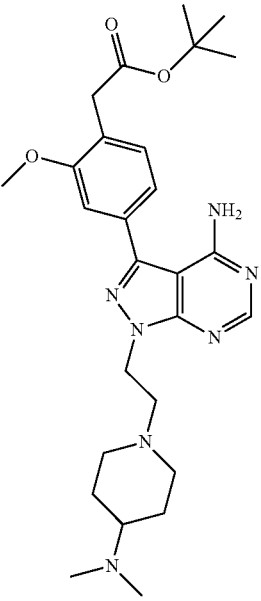 [SMILES: COc1cc(-c2nn(CCN3CCC(N(C)C)CC3)c3ncnc(N)c23)ccc1CC(=O)OC(C)(C)C] |
| 584 | 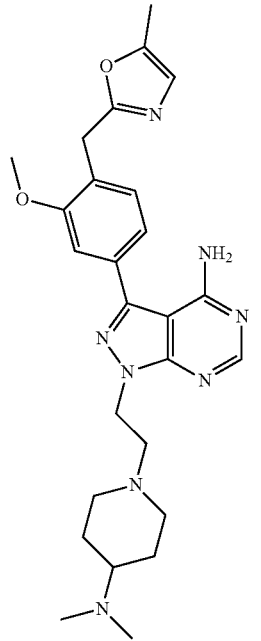 [SMILES: COc1cc(-c2nn(CCN3CCC(N(C)C)CC3)c3ncnc(N)c23)ccc1Cc1ncc(C)o1] | and pharmaceutically acceptable salts thereof.

13. A pharmaceutical composition comprising a compound according to claim 1 and a pharmaceutically acceptable carrier, diluent or excipient.

14. A compound of formula (II), or a pharmaceutically acceptable salt thereof,

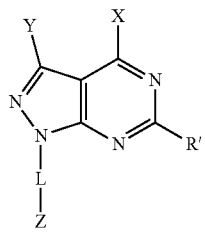

wherein:
X is selected from amino, alkylamino, arylamino, hydroxyl, alkoxy and aryloxy;
L is an alkylene linker group having from 1 to 6 carbon atoms, wherein said alkylene linker group is optionally substituted by one or more R" groups;
Z is a piperidinyl or piperazinyl group that is optionally substituted by one or more groups selected from R" and $(CH_2)_m NR_{11}R_{12}$;
Y is an aryl or heteroaryl group, wherein said aryl or heteroaryl group is optionally substituted by one or more groups selected from halo, $OR_{13}$, alkyl, aryl, alkenyl, alkynyl, $NHCO_2R_4$, $NHCONR_5R_6$, $NHCOR_7$, NH-alkyl, NH-alkenyl, $NH(CH_2)_n$-aryl, $(CH_2)_p$-heteroaryl, $(CH_2)_q CO_2R_8$, $(CH_2)_r COR_9$ and $NHSO_2R_{10}$, wherein each alkyl, alkenyl, aryl or heteroaryl moiety in the aforementioned list is optionally further substituted by one or more groups selected from alkyl, halo, OH, $NH_2$, alkoxy, aryloxy, alkylamino, arylamino, carboxyl and carboxamide;
R' is selected from H, alkyl, aryl, heteroaryl and halo, wherein said alkyl, aryl and heteroaryl groups may be optionally substituted by one or more R" groups;
$R_4$ to $R_{10}$ and $R_{13}$ are each independently selected from alkyl, alkenyl and aryl; and
n, m, p, q and r are each independently selected from 0, 1, 2, 3, 4, 5 and 6;
each R" is independently selected from alkyl, OH, alkoxy and halo;
$R_{11}$ and $R_{12}$ are each independently selected from alkyl and alkenyl; or $R_{11}$ and $R_{12}$ are linked together with the nitrogen to which they are attached to form a heterocycloalkyl or heterocycloalkenyl group;
for use in treating a disorder selected from Alzheimer's disease, Epstein Barr Virus and Dengue fever.

15. A pharmaceutical composition according to claim 13 which further comprises a second therapeutic agent.

16. A combination comprising a compound according to claim 1 and a further therapeutic agent.

17. A method of treating a mammal having a disease state alleviated by the selective inhibition of a Src family kinase, wherein the disease is selected from cancer, a viral disorder, Alzheimer's disease, Parkinson's disease, and osteoporosis, and wherein the method comprises administering to a mammal a therapeutically effective amount of a compound according to claim 1.

18. A method according to claim 17, wherein the disease is cancer.

19. A method according to claim 17, wherein the disease is a viral disorder.

20. A method according to claim 19 wherein the viral disorder is selected from Epstein Barr Virus, Dengue Virus infection and HIV.

21. A method according to claim 17, wherein the disease is osteoporosis.

22. A compound according to claim 17 wherein the neurological disorder is Alzheimer's disease.

23. A method according to claim 17 wherein the disease state is alleviated by the selective inhibition of a Src family kinase over Abl-kinase.

24. A process for preparing a compound of formula I as defined in claim 1, said process comprising the steps of:

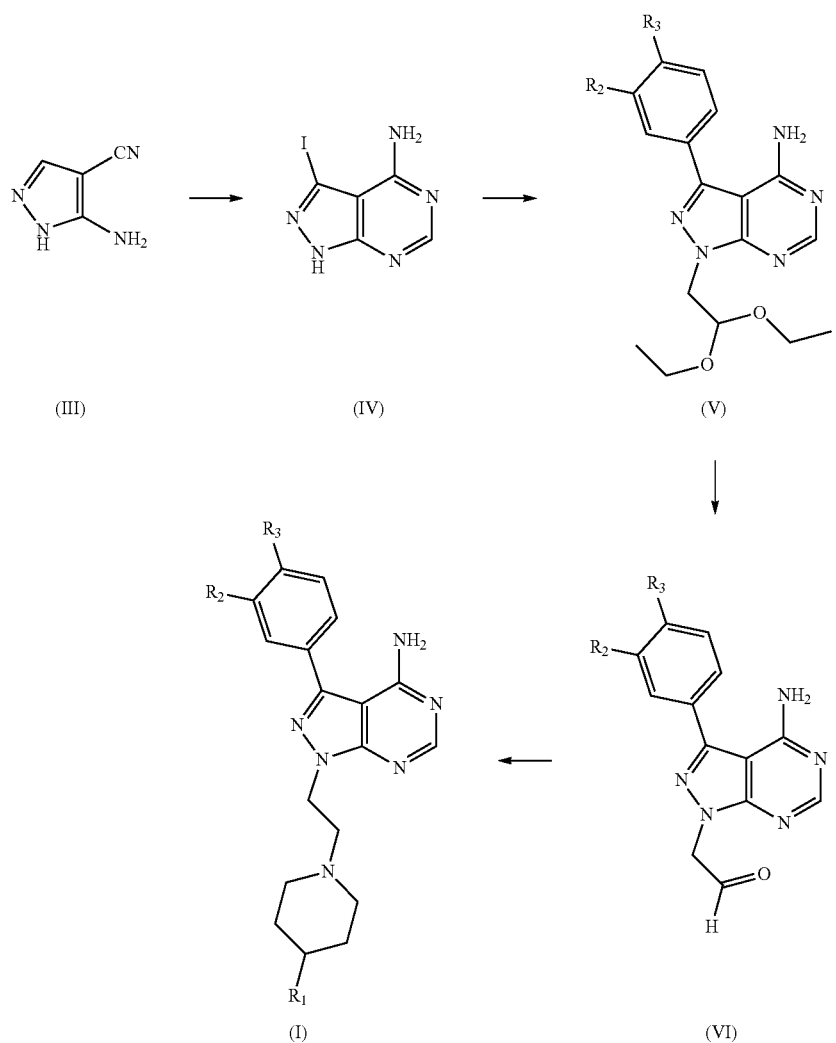
(i) converting a compound of formula (III) to a compound of formula (IV);
(ii) converting said compound of formula (IV) to a compound of formula (V);
(iii) converting said compound of formula (V) to a compound of formula (VI); and
(iv) converting said compound of formula (VI) to a compound of formula (I).
* * * * *

UNITED STATES PATENT AND TRADEMARK OFFICE
CERTIFICATE OF CORRECTION

PATENT NO. : 10,294,227 B2
APPLICATION NO. : 15/576101
DATED : May 21, 2019
INVENTOR(S) : Asier Unciti-Broceta et al.

Page 1 of 1

It is certified that error appears in the above-identified patent and that said Letters Patent is hereby corrected as shown below:

In the Claims

Column 132, Line 43,  Replace "H OMe and alkoxy and alkoxy." with
-- H OMe and alkoxy. --

Signed and Sealed this
Fifteenth Day of October, 2019

Andrei Iancu
*Director of the United States Patent and Trademark Office*